US011274296B2

(12) United States Patent
Gander et al.

(10) Patent No.: US 11,274,296 B2
(45) Date of Patent: *Mar. 15, 2022

(54) SIMULTANEOUS MULTIPLEX GENOME EDITING IN YEAST

(71) Applicant: Inscripta, Inc., Boulder, CO (US)

(72) Inventors: Miles Gander, Boulder, CO (US); Tian Tian, Boulder, CO (US); Skylar Stefani, Boulder, CO (US); Patrick Westfall, Boulder, CO (US)

(73) Assignee: Inscripta, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/463,956

(22) Filed: Sep. 1, 2021

(65) Prior Publication Data

US 2021/0395727 A1  Dec. 23, 2021

Related U.S. Application Data

(63) Continuation of application No. 17/230,241, filed on Apr. 14, 2021, now Pat. No. 11,136,572, which is a continuation of application No. 17/061,143, filed on Oct. 1, 2020, now Pat. No. 11,001,831, which is a continuation-in-part of application No. 16/827,639, filed on Mar. 23, 2020, now Pat. No. 10,815,467.

(60) Provisional application No. 62/823,136, filed on Mar. 25, 2019, provisional application No. 62/871,879, filed on Jul. 9, 2019, provisional application No. 62/960,291, filed on Jan. 13, 2020.

(51) Int. Cl.
*C12N 15/10* (2006.01)

(52) U.S. Cl.
CPC .............................. *C12N 15/1037* (2013.01)

(58) Field of Classification Search
None
See application file for complete search history.

(56) References Cited

U.S. PATENT DOCUMENTS

| | | | |
|---|---|---|---|
| 6,391,582 B2 | 5/2002 | Ying et al. | |
| 6,837,995 B1 | 1/2005 | Vassarotti et al. | |
| 7,166,443 B2 | 1/2007 | Walker et al. | |
| 8,332,160 B1 | 12/2012 | Platt et al. | |
| 8,697,359 B1 | 4/2014 | Zhang et al. | |
| 8,926,977 B2 | 1/2015 | Miller et al. | |
| 9,260,505 B2 | 2/2016 | Weir et al. | |
| 9,361,427 B2 | 6/2016 | Hillson | |
| 9,499,855 B2 | 11/2016 | Hyde et al. | |
| 9,776,138 B2 | 10/2017 | Innings et al. | |
| 9,790,490 B2 | 10/2017 | Zhang et al. | |
| 9,896,696 B2 | 2/2018 | Begemann et al. | |
| 9,982,279 B1 | 5/2018 | Gill et al. | |
| 9,988,624 B2 | 6/2018 | Serber et al. | |
| 10,011,849 B1 | 7/2018 | Gill et al. | |
| 10,017,760 B2 | 7/2018 | Gill et al. | |
| 10,227,576 B1 | 3/2019 | Cameron et al. | |
| 10,266,851 B2 | 4/2019 | Chen | |
| 10,704,033 B1 | 7/2020 | Kim et al. | |
| 10,724,021 B1 | 7/2020 | Kim et al. | |
| 10,745,678 B1 | 8/2020 | Kim et al. | |
| 10,767,169 B1 | 9/2020 | Kim et al. | |
| 10,815,467 B2 * | 10/2020 | Gander | C12N 9/22 |
| 10,837,021 B1 | 11/2020 | Tian et al. | |
| 10,927,385 B2 | 2/2021 | Kannan et al. | |
| 11,001,831 B2 * | 5/2021 | Gander | C40B 40/06 |
| 11,034,945 B2 * | 6/2021 | Gander | C12N 9/22 |
| 11,136,572 B2 * | 10/2021 | Gander | C12N 15/81 |
| 11,149,260 B2 * | 10/2021 | Stefani | C12N 15/85 |
| 2002/0139741 A1 | 10/2002 | Kopf | |
| 2004/0110253 A1 | 6/2004 | Kappler et al. | |
| 2007/0020761 A1 | 1/2007 | Yu et al. | |
| 2010/0076057 A1 | 3/2010 | Sontheimer et al. | |
| 2011/0294217 A1 | 12/2011 | McConnell-Smith et al. | |
| 2013/0236970 A1 | 9/2013 | Anneren et al. | |
| 2014/0068797 A1 | 3/2014 | Doudna et al. | |
| 2014/0199767 A1 | 7/2014 | Barrangou et al. | |
| 2014/0242033 A1 | 8/2014 | Gruber et al. | |
| 2014/0273226 A1 | 9/2014 | Wu et al. | |
| 2015/0071898 A1 | 3/2015 | Liu et al. | |
| 2015/0098954 A1 | 4/2015 | Hyde et al. | |
| 2015/0159174 A1 | 6/2015 | Frendewey et al. | |
| 2015/0176013 A1 | 6/2015 | Musunuru et al. | |
| 2015/0191719 A1 | 7/2015 | Hudson et al. | |
| 2015/0225732 A1 | 8/2015 | Williams et al. | |
| 2015/0344549 A1 | 12/2015 | Muir et al. | |
| 2016/0024529 A1 | 1/2016 | Carstens et al. | |
| 2016/0053272 A1 | 2/2016 | Wurzel et al. | |
| 2016/0053304 A1 | 2/2016 | Wurzel et al. | |
| 2016/0076093 A1 | 3/2016 | Shendure et al. | |

(Continued)

FOREIGN PATENT DOCUMENTS

EP  2395087  12/2011
EP  3199632  8/2017

(Continued)

OTHER PUBLICATIONS

Hubmann et al., "Natural and Modified Promoters for Tailored Metabolic Engineering of the Yeast *Saccharomyces cerevisiae*" 1152 Methods in Molecular Biology (Year: 2014).*
Bao, et al., "Genome-scale engineering of *Saccharomyces cerevisiae* with single-nucleotide precision", Nature Biotechnology, doi:10.1038/nbt.4132, pp. 1-6 (May 7, 2018).
Dicarlo, et al., "Genome engineering in *Saccharomyces cervisiae* using CRISPR-Case systems", Nucleic Acids Research, 41(7):4336-43 (2013).
Garst, et al., "Genome-wide mapping of mutations at single-nucleotide resolution for protein, metabolic and genome engineering", Nature Biotechnology, 35(1):48-59 (2017).
Hsu, et al., "DNA targeting specificity of RNA-guided Cas9 nucleases", Nature Biotechnology, 31(9):827-32 (2013).
Jiang, et al., "RNA-guided editing of bacterial genomes using CRISPR-Cas systems", Nature Biotechnology, 31(3):233-41 (2013).

(Continued)

*Primary Examiner* — Nancy J Leith
(74) *Attorney, Agent, or Firm* — Sarah Brashears

(57) ABSTRACT

The present disclosure provides compositions of matter, methods and instruments for editing nucleic acids in live yeast cells.

20 Claims, 31 Drawing Sheets

(56) References Cited

U.S. PATENT DOCUMENTS

| | | |
|---|---|---|
| 2016/0102322 A1 | 4/2016 | Ravinder et al. |
| 2016/0168592 A1 | 6/2016 | Church et al. |
| 2016/0264981 A1 | 9/2016 | Yang et al. |
| 2016/0281053 A1 | 9/2016 | Sorek et al. |
| 2016/0289673 A1 | 10/2016 | Huang et al. |
| 2016/0298134 A1 | 10/2016 | Chen et al. |
| 2016/0354487 A1 | 12/2016 | Zhang et al. |
| 2017/0002339 A1 | 1/2017 | Barrngou et al. |
| 2017/0022499 A1 | 1/2017 | Lu et al. |
| 2017/0051310 A1 | 2/2017 | Doudna et al. |
| 2017/0073705 A1 | 3/2017 | Chen et al. |
| 2017/0191123 A1 | 7/2017 | Kim et al. |
| 2017/0211078 A1 | 7/2017 | Kamineni et al. |
| 2017/0240922 A1 | 8/2017 | Gill et al. |
| 2017/0369870 A1 | 12/2017 | Gill et al. |
| 2018/0028567 A1 | 2/2018 | Li et al. |
| 2018/0052176 A1 | 2/2018 | Holt et al. |
| 2018/0073013 A1 | 3/2018 | Lorenz et al. |
| 2018/0112235 A1 | 4/2018 | Li et al. |
| 2018/0187149 A1 | 7/2018 | Ma et al. |
| 2018/0200342 A1 | 7/2018 | Bikard et al. |
| 2018/0230460 A1 | 8/2018 | Gill et al. |
| 2018/0230461 A1 | 8/2018 | Gill et al. |
| 2019/0017072 A1 | 1/2019 | Ditommaso et al. |
| 2019/0136230 A1 | 5/2019 | Sather et al. |
| 2019/0169605 A1 | 6/2019 | Masquelier et al. |
| 2019/0194650 A1 | 6/2019 | Gill et al. |
| 2019/0225928 A1 | 7/2019 | Masquelier et al. |
| 2019/0270987 A1 | 9/2019 | Masquelier et al. |
| 2020/0263197 A1 | 8/2020 | Cheng et al. |

FOREIGN PATENT DOCUMENTS

| | | |
|---|---|---|
| WO | WO2002/010183 | 2/2002 |
| WO | WO 2003/087341 | 10/2003 |
| WO | WO 2010/079430 | 7/2010 |
| WO | WO 2011/072246 | 6/2011 |
| WO | WO 2011/143124 | 11/2011 |
| WO | WO 2013/142578 | 9/2013 |
| WO | WO 2013/176772 | 11/2013 |
| WO | WO 2014/018423 | 1/2014 |
| WO | WO 2014/144495 | 9/2014 |
| WO | WO2016/110453 | 7/2016 |
| WO | WO 2016/110453 | 7/2016 |
| WO | WO 2017/053902 | 3/2017 |
| WO | WO 2017/078631 | 5/2017 |
| WO | WO 2017/083722 | 5/2017 |
| WO | WO 2017/106414 | 6/2017 |
| WO | WO2017/106414 | 6/2017 |
| WO | WO 2017/161371 | 9/2017 |
| WO | WO 2017/174329 | 10/2017 |
| WO | WO 2017/186718 | 11/2017 |
| WO | WO2017/212400 | 12/2017 |
| WO | WO 2017/216392 | 12/2017 |
| WO | WO2017/216392 | 12/2017 |
| WO | WO 2017/223330 | 12/2017 |
| WO | WO2017/223330 | 12/2017 |
| WO | WO 2018/031950 | 2/2018 |
| WO | WO 2018/071672 | 4/2018 |
| WO | WO 2018/083339 | 5/2018 |
| WO | WO 2018/191715 | 10/2018 |
| WO | WO2019/006436 | 1/2019 |
| WO | WO 2019/200004 | 10/2019 |
| WO | WO2019/209926 | 10/2019 |
| WO | WO 2020/005383 | 1/2020 |
| WO | WO2020/021045 | 1/2020 |

OTHER PUBLICATIONS

Jinek, et al., "A Programmable Dual-RNA-Guided DNA Endonuclease in Adaptive Bacterial Immunity", Science, 337:816-20 (2012).

Verwaal, et al., "CRISPR/Cpfl enables fast and simple genome editing of Saccharamyces cerevisiae", Yeast, 35:201-11 (2018).

Lian, et al., "Combinatorial metabolic engineering using an orthogonal tri-functional CRISPR system", Nature Communications, DOI:1038/s41467-017-01695-x/www.nature.com/naturecommunications, pp. 1-9 (2017).

Roy, et cl., "Multiplexed precision genome editing with trackable genomic barcodes in yeast", Nature Biotechnolgy, doi:10.1038/nbt.4137, pp. 1-16 (2018).

Dong, "Establishment of a highly efficient virus-inducible CRISPR/Cas9 system in insect cells," Antiviral Res., 130:50-7(2016).

Epinat et al., "A novel engineered meganuclease induces homologous recombination in eukaryotic cells, e.g., yeast and mammalian cells", Nucleic Acids Research, 31(11): 2952-2962, 2003.

Farasat et al., "A Biophysical Model of CRISPR/Cas9 Activity for Rational Design of Genome Editing and Gene Regulation," PLoS Comput Biol., 29:12(1):e1004724 (2016).

Liu et al., "A chemical-inducible CRISPR-Cas9 system for rapid control of genome editing", Nature Chemical Biology, 12:980-987(2016).

Eklund, et al., "Altered target site specificity variants of the I-Ppol His-Cys bis homing endonuclease" Nucleic Acids Research, 35(17):5839-50 (2007).

Boles, et al., "Digital-to-biological converter for on-demand production of biologies", Nature Biotechnology, doi:10.1038/nbt.3859 (May 29, 2017).

Pines, et al., "Codon Compression Algorithms for Saturation Mutagenesis", ACS Synthetic Biology, 4:604-14 (2015).

Bessa et al., "Improved gap repair cloning in yeast: treatment of the gapped vector with Taq DNA polymerase avoids vector self-ligation," Yeast, 29(10):419-23 (2012).

Boch, "TALEs of genome targeting," Nature Biotechnology vol. 29, pp. 135-136 (2011).

Campbell et al., "Targeting protein function: the expanding toolkit for conditional disruption," Biochem J., 473(17):2573-2589 (2016).

Casini et al., "Bricks and blueprints: methods and standards for DNA assembly," Nat Rev Mol Cell Biol., (9):568-76 (2015).

Chica et al., "Semi-rational approaches to engineering enzyme activity: combining the benefits of directed evolution and rational design," Current Opinion in Biotechnology, 16(4): 378-384 (2005).

Durai et al., "Zinc finger nucleases: custom-designed molecular scissors for genome engineering of plant and mammalian cells", Nucleic Acids Res., 33(18):5978-90 (2005).

Kadonaga et al., "Regulation of RNA polymerase II transcription by sequence-specific DNA binding factors", Cell, 116(2):247-57 (2004).

Lee et al., "Targeted chromosomal deletions in human cells using zinc finger nucleases", Genome Res., 20 (1): 81-9 (2009).

Miller et al., "A TALE nuclease architecture for efficient genome editing", Nature Biotechnology, 29 (2): 143-8 (2011).

Mittelman et al., "Zinc-finger directed double-strand breaks within CAG repeat tracts promote repeat instability in human cells", PNAS USA, 106 (24): 9607-12 (2009).

Shivange, "Advances in generating functional diversity for directed protein evolution", Current Opinion in Chemical Biology, 13 (1): 19-25 (2009).

Udo, "An Alternative Method to Facilitate cDNA Cloning for Expression Studies in Mammalian Cells by Introducing Positive Blue White Selection in Vaccinia Topoisomerase I-Mediated Recombination," PLoS One, 10(9):e0139349 (2015).

Urnov et al., "Genome editing with engineered zinc finger nucleases", Nature Reviews Genetics, 11:636-646 (2010).

International Search Report and Written Opinion for International Application No. PCT/US2018/053608, dated Dec. 13, 2018, p. 1-9.

International Search Report and Written Opinion for International Application No. PCT/US2018/053670, dated Jan. 3, 2019, p. 1-13.

International Search Report and Written Opinion for International Application No. PCT/US2018/053671, dated Sep. 26, 2018, p. 1-12.

International Search Report and Written Opinion for International Application No. PCT/US2018/040519, dated Sep. 26, 2018, p. 1-8.

International Search Report and Written Opinion for International Application No. PCT/US2019/026836, dated Jul. 2, 2019, p. 1-10.

International Search Report and Written Opinion for International Application No. PCT/US2019/023342, dated Jun. 6, 2019, p. 1-34.

International Search Report and Written Opinion for International Application No. PCT/US2019/030085, dated Jul. 23, 2019, p. 1-14.

(56) References Cited

OTHER PUBLICATIONS

International Search Report and Written Opinion for International Application No. PCT/US20/24341, dated Jun. 19, 2020, p. 1-9.
NonFinal Office Action for U.S. Appl. No. 16/399,988, dated Jul. 31, 2019, p. 1-20.
First Office Action Interview Pilot Program Pre-Interview Communication for U.S. Appl. No. 16/024,831, dated Feb. 12, 2019, p. 1-37.
NonFinal Office Action for U.S. Appl. No. 16/024,816 dated Sep. 4, 2018, p. 1-10.
Final Office Action for U.S. Appl. No. 16/024,816 dated Nov. 26, 2018, p. 1-12.
First Office Action Interview Pilot Program Pre-Interview Communication Preinterview for U.S. Appl. No. 16/454,865 dated Aug. 16, 2019, p. 1-36.
Yoshioka, et al., "Development of a mono-promoter-driven CRISPR/Cas9 system in mammalian cells", Scientific Reports, Jul. 3, 2015, p. 1-8.
Remaut, et al., "Plasmid vectors for high-efficiency expression controlled by the PL promoter of coliphage lambda," Laboratory of Molecular Biology, Apr. 15, 1981, p. 81-93.
International Search Report and Written Opinion for International Application No. PCT/US2019/028821, dated Aug. 2, 2019, p. 1-14.
International Search Report and Written Opinion for International Application No. PCT/US2019/028883, dated Aug. 16, 2019, p. 1-12.
International Search Report and Written Opinion for International Application No. PCT/US2019/46526, dated Dec. 18, 2019, p. 1-17.
International Search Report and Written Opinion for International Application No. PCT/US2018/34779, dated Nov. 26, 2018, p. 1-39.
International Search Report and Written Opinion for International Application No. PCT/US19/57250, dated Feb. 25, 2020, p. 1-16.
International Search Report and Written Opinion for International Application No. PCT/US19/47135, dated Jun. 11, 2020, p. 1-15.
International Search Report and Written Opinion for International Application No. PCT/US20/19379, dated Jul. 22, 2020, p. 1-10.
International Search Report and Written Opinion for International Application No. PCT/US20/36064, dated Sep. 18, 2020, p. 1-16.
International Search Report and Written Opinion for International Application No. PCT/US20/40389, dated Oct. 13, 2020, p. 1-12.
Arnak, et al., "Yeast Artificial Chromosomes", John Wiley & Sons, Ltd., doi:10.1002/9780470015902.a0000379.pub3, pp. 1-10 (2012).
Woo, et al., "Dual roles of yeast Rad51 N-terminal domain in repairing DNA double-strand breaks", Nucleic Acids Research, doi:10.1093/nar/gkaa.587, vol. 48, No. 15, pp. 8474-8489 (2020).
International Search Report and Written Opinion for International Application No. PCT/US2021/012868, dated Mar. 26, 2021, p. 1-15.
Anzalone et al., "Search-and-replace genome editing without doubles-strand breaks or donor DNA," Nature, Oct. 21, 2019, vol. 576, No. 7785, pp. 149-157.
Alvarez, et al., "In vivo diversification of target genomic sites using processive T7 RNA polymerase-base deaminase fusions blocked by RNA-guided dCas9", Dept.of Microbial Biotechnology and Systems Biology Program, Madrid, Spain, Jan. 1, 2019, p. 1-33.
International Search Report and Written Opinion for International Application No. PCT/US20/65168, dated Mar. 17, 2021, p. 1-15.
International Search Report and Written Opinion for International Application No. PCT/US2020/038345, dated Nov. 23, 2020, p. 1-13.
International Search Report and Written Opinion for International Application No. PCT/US21/12867, dated May 12, 2021, p. 1-17.
International Search Report and Written Opinion for International Application No. PCT/US2020/064727, dated Apr. 28, 2021, p. 1-13.
International Search Report and Written Opinion for International Application No. PCT/US21/29008, dated Aug. 24, 2021, p. 1-19.
International Search Report and Written Opinion for International Application No. PCT/US21/29011, dated Aug. 24, 2021, p. 1-20.
Bauer, et al., "Cell-microcarrier Adhesion to Gas-Liquid Interfaces and Foam", Biotechnol. Prog. 2000, 16, 125-132, Oct. 19, 1999.
Datlinger, et al., "Pooled CRISPR screening with single-cell transcriptome readout", Nature Methods, Jan. 10, 2017; p. 1-10, doi:10.1038/nmeth.4177.
Dixit, et al., "Perturb-Seq: Dissecting Molecular Circuits with Scalable Single-Cell RNA Profiling of Pooled Genetic Screens", Cell 167, p. 1853-1866, Dec. 15, 2016.
GE Healthcare Life Sciences, "Microcarrier Cell Culture Principles and Methods", 18-1140-62 AC, p. 1-23, Nov. 2013.
Jacobi, et al., "Simplified CRISPR tools for efficient genome editing and streamlined protocols for their delivery into mammalian cells and mouse zygotes", Methods 121-122, p. 16-28, Mar. 23, 2017.
Jaitin, et al., "Dissecting Immune Circuits by Linking CRISPR-Pooled Screens with Single-Cell RNA-Seq", Cell 167, p. 1883-1896, Dec. 15, 2016.
Kim, et al., "Formation of Thermoresponsive Poly(N-isopropylacrylamide)/Dextran Particles by Atom Transfer Radical Polymerization", Macromol. Rapid Commun., 24, p. 517-521, 2003.
Kimple, et al., "Overview of Affinity Tags for Protein Purification", Curr Protoc Protein Sci.; 73: Unit-9-9. Doi:10.1002/0471140864.ps0909s73, p. 1-26, Aug. 6, 2015.
Nienow, et al., "A potentially scalable method for the harvesting of hMSCs from microcarriers", Biochemical Engineering Journal 85, p. 79-88, Feb. 4, 2014.
Replogle, et al., "Direct capture of CRISPR guides enables scalable, multiplexed, and multi-omic Perturb-Seq", bioRxiv; doi:http://dx.doi.org/10.1101/503367, p. 1-26, Dec. 21, 2018.
Sivalingam, et al., "Superior Red Blood Cell Generation from Human Pluripotent Stem Cells Through a Novel Microcarrier-Based Embryoid Body Platform", Tissue Engineering: Part C, vol. 22, No. 8, p. 765-780, Jun. 9, 2016.

\* cited by examiner

| Cassette 1 gene edited | Cassette 1 Fraction Edited | Cassette 2 gene edited | Cassette 2 Fraction Edited | Cassette 3 gene edited | Cassette 3 Fraction Edited | Summed fraction edited | Fraction cells with > 1 edits |
|---|---|---|---|---|---|---|---|
| YNR036C | 1.0 | YPR013C | 0.16 | #NA | #NA | 1.16 | 0.16 |
| YDR380W | 1.0 | YLR441C | 0.46 | #NA | #NA | 1.46 | 0.46 |
| YPL227C | 0.80 | YGL252C | 0.33 | #NA | #NA | 1.13 | 0.13 |
| YKL027W | 1.0 | YDR004W | 0.53 | #NA | #NA | 1.53 | 0.53 |
| YLR028C | 1.0 | YGR135W | 0.64 | #NA | #NA | 1.64 | 0.64 |
| YER104W | 1.0 | YOR137C | 0.11 | #NA | #NA | 1.11 | 0.11 |
| YMR158W-B | 0.99 | YNL235C | 0.80 | #NA | #NA | 1.80 | 0.80 |
| YKR046C | 0.92 | YDR380W | 0.77 | #NA | #NA | 1.69 | 0.69 |
| YHR137W | 0.51 | YNL167C | 0.43 | YEL068C | 0.13 | 1.07 | 0.07 |

FIG. 14

SIMULTANEOUS MULTIPLEX GENOME EDITING IN YEAST

RELATED CASES

The present application is a continuation of U.S. Ser. No. 17/230,241, filed 14 Apr. 2021, now allowed, which is a continuation of U.S. Ser. No. 17/061,143, filed 1 Oct. 2020, now U.S. Pat. No. 11,001,831; which is a continuation-in-part of U.S. Ser. No. 16/827,639, filed 23 Mar. 2020, now U.S. Pat. No. 10,815,467; which claims priority to U.S. Ser. No. 62/823,136, filed 25 Mar. 2019; U.S. Ser. No. 62/871,879, filed 9 Jul. 2019; and U.S. Ser. No. 62/960,291, filed 13 Jan. 2020.

FIELD OF THE INVENTION

This invention relates to compositions of matter, methods and instruments for nucleic acid-guided nuclease editing of live yeast cells.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the methods referenced herein do not constitute prior art under the applicable statutory provisions.

The ability to make precise, targeted changes to the genome of living cells has been a long-standing goal in biomedical research and development. Recently various nucleases have been identified that allow manipulation of gene sequence, and hence gene function. The nucleases include nucleic acid-guided nucleases, which enable researchers to generate permanent edits in live cells. Editing efficiencies frequently correlate with the level of expression of guide RNA s (gRNAs) in the cell, That is, the higher the expression level of gRNA, the better the editing efficiency. Moreover, editing efficiencies in eukaryotes also correlate with the gRNAs being localized in the nucleus; that is, for efficient editing to occur, the gRNAs must remain in the nucleus to direct editing, rather than being exported from the nucleus to the cytoplasm. Additionally, it is desirable to minimize the number of editing rounds yet obtain a high number of edits in a cellular genome; however, the architecture of many current editing systems only allows one edit per round There is thus a need in the art of nucleic acid-guided nuclease gene editing for improved methods for increased transcription and nuclear localization of gRNAs, as well as methods and compositions for simultaneous combinatorial editing. The present invention satisfies this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present disclosure relates to methods and compositions for making several edits to a yeast genome simultaneously, as well as modules and automated multi-module cell processing instruments configured to perform the methods utilizing the compositions.

In yeast, such as *Saccharomyces cerevisiae* (*S. cerevisiae*), gRNA expression systems can use RNA polymerase III (pol III) or RNA polymerase II (pol II) promoters to drive transcription. The available number of pol III promoters in yeast is limited as compared to pol II promoters. In general, pol III promoters have lower expression levels than pol II promoters and pol II promoters are more tolerant to sequence variations than are pol III promoters, which allows for increased sequence flexibility. In a multiplexed gene editing system, the expression level of gRNAs is a critical factor in editing efficiency and efficacy. Pol II promoters generally express gRNAs that are subsequently polyadenylated, marking the transcript for nuclear export; however, in order to use pol II gRNA expression in a gene editing system, gRNAs expressed from the pol II promoter must remain in the nucleus. To accomplish gRNA nuclear localization after expression from a pol II promoter, a self-cleaving ribozyme is added to the 3' end of the gRNA transcript. This self-cleaving ribozyme cleaves off the poly-A nuclear export tag. In some embodiments, a self-cleaving ribozyme is also added 5' of the transcript to cleave off the post-transcriptionally added 5' cap, which also, when present, helps mediate nuclear export of mRNA.

Thus, in one embodiment there is provided a ribozyme-containing editing cassette for performing RNA-directed nuclease editing in yeast comprising from 5' to 3': a pol II promoter, a transcription start site, a coding sequence for a gRNA, a coding sequence for a donor DNA, a coding sequence for a self-cleaving ribozyme, and a pol II terminator; or a pol II promoter, a transcription start site, a coding sequence for a donor DNA, a coding sequence for a gRNA, a coding sequence for a self-cleaving ribozyme, and a pol II terminator. That is, the ribozyme-containing editing cassettes of the present invention are agnostic to the order of the gRNA and donor DNA coding sequences in the ribozyme-containing editing cassette.

In addition, in preferred aspects the ribozyme-containing editing cassettes comprise regions of homology to a vector backbone for gap-repair insert of the ribozyme-containing editing cassettes into the vector backbone.

Further, in some aspects, the ribozyme-containing editing cassette further comprises a second self-cleaving ribozyme 3' of the transcription start site.

In some aspects of this embodiment, the self-cleaving ribozyme of the ribozyme-containing editing cassette is selected from a self-cleaving ribozyme in a hepatitis delta virus (HDV)-like ribozyme family, a self-cleaving ribozyme in a glucosamine-6-phosphate synthase ribozyme family, a self-cleaving ribozyme in a hammerhead ribozyme family, a self-cleaving ribozyme in a hairpin ribozyme family, a self-cleaving ribozyme in a *Neurospora* Varkud satellite ribozyme family, a self-cleaving ribozyme in a twister ribozyme family, a self-cleaving ribozyme in a twister sister ribozyme family, a self-cleaving ribozyme in a hatchet ribozyme family, or a self-cleaving ribozyme in a pistol ribozyme family. Additionally, in some aspects of this embodiment, there is a second self-cleaving ribozyme sequence located 3' of the transcription start site and 5' of the first coding sequence for a nucleic acids-guided editing component (e.g., either the gRNA or donor DNA) of the editing cassette.

Also, in some embodiments, the pol II promoter of the composition is a cell-type specific promoter, a tissue-specific promoter, or a synthetic promoter. In some aspects, the pol II promoter is a constitutive fungal promoter, and in some aspects, the constitutive fungal pol II promoter is selected from a pPGK1, pTDH3, pENO2, pADH1, pTPI1, pTEF1, pTEF2, pYEF3, pRPL3, pRPL15A, pRPL4, pRPL8B, pSSA1, pSSB1, or pPDA1 promoter. In yet other aspects, the pol II promoter may be a constitutive mammalian promoter, such as the pCMV, pEF1a, pSV40, pPGK1, pUbc, human beta actin promoter, or pCAG promoter. Alternatively, the pol II promoter may be an inducible promoter, such as the PHO5 promoter, the MET3 promoter, the CUP1 promoter, the GAL1 promoter, or the GEV or LEV promoter system.

Yet other embodiments provide a method for RNA-directed nuclease editing in yeast cells comprising the steps of: designing and synthesizing ribozyme-containing editing cassettes, wherein the ribozyme-containing editing cassettes comprise from 5' to 3': 1) a pol II promoter, a transcription start site, a coding sequence for a gRNA, a coding sequence for a donor DNA, a coding sequence for a self-cleaving ribozyme, and a pol II terminator, or 2) a pol II promoter, a transcription start site, a coding sequence for a donor DNA, a coding sequence for a gRNA, a coding sequence for a self-cleaving ribozyme, and a pol II terminator; amplifying the synthesized ribozyme-containing editing cassettes; transforming the yeast cells with the ribozyme-containing editing cassettes and vector backbone; selecting for transformed yeast cells; providing conditions for RNA-directed nuclease editing; and using the edited yeast cells in research.

In some aspects of the method, after the second providing step (e.g., providing conditions for RNA-directed nuclease editing), a second selecting step is performed thereby selecting for edited cells; and in some aspects of the methods, the designing, amplifying, first providing, transforming, first selecting, second providing and second selecting steps are repeated until a desired number of edits have been made to the yeast cells.

In other embodiments there is provided a dual ribozyme-containing editing cassette for performing RNA-directed nuclease editing in yeast comprising from 5' to 3': a pol II promoter; a transcription start site; a first editing cassette, wherein the editing cassette comprises a coding sequence for a first gRNA and a coding sequence for a first donor DNA, and wherein the first donor DNA comprises a rational, desired edit to a first target sequence and an edit configured to render inactive a proto-spacer motif (PAM) in the first target sequence; a linker or spacer (not to be confused with a proto-spacer motif (PAM)); a second editing cassette (e.g., here a ribozyme-containing editing cassette), wherein the second editing cassette comprises a coding sequence for a second gRNA and a coding sequence for a second donor DNA, wherein the second donor DNA comprises a rational, desired edit to a second target sequence and an edit configured to render inactive a proto-spacer motif (PAM) in the second target sequence, a coding sequence for a self-cleaving ribozyme, and a pol II terminator.

In some aspects, the dual ribozyme-containing editing cassette further comprises a second self-cleaving ribozyme 3' of the transcription start site. In some aspects, the linker or spacer is a coding sequence for a tRNA whereas in other aspects, the linker or spacer is a primer sequence. In some embodiments, the ribozyme-containing editing cassette further comprises between the second editing cassette and the coding sequence for a self-cleaving ribozyme a second linker or spacer and a third editing cassette, wherein the third editing cassette comprises a coding sequence for a third gRNA and a coding sequence for a third donor DNA, and wherein the third donor DNA comprises a rational, desired edit to a third target sequence and an edit configured to render inactive a proto-spacer motif (PAM) in the third target sequence thus resulting in a multiplex ribozyme-containing editing cassette. In some aspects, a multiplex ribozyme-containing editing cassette may comprise a fourth, fifth and even sixth editing cassette where each of the fourth, fifth and sixth editing cassettes are separated from the other editing cassettes by a linker or spacer.

In some aspects, the coding sequence for the first gRNA is 5' of the coding sequence of the first donor DNA, whereas in other aspects, the coding sequence for the first gRNA is 3' of the coding sequence of the first donor DNA. In some aspects, the coding sequence for the second gRNA is 5' of the coding sequence of the second donor DNA, whereas in other aspects, the coding sequence for the second gRNA is 3' of the coding sequence of the second donor DNA. Again, the ribozyme-containing editing cassettes (and editing cassettes) of the present invention are agnostic to the order of the gRNA and donor DNA coding sequences in the ribozyme-containing editing cassette.

In yet another embodiment there is provided a library of linear vector backbones and a library of the editing cassettes or the ribozyme-containing editing cassettes to be transformed into yeast cells comprising: a first linear vector backbone comprising a coding sequence for a nuclease, a coding sequence for a first antibiotic resistance gene, and a 2μ origin of replication; and a library of editing cassettes or ribozyme-containing editing cassettes, wherein the gRNAs and donor DNAs of different editing cassettes or ribozyme-containing editing cassettes in the library target different target regions in a yeast genome, and wherein homology exists between the library of editing cassettes or ribozyme-containing editing cassettes and the first linear vector.

In some aspects, there is also provided a library of linear vector backbones and a library of editing cassettes or ribozyme-containing editing cassettes to be transformed into yeast cells comprising: a first linear vector backbone comprising a coding sequence for a nuclease, a coding sequence for a first antibiotic gene, and a 2μ origin of replication; a second linear vector backbone comprising a coding sequence for the nuclease, a coding sequence for a second antibiotic resistance gene, and a 2μ origin of replication; and a library of editing cassettes or the ribozyme-containing editing cassettes, wherein the gRNAs and donor DNAs of different editing cassettes or ribozyme-containing editing cassettes in the library target different target regions in a yeast genome, and wherein homology exists between the library of editing cassettes or ribozyme-containing editing cassettes and the first and second linear vectors.

In some aspects of this embodiment, the library of linear vector backbones further comprises a third linear vector backbone comprising a coding sequence for the nuclease, a coding sequence for a third antibiotic resistance gene, and a 2μ origin of replication; and in some aspects, the library of linear vector backbones further comprises a fourth linear vector backbone comprising a coding sequence for the nuclease, a coding sequence for a fourth antibiotic resistance gene, and a 2μ origin of replication and even a fifth linear vector backbone comprising a coding sequence for the nuclease, a coding sequence for a fifth antibiotic resistance gene, and a 2μ origin of replication. In some aspects, the coding sequence for the nuclease in each of the first, second, third, fourth and fifth linear vectors is the same coding sequence, however in other aspects, the coding sequence for the nuclease in each of the first, second, third, fourth and fifth linear vectors may be a different coding sequence.

In some aspects, the first antibiotic resistance gene confers resistance to hygromycin and the second antibiotic resistance gene confers resistance to G418.

In some aspects, each editing cassette or ribozyme-containing editing cassette comprises two gRNAs and two donor DNAs, or three gRNAs and three donor DNAs.

In some aspects, each linear vector backbone comprises a promoter positioned to drive transcription of the editing cassette such as a pol II promoter, and in some aspects each linear vector backbone further comprises an origin of replication functional in bacteria. That is, in some aspects the promoter driving transcription of the editing cassette is on the vector backbone rather than including in the editing cassette or ribozyme-containing editing cassette.

Other embodiments provide a method of performing nucleic acid guided nuclease editing in yeast cells comprising the steps of: 1) transforming yeast cells with a library of linear vector backbones and a library of editing cassettes or ribozyme-containing editing cassettes to be transformed into yeast cells wherein the library of linear vector backbones comprises: a first linear vector backbone comprising a coding sequence for a nuclease, a coding sequence for a first antibiotic resistance gene, and a 2µ origin of replication; a second linear vector backbone comprising a coding sequence for the nuclease, a coding sequence for a second antibiotic resistance gene, and a 2µ origin of replication; and a library of editing cassettes or ribozyme-containing editing cassettes, wherein each editing cassette comprises a gRNA and a donor DNA, wherein the gRNAs and donor DNAs of different cassettes target different target regions in a yeast genome, and wherein homology exists between the library of editing cassettes and the first and second linear vectors; 2) selecting for yeast cells resistant to the first and second antibiotic resistance genes; 3) allowing the yeast cells to recover and for the nucleic acid-guided nuclease editing to take place; and 4) growing the edited yeast cells to stationary phase. Once the yeast cells have been grown to stationary phase, the cells can then be pooled and rendered electrocompetent for another round of editing. In some aspects of this embodiment, the yeast cells may be singulated after the transformation step.

Yet another embodiment provides a library of linear vector backbones and a library of editing cassettes or ribozyme-containing editing cassettes to be transformed into yeast cells comprising: a first linear vector backbone comprising a coding sequence for a nuclease, a coding sequence for a first antibiotic resistance gene, and a 2µ origin of replication; and a second linear vector backbone comprising a coding sequence for the nuclease, a coding sequence for a second antibiotic resistance gene, and a 2µ origin of replication; and a library of editing cassettes or ribozyme-containing editing cassettes, wherein each editing cassette or ribozyme-containing editing cassette comprises a gRNA and a donor DNA, wherein the gRNAs and donor DNAs of different editing cassettes or ribozyme-containing editing cassettes target different target regions in a yeast genome, and wherein homology exists between the library of editing cassettes or ribozyme-containing editing cassette and the linear vector backbones.

In other embodiments there is provided a composition of matter comprising libraries of linear vector backbones and libraries of editing cassettes to be transformed into yeast cells comprising: a first linear vector backbone library comprising a coding sequence for a nuclease, a coding sequence for a first antibiotic resistance gene, first homology regions for inserting a first library of editing cassettes, and a 2µ origin of replication; a second linear vector backbone library comprising a coding sequence for a nuclease, a coding sequence for a second antibiotic resistance gene, second homology regions for inserting a second library of editing cassettes, and a 2µ origin of replication; the first library of editing cassettes, wherein each editing cassette comprises a gRNA and a donor DNA, wherein the gRNAs and donor DNAs of different cassettes target different target regions in a yeast genome, and wherein homology exists between the first library of editing cassettes and the first linear vector library; and the second library of editing cassettes, wherein each editing cassette comprises a gRNA and a donor DNA, wherein the gRNAs and donor DNAs of different cassettes target different target regions in a yeast genome, and wherein homology exists between the second library of editing cassettes and the second linear vector library.

In some aspects of this embodiment, the composition of matter further comprises a third linear vector backbone library comprising a coding sequence for a nuclease, third homology regions for inserting a third library of editing cassettes, a coding sequence for a third antibiotic resistance gene, and a 2µ origin of replication; and the third library of editing cassettes, wherein each editing cassette comprises a gRNA and a donor DNA, wherein the gRNAs and donor DNAs of different cassettes target different target regions in a yeast genome, and wherein homology exists between the third library of editing cassettes and the third linear vector library. In some aspects, the composition further comprises a fourth linear vector backbone library comprising a coding sequence for a nuclease, fourth homology regions for inserting a fourth library of editing cassettes, a coding sequence for a fourth antibiotic resistance gene, and a 2µ origin of replication; and the fourth library of editing cassettes, wherein each editing cassette comprises a gRNA and a donor DNA, wherein the gRNAs and donor DNAs of different cassettes target different target regions in a yeast genome, and wherein homology exists between the fourth library of editing cassettes and the fourth linear vector library.

Yet another embodiment provides a composition of matter comprising libraries of linear vector backbones and libraries of editing cassettes to be transformed into yeast cells comprising: a first linear vector backbone library comprising a coding sequence for a nuclease, a coding sequence for a first portion of a first antibiotic resistance gene fused to an N-terminus of a first intein, first homology regions for inserting a first library of editing cassettes, and a 2µ origin of replication; a second linear vector backbone library comprising a coding sequence for a nuclease, a coding sequence for a second portion of a first antibiotic resistance gene fused to an C-terminus of the first intein, second homology regions for inserting a second library of editing cassettes, and a 2µ origin of replication; the first library of editing cassettes, wherein each editing cassette comprises a gRNA and a donor DNA, wherein the gRNAs and donor DNAs of different cassettes target different target regions in a yeast genome, and wherein homology exists between the first library of editing cassettes and the first linear vector library; and the second library of editing cassettes, wherein each editing cassette comprises a gRNA and a donor DNA, wherein the gRNAs and donor DNAs of different cassettes target different target regions in a yeast genome, and wherein homology exists between the second library of editing cassettes and the second linear vector library.

In some aspects of this embodiment the composition of matter of claim further comprises a third linear vector backbone library comprising a coding sequence for a nuclease, third homology regions for inserting a third library of editing cassettes, a coding sequence for a first portion of a second antibiotic resistance gene fused to the N-terminus of a second intein, and a 2μ origin of replication; a fourth linear vector backbone library comprising a coding sequence for a nuclease, fourth homology regions for inserting a fourth library of editing cassettes, a coding sequence for a second portion of a second antibiotic resistance gene fused to a C-terminus of the second intein, and a 2μ origin of replication; the third library of editing cassettes, wherein each editing cassette comprises a gRNA and a donor DNA, wherein the gRNAs and donor DNAs of different cassettes target different target regions in a yeast genome, and wherein homology exists between the third library of editing cassettes and the third linear vector library; and the fourth library of editing cassettes, wherein each editing cassette comprises a gRNA and a donor DNA, wherein the gRNAs and donor DNAs of different cassettes target different target regions in a yeast genome, and wherein homology exists between the fourth library of editing cassettes and the fourth linear vector library.

In some aspects of this embodiment, the first intein is derived from *Nostoc punctiforme* PCC73102 split alpha subunit of the DNA polymerase III intein (NpuDnaE), *Synechocystis* sp. PCC6803 DnaB helicase SspDnaB, or CfaDnaE (a consensus alignment of Npu and Ssp).

In some aspects of these embodiments of compositions, the first and second antibiotic resistance genes confer resistance to hygromycin, G418, puromycin, blasticidin or nourseothricin and the first and second antibiotic resistance genes are different.

In some aspects of these embodiments of compositions, each editing cassette of each library of editing cassettes comprises two gRNAs and two donor DNAs, and in some aspects, each editing cassette of each library of editing cassettes comprises three gRNAs and three donor DNAs.

In some aspects of these compositions, each linear vector backbone in each linear backbone library further comprises a promoter driving expression of the editing cassette, and in some aspects the promoter is a pol II promoter.

In some aspects of these embodiments of compositions, wherein each linear vector backbone in each linear backbone library further comprises an origin of replication functional in bacteria.

These aspects and other features and advantages of the invention are described below in more detail.

BRIEF DESCRIPTION OF THE DRAWINGS

The foregoing and other features and advantages of the present invention will be more fully understood from the following detailed description of illustrative embodiments taken in conjunction with the accompanying drawings in which:

FIG. 14 shows the results from using a single vector backbone and editing cassette library to simultaneously edit multiple loci in the genome of *S. cerevisiae*.

It should be understood that the drawings are not necessarily to scale, and that like reference numbers refer to like features.

DETAILED DESCRIPTION

Figure 1A:
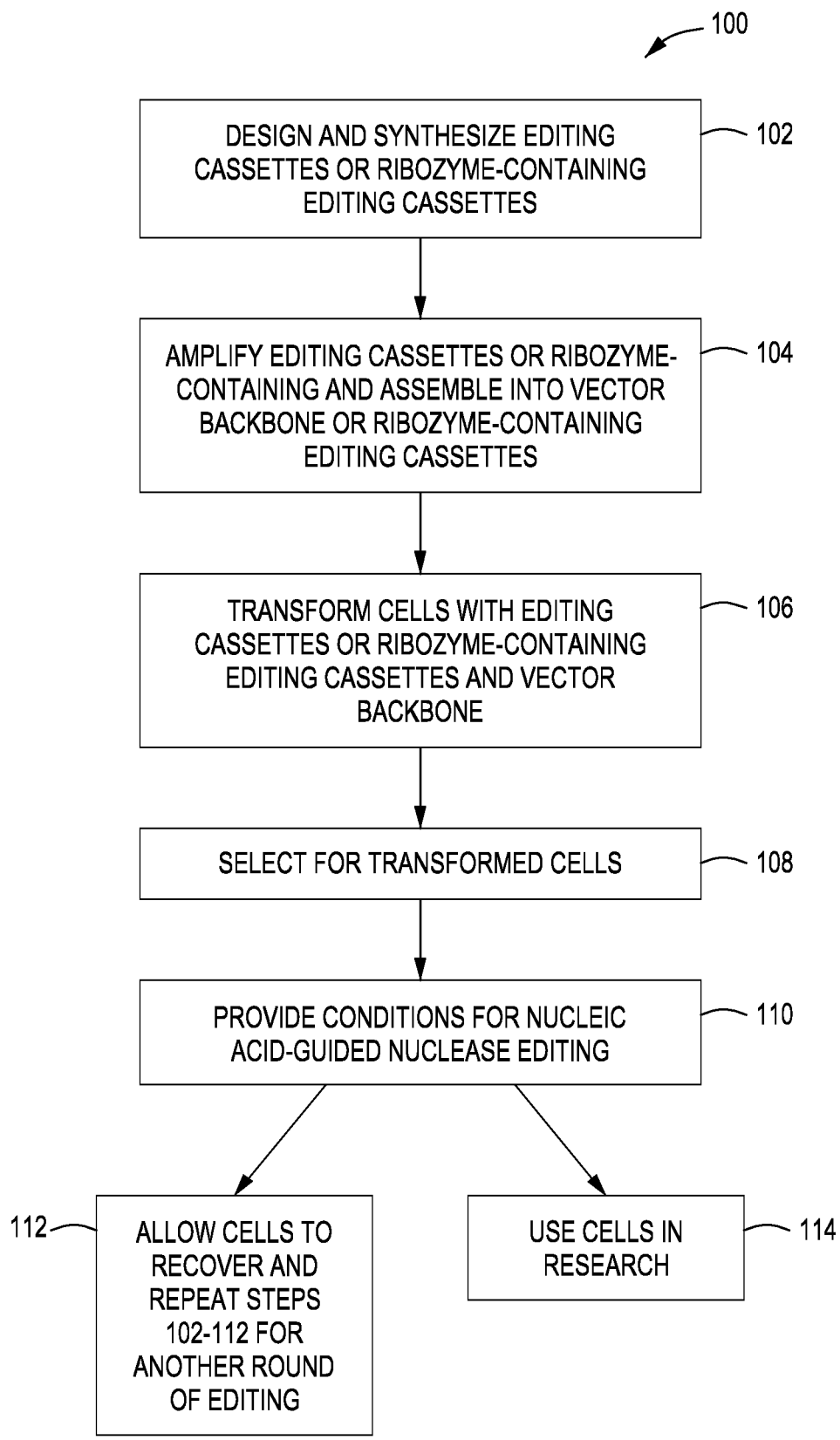
FIG. 1A is a simplified block diagram of an exemplary method for editing live yeast cells via nucleic acid-guided nuclease editing.

All of the functionalities described in connection with one embodiment are intended to be applicable to the additional embodiments described herein except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

The practice of the techniques described herein may employ, unless otherwise indicated, conventional techniques and descriptions of organic chemistry, polymer technology, molecular biology (including recombinant techniques), cell biology, biochemistry and sequencing technology, which are within the skill of those who practice in the art. Such conventional techniques include polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds. (1999), *Genome Analysis: A Laboratory Manual Series* (Vols. I-IV); Weiner, Gabriel, Stephens, Eds. (2007), *Genetic Variation: A Laboratory Manual*; Dieffenbach, Dveksler, Eds. (2003), *PCR Primer: A Laboratory Manual*; Bowtell and Sambrook (2003), *DNA Microarrays: A Molecular Cloning Manual*; Mount (2004), *Bioinformatics: Sequence and Genome Analysis*; Sambrook and Russell (2006), *Condensed Protocols from Molecular Cloning: A Laboratory Manual*; and Sambrook and Russell (2002), *Molecular Cloning: A Laboratory Manual* (all from Cold Spring Harbor Laboratory Press); Stryer, L. (1995) *Biochemistry* (4th Ed.) W. H. Freeman, New York N.Y.; Gait, "*Oligonucleotide Synthesis: A Practical Approach*" 1984, IRL Press, London; Nelson and Cox (2000), *Lehninger, Principles of Biochemistry* $3^{rd}$ Ed., W. H. Freeman Pub., New York, N.Y.; Berg et al. (2002) *Biochemistry*, $5^{th}$ Ed., W.H. Freeman Pub., New York, N.Y.; all of which are herein incorporated in their entirety by reference for all purposes. CRISPR-specific techniques can be found in, e.g., *Genome Editing and Engineering from TALENs and CRISPRs to Molecular Surgery*, Appasani and Church (2018); and *CRISPR: Methods and Protocols*, Lindgren and Charpentier (2015); both of which are herein incorporated in their entirety by reference for all purposes.

Note that as used herein and in the appended claims, the singular forms "a," "an," and "the" include plural referents unless the context clearly dictates otherwise. Thus, for example, reference to "an oligonucleotide" refers to one or more oligonucleotides, and reference to "an automated system" includes reference to equivalent steps and methods for use with the system known to those skilled in the art, and so forth. Additionally, it is to be understood that terms such as "left," "right," "top," "bottom," "front," "rear," "side," "height," "length," "width," "upper," "lower," "interior," "exterior," "inner," "outer" that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, methods and cell populations that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

In the following description, numerous specific details are set forth to provide a more thorough understanding of the present invention. However, it will be apparent to one of ordinary skill in the art that the present invention may be practiced without one or more of these specific details. In other instances, well-known features and procedures well known to those skilled in the art have not been described in order to avoid obscuring the invention.

The term "complementary" as used herein refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" or "percent homology" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'; and the nucleotide sequence 3'-TCGA-5' is 100% complementary to a region of the nucleotide sequence 5'-TAGCTG-3'.

The term DNA "control sequences" refers collectively to promoter sequences, polyadenylation signals, transcription termination sequences, upstream regulatory domains, origins of replication, internal ribosome entry sites, nuclear localization sequences, enhancers, and the like, which collectively provide for the replication, transcription and translation of a coding sequence in a recipient cell. Not all of these types of control sequences need to be present so long as a selected coding sequence is capable of being replicated, transcribed and—for some components—translated in an appropriate host cell.

As used herein the term "donor DNA" or "donor nucleic acid" or "homology arm" refers to nucleic acid that is designed to introduce a DNA sequence modification (insertion, deletion, substitution) into a locus by homologous recombination using nucleic acid-guided nucleases. For homology-directed repair, the donor DNA must have sufficient homology to the regions flanking the "cut site" or site to be edited in the genomic target sequence. The length of the homology arm(s) will depend on, e.g., the type and size of the modification being made. In many instances and preferably, the donor DNA will have two regions of sequence homology (e.g., two homology arms) to the genomic target locus. Preferably, an "insert" region or "DNA sequence modification" region—the nucleic acid modification that one desires to be introduced into a genome target locus in a cell—will be located between two regions of homology. The DNA sequence modification may change one or more bases of the target genomic DNA sequence at one specific site or multiple specific sites. A change may include changing 1, 2, 3, 4, 5, 10, 15, 20, 25, 30, 35, 40, 50, 75, 100, 150, 200, 300, 400, or 500 or more base pairs of the target sequence. A deletion or insertion may be a deletion or insertion of 1, 2, 3, 4, 5, 10, 15, 20, 25, 30, 40, 50, 75, 100, 150, 200, 300, 400, or 500 or more base pairs of the target sequence.

The term "editing cassette" refers to a nucleic acid molecule comprising a coding sequence for transcription of a guide nucleic acid or gRNA covalently linked to a coding sequence for transcription of a donor DNA or homology arm. The term "ribozyme-containing editing cassette" refers to a nucleic acid molecule comprising an editing cassette and at least one self-cleaving ribozyme.

The terms "guide nucleic acid" or "guide RNA" or "gRNA" refer to a polynucleotide comprising 1) a guide sequence capable of hybridizing to a genomic target locus, and 2) a scaffold sequence capable of interacting or complexing with a nucleic acid-guided nuclease.

"Homology" or "identity" or "similarity" refers to sequence similarity between two peptides or, more often in the context of the present disclosure, between two nucleic acid molecules. The term "homologous region" or "homology arm" refers to a region on the donor DNA with a certain degree of homology with the target genomic DNA sequence. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

"Nucleic acid-guided editing components" refers to one, some, or all of a nuclease, a guide nucleic acid, a donor nucleic acid, and recombination systems, if required.

"Operably linked" refers to an arrangement of elements where the components so described are configured so as to perform their usual function. Thus, control sequences operably linked to a coding sequence are capable of effecting the transcription, and in some cases, the translation, of a coding sequence. The control sequences need not be contiguous with the coding sequence so long as they function to direct the expression of the coding sequence. Thus, for example, intervening untranslated yet transcribed sequences can be present between a promoter sequence and the coding sequence and the promoter sequence can still be considered "operably linked" to the coding sequence. In fact, such sequences need not reside on the same contiguous DNA molecule (i.e. chromosome) and may still have interactions resulting in altered regulation.

A "PAM mutation" refers to one or more edits to a target sequence that removes, mutates, or otherwise renders inactive a PAM or spacer region in the target sequence.

A "promoter" or "promoter sequence" is a DNA regulatory region capable of binding RNA polymerase and initiating transcription of a polynucleotide or polypeptide coding sequence such as messenger RNA, ribosomal RNA, small nuclear or nucleolar RNA, guide RNA, or any kind of RNA. Promoters may be constitutive or inducible. A "pol II promoter" is a regulatory sequence that is bound by RNA polymerase II to catalyze the transcription of DNA.

As used herein, a "ribozyme" (ribonucleic acid enzyme) is an RNA molecule capable of catalyzing biochemical reactions. A "self-cleaving ribozyme" is a ribozyme capable of cleaving itself.

As used herein the term "selectable marker" refers to a gene introduced into a cell, which confers a trait suitable for artificial selection. General use selectable markers are well-known to those of ordinary skill in the art. Drug selectable markers such as ampicillin/carbenicillin, kanamycin, chloramphenicol, nourseothricin N-acetyl transferase, erythromycin, tetracycline, gentamicin, bleomycin, streptomycin, puromycin, hygromycin, blasticidin, and G418 may be employed. In other embodiments, selectable markers include, but are not limited to human nerve growth factor receptor (detected with a MAb, such as described in U.S. Pat. No. 6,365,373); truncated human growth factor receptor (detected with MAb); mutant human dihydrofolate reductase (DHFR; fluorescent MTX substrate available); secreted alkaline phosphatase (SEAP; fluorescent substrate available); human thymidylate synthase (TS; confers resistance to anti-cancer agent fluorodeoxyuridine); human glutathione S-transferase alpha (GSTA1; conjugates glutathione to the stem cell selective alkylator busulfan; chemoprotective selectable marker in CD34+ cells); CD24 cell surface antigen in hematopoietic stem cells; human CAD gene to confer resistance to N-phosphonacetyl-L-aspartate (PALA); human multi-drug resistance-1 (MDR-1; P-glycoprotein surface protein selectable by increased drug resistance or enriched by FACS); human CD25 (IL-2a; detectable by Mab-FITC); Methylguanine-DNA methyltransferase (MGMT; selectable by carmustine); rhamnose; and Cytidine deaminase (CD; selectable by Ara-C). "Selective medium" as used herein refers to cell growth medium to which has been added a chemical compound or biological moiety that selects for or against selectable markers.

The terms "target genomic DNA sequence", "target sequence", or "genomic target locus" refer to any locus in vitro or in vivo, or in a nucleic acid (e.g., genome or episome) of a cell or population of cells, in which a change of at least one nucleotide is desired using a nucleic acid-guided nuclease editing system. The target sequence can be a genomic locus or extrachromosomal locus.

A "vector" is any of a variety of nucleic acids that comprise a desired sequence or sequences to be delivered to and/or expressed in a cell. Vectors are typically composed of DNA, although RNA vectors are also available. Vectors include, but are not limited to, plasmids, fosmids, phagemids, virus genomes, BACs, YACs, PACs, synthetic chromosomes, and the like.

Improved Nucleic Acid-Guided Nuclease Editing in Yeast

The present disclosure provides compositions of matter, methods and instruments for nucleic acid-guided nuclease editing of live yeast cells, and in particular, high-throughput methods for increasing editing rates and allowing for multiplex simultaneous editing in live yeast cells. The compositions and methods described herein improve CRISPR editing systems in which nucleic acid-guided nucleases (e.g., RNA-guided nucleases) are used to edit specific target regions in a yeast genome. A nucleic acid-guided nuclease complexed with an appropriate synthetic guide nucleic acid in a yeast cell can cut the genome of the cell at a desired location. The guide nucleic acid helps the nucleic acid-guided nuclease recognize and cut the DNA at a specific target sequence. By manipulating the nucleotide sequence of the guide nucleic acid, the nucleic acid-guided nuclease may be programmed to target any DNA sequence for cleavage as long as an appropriate protospacer adjacent motif (PAM) is nearby.

A guide nucleic acid comprises a guide sequence, where the guide sequence is a polynucleotide sequence having sufficient complementarity with a target sequence to hybridize with the target sequence and direct sequence-specific binding of a complexed nucleic acid-guided nuclease to the target sequence. The degree of complementarity between a guide sequence and the corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences. In some embodiments, a guide sequence is about or more than about 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20 nucleotides in length. Preferably the guide sequence is 10-30 or 15-20 nucleotides long, or 15, 16, 17, 18, 19, or 20 nucleotides in length. The guide nucleic acid also comprises a scaffold sequence capable of interacting or complexing with a nucleic acid-guided nuclease.

Another component of the nucleic acid-guided nuclease system is the donor nucleic acid or homology arm. The donor nucleic acid is on the same polynucleotide (e.g., editing cassette or ribozyme-containing editing cassette) as the guide nucleic acid and typically is under the control of the same promoter as the guide nucleic acid (e.g., a single promoter driving the transcription of both the guide nucleic acid and the donor nucleic acid) (see, e.g., FIGS. 1B, 1C and 1H). The donor nucleic acid is designed to serve as a template for homologous recombination with a target sequence nicked or cleaved by the nucleic acid-guided nuclease as a part of the gRNA/nuclease complex. A donor nucleic acid polynucleotide may be of any suitable length, such as about or more than about 20, 25, 50, 75, 100, 150, 200, 500, or 1000 nucleotides in length. In certain preferred aspects, the donor nucleic acid can be provided as an oligonucleotide of between 20-300 nucleotides, more preferably between 50-250 nucleotides. The donor nucleic acid comprises a region that is complementary to a portion of the target sequence (e.g., a homology arm). When optimally aligned, the donor nucleic acid overlaps with (is complementary to) the target sequence by, e.g., about 20, 25, 30, 35, 40, 50, 60, 70, 80, 90 or more nucleotides. In many embodiments and preferably, the donor nucleic acid comprises two homology arms (regions complementary to the target sequence) flanking the mutation or difference between the donor nucleic acid and the target template. The donor nucleic acid comprises at least one mutation or alteration compared to the target sequence, such as an insertion, deletion, modification, or any combination thereof compared to the target sequence.

The donor nucleic acid is provided—along with the gRNA (both scaffold and guide sequences)—as one component in an editing cassette or ribozyme-containing editing cassette, where the editing cassette or ribozyme-containing editing cassette may be one of multiple editing cassettes inserted into a vector backbone. That is, there may be more than one, e.g., two, three, four, five or more individual gRNA/donor DNA pairs inserted into a vector backbone, where the multiple guide nucleic acid/donor nucleic acid pairs are under the control of a single promoter—in some embodiments, a pol II promoter, and in some embodiments, the promoter driving transcription of the gRNAs is an inducible pol II promoter. In some embodiments, transcription of the nuclease is also inducible; thus, in some embodiments, transcription of both the nuclease and gRNA are inducible. Inducible editing is advantageous in that cells can be grown for several to many cell doublings to a stationary growth phase (or nearly so) before editing is initiated, which increases the likelihood that cells with edits will survive. In some aspects, there are linker or spacer sequences separating the individual gRNA/donor DNA pairs from one another.

The guide nucleic acid can be engineered to target a desired target sequence by altering the guide sequence so that the guide sequence is complementary to a desired target sequence, thereby allowing hybridization between the guide sequence and the target sequence. In general, to generate an edit in the target sequence, the gRNA/nuclease complex binds to a target sequence as determined by the guide RNA, and the nuclease recognizes a protospacer adjacent motif PAM) sequence adjacent to the target sequence. The target sequence can be any genomic or episomal polynucleotide whether endogenous or exogenous to a prokaryotic or eukaryotic cell, or in vitro. For example, the target sequence can be a polynucleotide residing in the nucleus of a yeast cell. A target sequence can be a sequence encoding a gene product (e.g., a protein) or a non-coding sequence (e.g., a regulatory polynucleotide, an intron, a PAM, a spacer, or "junk" DNA).

The target sequence is associated with a protospacer adjacent motif (PAM), which is a short nucleotide sequence recognized by the gRNA/nuclease complex. The precise PAM sequence and length requirements for different nucleic acid-guided nucleases vary; however, PAMs typically are 2-7 base-pair sequences adjacent or in proximity to the target sequence and, depending on the nuclease, can be 5' or 3' to the target sequence. Thus, the editing cassette provides a donor DNA sequence (e.g., a homology arm) that, in addition to allowing for precise genome editing of a target sequence also provides one or more changes to the target sequence that removes, mutates or renders inactive the proto-spacer adjacent motif (PAM) in the target sequence. Rendering the PAM at the target sequence inactive precludes additional editing of the cell genome at that target sequence, e.g., upon subsequent exposure to a nucleic acid-guided nuclease complexed with a synthetic guide nucleic acid in later rounds of editing. Thus, cells having the desired target sequence edit and an altered PAM can be selected using a nucleic acid-guided nuclease complexed with a synthetic guide nucleic acid complementary to the target sequence. Cells that did not undergo the first editing event will be cut rendering a double-stranded DNA break, and thus will not continue to be viable. The cells containing the desired target sequence edit and PAM alteration will not be cut, as these edited cells no longer contain the necessary PAM site and will continue to grow and propagate.

Methods and compositions for designing and synthesizing editing cassettes are described in U.S. Pat. Nos. 10,240,167; 10,266,849; 9,982,278; 10,351,877; 10,364,442; and 10,435,715; and U.S. Ser. No. 16/275,465, filed 14 Feb. 2019, all of which are incorporated by reference herein. Again, each editing cassette and ribozyme-containing editing cassette comprises a gRNA sequence to be transcribed and a donor DNA or homology arm sequence to be transcribed, including both a desired edit and a PAM or spacer mutation. In the case of ribozyme-containing editing cassettes, at least one editing cassette is linked to a coding sequence for one or more self-cleaving ribozymes. Note that although the gRNA is shown 5' to the donor DNA in FIGS. 1B and 1C, the gRNA could be positioned 3' of the donor DNA.

In certain of the present methods and compositions, the polynucleotide sequence encoding the editing cassette is linked to one or more self-cleaving ribozyme sequences creating a ribozyme-containing editing cassette. The ribozyme sequence may be 20-200 nucleotides in length, more preferably 50-150 nucleotides in length. When transcribed to RNA, self-cleaving ribozyme sequences mediate site-specific phosphodiester cleavage of the transcript within or proximal to the ribozyme sequence itself. Cleavage proceeds via general acid-general base catalysis, beginning with abstraction of a proton from the 2' OH of the nucleotide 5' of the scissile bond. The resulting 2' oxygen attacks the adjacent 3' phosphate, yielding a 2'-3' cyclic phosphate in the upstream nucleotide and a 5'-hydroxyl product downstream of the scissile bond.

Ribozymes mediate sequence-specific cleavage of the internal phosphodiester bond by means of their unique secondary and tertiary structure that organize after transcription to RNA, including multihelical junctions, interactions of nonhelical elements such as helix-terminal loops and internal bulges, and pseudoknotting. These tertiary structures position the substrate—the scissile bond to be cleaved—inside an active-site cleft surrounded by nucleotides that may be distant in the primary sequence. There are several families of ribozymes, each with unique structure and active site conformation, but they all accomplish the same reaction of sequence-specific phosphodiester cleavage. In the present methods and compositions, the self-cleaving ribozyme sequence may be chosen from one of hepatitis delta virus (HDV)-like, glucosamine-6-phosphate synthase (glmS), Neuropsora Varkud satellite (VS), hammerhead, twister, twister sister, hatchet, pistol, among others.

In some embodiments, the ribozyme sequence may be placed 3' of the homology arm of the editing cassette and 5' of the pol II terminator sequence (discussed below and shown in FIG. 1B), i.e. between the homology arm and the pol II terminator sequence. In native contexts, the pol II terminator sequence typically coordinates termination and polyadenylation, followed by nuclear export. In preferred embodiments of the present disclosure the ribozyme sequence mediates cleavage of the poly(A) tail from the 3' end of the transcript and prevents nuclear export of the pol II-transcribed gRNA transcript. In some embodiments, two different self-cleaving ribozymes may be used with one ribozyme placed at the 3' end of the donor DNA or homology arm and with one ribozyme placed at the 5' end of the editing cassette, 3' of the transcription start site. The 5' ribozyme removes the post-transcriptionally-added 5' cap, thus further increasing the likelihood the cassette transcript will be retained within the nucleus.

In a one embodiment, one ribozyme is HDV-like and the HDV-like ribozyme is placed 3' of the homology arm or homology arms of the gRNA/donor DNA pair and 5' of the pol II terminator sequence, i.e., between the homology arm and the pol II terminator sequence. The HDV-like ribozyme mediates cleavage 5' of the ribozyme sequence itself, minimizing the amount of HDV-like sequence remaining on the cleaved transcript. Also, in one embodiment, a hammerhead ribozyme is used 5' of the editing cassette and 3' of the promoter. Although here the choice of self-cleaving ribozymes to be positioned 3' of the transcription start site and positioned 3' of the editing cassette are hammerhead and HDV-like respectively, other arrangements can be used; for example, the self-cleaving ribozyme positioned 3' of the transcription start site and 5' of the editing cassette may be an HDV-like ribozyme and the self-cleaving ribozyme positioned 3' of the editing cassette and 5' of the pol II terminator sequence may be a hammerhead ribozyme. Alternatively, both self-cleaving ribozymes may be the same self-cleaving ribozyme such as two hammerhead ribozymes, though this configuration is not preferred due to concerns of secondary structure formation and/or recombination between sites. In yet another alternative, any self-cleaving ribozyme may be used in either position, including—in addition to the HDV-like and hammerhead ribozymes—glucosamine-6-phosphate synthase (glmS) ribozymes, Neuropsora Varkud satellite (VS) ribozymes, twister ribozymes, twister sister ribozymes, hatchet ribozymes, and pistol ribozymes.

The ribonucleoprotein editing complex performs editing of its target sequence in the nucleus; thus, the gRNA transcript must remain in the nucleus for editing to occur. In certain embodiments of the present methods and compositions, the guide nucleic acid and donor DNA are provided as coding sequences in an editing cassette to be expressed from a plasmid or vector under the control of a pol II promoter. Previously, RNAs transcribed by an RNA pol II promoter could not be used as gRNAs, as they undergo significant post-transcriptional processing and nuclear export. Therefore, RNA polymerase III promoters, e.g. U6, U3, U2, SNR52, RPR1, among others, have been used in the art to drive expression of gRNAs. Pol III-expressed RNAs are not polyadenylated or exported from the nucleus. However, pol III promoters have several limitations. First, in the yeast genome for example, there are relatively few pol III promoters available and they are generally lower-expressing than pol II promoters, limiting the dynamic range and expression levels available for gRNAs. Second, pol III promoters are not amenable to sequence alteration, e.g., the U6 promoter requires a guanine nucleotide at its transcription initiation site, limiting gRNA target sequence selection. Additionally, pol III promoters are restrictive in that many of pol III promoters have intragenic regulatory regions, such that changing the sequence to be expressed is not possible.

Also, pol III genes are generally housekeeping genes and are constitutively and ubiquitously expressed, precluding the use of inducible, cell-type, or tissue-specific promoters for gRNA expression. Finally, because the donor DNA sequences (e.g., homology arm sequences) are typically derived from genomic sequences, the donor DNA sequences may contain pol III termination motifs such as Penta T or Penta T+G. Termination motifs such as these may prevent transcription of the functional gRNA portion of the editing cassettes.

In contrast, RNA pol II promoters are generally higher expressing and provide a much larger dynamic range of possible expression levels of gRNA compared to the limited number of pol III promoters. Pol II promoters are more amenable to sequence alteration and do not have the limited sequence requirements of pol III promoters, thereby expanding the editing space and flexibility of target sequences. Expressing gRNAs with pol II enables the use of the many cell-type specific, tissue specific, or synthetic pol II promoters that have been designed, including inducible promoters, discussed below.

In some embodiments, the pol II promoter driving gRNA expression may be selected from one of many constitutive fungal promoters, including but not limited to, pPGK1, pTDH3, pENO2, pADH1, pTPI1, pTEF1, pTEF2, pYEF3, pRPL3, pRPL15A, pRPL4, pRPL8B, pSSA1, pSSB1, or pPDA1. As discussed above, pol II promoters have a wide dynamic range of expression levels. In a preferred embodiment, gRNA expression may be driven by a pol II promoter known to drive relatively high expression levels in yeast, e.g. pPGK1, pTDH3, pADH1, pENO2. In another embodiment gRNA expression may be driven by a pol II promoter known to drive mid-range expression levels in yeast, e.g. pTEF1, pTEF2, pYEF3, pRPL3, pRPL15A. In yet another embodiment, gRNA expression may be drive by a pol II promoter known to drive relatively low expression levels in yeast, e.g. pRPL4, pSSB1, pSSA1, pPDA1, pCYC1. In other embodiments, the pol II promoter driving gRNA expression may be selected from one of many constitutive promoters driving expression in mammalian cells, including but not limited to, pCMV, pEF1a, pSV40, pPGK1, pUbc, human beta actin promoter, pCAG, among others.

As for the nuclease component of the nucleic acid-guided nuclease editing system, a polynucleotide sequence encoding the nucleic acid-guided nuclease can be codon optimized for expression in particular cells, such as archaeal, prokaryotic or eukaryotic cells. Eukaryotic cells can be yeast, fungi, algae, plant, animal, or human cells. Eukaryotic cells may be those of or derived from a particular organism, such as a mammal, including but not limited to human, mouse, rat, rabbit, dog, or non-human mammals including non-human primates. The choice of nucleic acid-guided nuclease to be employed depends on many factors, such as what type of edit is to be made in the target sequence and whether an appropriate PAM is located close to the desired target sequence. Nucleases of use in the methods described herein include but are not limited to Cas 9, Cas 12a (e.g., CpfI), MAD2, or MAD7. As with the guide nucleic acid, the nuclease may be encoded by a DNA sequence on a vector (e.g., the engine vector) and may be under the control of an inducible promoter.

In addition to the components described above, an editing cassette or ribozyme-containing editing cassette may comprise one or more primer sites. The primer sites can be used to amplify the editing cassettes or ribozyme-containing editing cassettes and to assemble multiplexed editing cassettes or ribozyme-containing editing cassettes by using oligonucleotide primers and bridging oligos; for example, if the primer sites flank one or more of the other components of the editing cassette.

An editing cassette or ribozyme-containing editing cassette also may comprise a barcode. A barcode is a unique DNA sequence that corresponds to the donor DNA sequence such that the barcode can identify the edit made to the corresponding target sequence. The barcode typically comprises four or more nucleotides. In some embodiments, the editing cassettes or ribozyme-containing editing cassettes comprise a collection of donor nucleic acids representing, e.g., gene-wide or genome-wide libraries of donor nucleic acids. The library of editing cassettes or ribozyme-containing editing cassettes is assembled into multiplex editing cassettes of at least two gRNA/donor DNA pairs and then cloned into vector backbones where, e.g., each different donor nucleic acid is associated with a different barcode.

Additionally, in some embodiments, a vector encoding components of the nucleic acid-guided nuclease system further encodes a nucleic acid-guided nuclease comprising one or more nuclear localization sequences (NLSs), such as about or more than about 1, 2, 3, 4, 5, 6, 7, 8, 9, 10, or more NLSs. In some embodiments, the engineered nuclease comprises NLSs at or near the amino-terminus, NLSs at or near the carboxy-terminus, or a combination.

The editing cassettes, ribozyme-containing editing cassettes, and/or vector backbones comprise control sequences operably linked to the component sequences to be transcribed. As stated above, the pol II promoters driving transcription of one or more components of the nucleic acid-guided nuclease editing system (e.g., transcription of one or both of the nuclease and gRNA) may be inducible. A number of gene regulation control systems have been developed for the controlled expression of genes in plant, microbe, and animal cells, including mammalian cells, for example the pL promoter (induced by heat inactivation of the CI857 repressor), the pBAD promoter (induced by the addition of arabinose to the cell growth medium), and the rhamnose inducible promoter (induced by the addition of rhamnose to the cell growth medium). Yeast inducible promoters may be responsive to nutrient source, small molecule, hormone response elements, nutrient depletion, or synthetic compounds. Yeast inducible promoter systems may include the PHO5 promoter, inducible by depletion of inorganic phosphate (U.S. Pat. No. 4,880,734); the MET3 promoter, suppressed by depletion of methionine (Mao, et al., Current Microbiology, 45:37-40 (2002)); the CUP1 promoter, inducible by copper (U.S. Pat. No. 4,940,661); the GAL1 promoter, inducible by galactose and suppressed by glucose (U.S. Pat. No. 5,139,936); or the GEV and ZEV systems, engineered promoters responsive to estradiol induction (U.S. Pat. No. 9,212,359), among others.

Figure 1B:
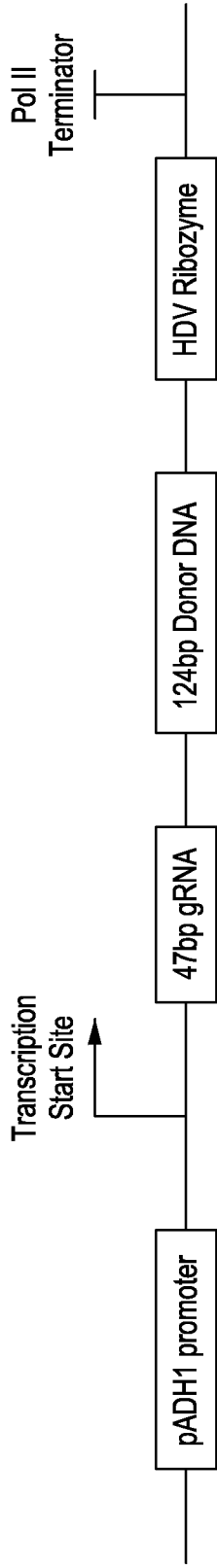
FIG. 1B is a graphic depiction of an exemplary embodiment of a ribozyme-containing editing cassette for nucleic acid-guided nuclease editing.

FIG. 1A shows a simplified flow chart for exemplary method 100 for enriching for edited cells. Looking at FIG. 1A, method 100 begins by designing and synthesizing editing cassettes or ribozyme-containing editing cassettes 102. As described above, each editing cassette or ribozyme-containing editing cassette comprises a gRNA sequence to be transcribed and a donor DNA sequence (e.g., homology arm sequence) to be transcribed comprising a desired target genome edits as well as a PAM or spacer mutation. In or ribozyme-containing editing cassettes, the editing cassette is linked to one or more sequences coding for a self-cleaving ribozyme. Once the editing cassettes or ribozyme-containing editing cassettes have been synthesized, the individual editing cassettes are amplified 104. The editing cassettes or ribozyme-containing editing cassettes and linear vector backbones are then used to transform cells 106 thereby creating a library of transformed cells. The vector backbones typically comprise the coding sequence for a nuclease, as seen in FIG. 1F. Alternatively, the cells may already be expressing the nuclease (e.g., the cells may have already been transformed with a vector comprising the coding sequence for the nuclease or the coding sequence for the nuclease may be stably integrated into the cellular genome) such that only the vector backbone does not comprise a coding sequence for a nuclease.

A variety of delivery systems may be used to introduce (e.g., transform or transfect) nucleic acid-guided nuclease editing system components into a host cell 108. These delivery systems include the use of yeast systems, lipofection systems, microinjection systems, biolistic systems, virosomes, liposomes, immunoliposomes, polycations, lipid: nucleic acid conjugates, virions, artificial virions, viral vectors, electroporation, cell permeable peptides, nanoparticles, nanowires, exosomes. Alternatively, molecular trojan horse liposomes may be used to deliver nucleic acid-guided nuclease components across the blood brain barrier. Of particular interest is the use of electroporation, particularly flow-through electroporation (either as a stand-alone instrument or as a module in an automated multi-module system) as described in, e.g., U.S. Pat. No. 10,253,316, issued 9 Apr. 2019; U.S. Pat. No. 10,329,559, issued 25 Jun. 2019; U.S. Pat. No. 10,323,242, issued 18 Jun. 2019; U.S. Pat. No. 10,421,959, issued 24 Sep. 2019; U.S. Pat. No. 10,465,185, issued 5 Nov. 2019; U.S. Pat. No. 10,519,437, issued 31 Dec. 2019; and U.S. Ser. No. 16/666,964, filed 29 Oct. 2019, and Ser. No. 16/680,643, filed 12 Nov. 2019 all of which are herein incorporated by reference in their entirety. If the screening/selection module is one module in an automated multi-module cell editing system, the cells are likely transformed in an automated cell transformation module.

Once transformed 106, the cells can then be subjected to selection using selection medium 108. Selectable markers and selection medium are employed to select for cells that have received the vector backbone. Commonly used selectable markers include drug selectable markers such as ampicillin/carbenicillin, kanamycin, chloramphenicol, erythromycin, tetracycline, gentamicin, bleomycin, streptomycin, puromycin, hygromycin, blasticidin, and G418.

Once cells that have been properly transformed are selected 108, the next step in method 100 is to provide conditions for nucleic acid-guided nuclease editing 110. "Providing conditions" includes incubation of the cells in appropriate medium and may also include providing conditions to induce transcription of an inducible promoter (e.g., adding antibiotics, increasing temperature) for transcription of one or both of the gRNA/donor DNA pair and nuclease. Once editing is complete, the cells are allowed to recover and may be subjected to another round of editing 112 or, alternatively, the cells may be used in research 114.

In certain embodiments of the present methods and compositions, expression of the editing cassette is driven by a pol II promoter and a self-cleaving ribozyme sequence is placed 3' of the editing cassette. FIG. 1B depicts an exemplary editing cassette in the context of a pol II promoter and self-cleaving ribozyme. The pol II promoter (here, a pADH1 promoter) is 5' of the transcription start site and drives expression of the editing cassette. After the transcription start site, there is an editing cassette comprising a gRNA sequence (47 bp gRNA) that encodes both the guide RNA that is complementary to the nuclease target sequence and the gRNA scaffold sequence that complexes with the nuclease. Next, 3' of the gRNA sequence in the editing cassette is the donor DNA sequence (124 bp Donor DNA) that encodes the template for homologous recombination including the desired edit and one or more PAM site alterations. Although the gRNA sequence is shown 5' to the donor DNA in this editing cassette, the gRNA sequence may be 3' to the donor DNA sequence as both the editing cassettes and or ribozyme-containing editing cassettes are agnostic regarding the order of the gRNA and donor DNA coding sequences. Following the donor DNA sequence is an HDV ribozyme sequence that encodes the HDV-like self-cleaving ribozyme which mediates cleavage of the poly(A) tail that is the result of pol II transcription. Finally, a pol II terminator (Pol II Terminator) terminates pol II transcription of the editing cassette. Though not shown in FIG. 1B, a second self-cleaving ribozyme sequence may be included in this editing construct 3' to the transcription start site and 5' to the coding sequence for the gRNA in the editing cassette.

Figure 1C:
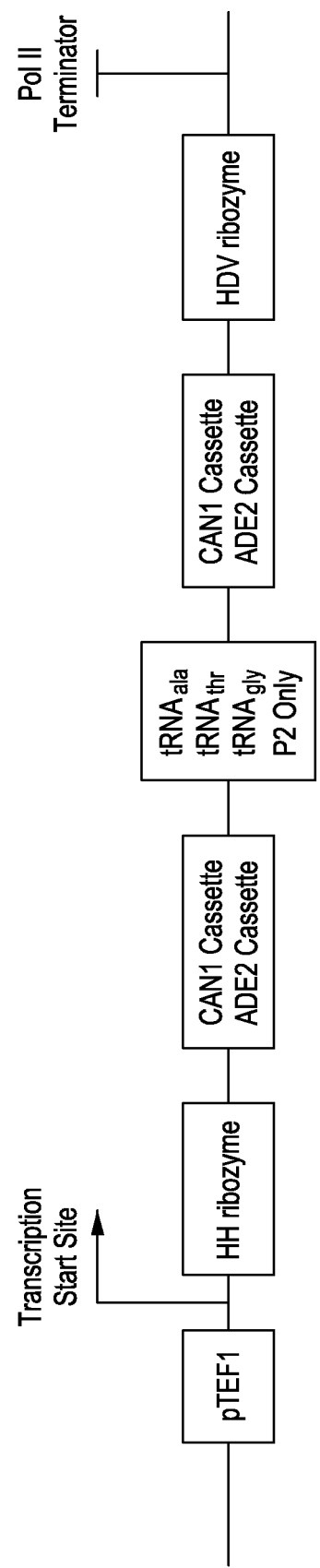
FIG. 1C is a graphic depiction of an exemplary embodiment of a dual ribozyme-containing editing cassette for nucleic acid-guided nuclease editing.

FIG. 1C is depicts a dual or ribozyme-containing editing cassette architecture for achieving simultaneous combinatorial (e.g., multiplex) editing. The compositions and methods described herein for single edits using a single or ribozyme-containing editing cassette architecture apply to multiple or ribozyme-containing editing cassette architecture. For example—as with single-edit architectures—using a pol II promoter to transcribe multiple editing cassettes avoids potential termination motifs in the donor DNAs that would create an issue for pol III transcription systems. Additionally, the present pol II system enables the use of many synthetic pol II promoters that otherwise would not be available for gRNA expression. In addition, pol II promoters are less sensitive to sequence changes than pol III promoters and enable use of a range of small molecule inducible promoters including the GAL1, GEV and ZEV systems. As with the single edit ribozyme-containing editing cassette architecture, a dual or multiple ribozyme-containing editing cassette architecture employs a 3' self-cleaving ribozyme—such as an HDV ribozyme or hammerhead ribozyme—to cleave off the post-transcriptionally added polyA tail which is a nuclear export signal, thus increasing the likelihood that the editing cassette transcript remains in the nucleus. However, in the exemplary embodiment shown in FIG. 1C, the dual or multiple-cassette architecture also employs a 5' self-cleaving ribozyme, in this case a hammerhead ribozyme, to remove the post-transcriptionally added 5' cap which also increases the likelihood that the editing cassette is retained in the nucleus.

The dual editing cassette architecture shown in FIG. 1C comprises two gRNA/donor DNA pairs, a pol II promoter and two self-cleaving ribozymes. The pol II promoter (here, the constitutive pTEF1 promoter) is 5' of the transcription start site and drives transcription of the first and second self-cleaving peptides, first and second editing cassettes and a linker or spacer sequence. After the transcription start site, there is a coding sequence for a self-cleaving ribozyme, in this case a hammerhead ribozyme. The purpose of this self-cleaving ribozyme at the 5' end of the dual ribozyme-containing editing cassette—as stated above—is to remove the post-transcriptionally added 5' cap to the dual cassette transcript which promotes retaining the editing cassettes in the nucleus. 3' to the first self-cleaving ribozyme is a gRNA sequence that encodes both the guide RNA that is complementary to the nuclease target sequence and the scaffold sequence which complexes with the nuclease. Following the first gRNA sequence in the or ribozyme-containing editing cassette there is a first donor DNA sequence (here, coding for a, e.g., CAN1 or ADE2 knockout) that 1) encodes the template for homologous recombination with the target sequence thereby directing rational, precise edits to the target sequence, and 2) provides one or more edits to the target sequence that removes, mutates, or otherwise renders inactive a PAM or spacer region in the target.

The next element in the dual ribozyme-containing editing cassette architecture is an optional linker or spacer comprising a sequence that promotes cleavage between the two editing cassettes. The linker or spacer element may comprise 1) a tRNA sequence, which assists in the processing of the separate editing cassettes by exploiting the endogenous RNA processing sequences present in tRNAs; 2) an additional self-cleaving ribozyme (such as a self-cleaving ribozyme in the hepatitis delta virus (HDV)-like ribozyme family, a self-cleaving ribozyme in the glucosamine-6-phosphate synthase ribozyme family, a self-cleaving ribozyme in the hammerhead ribozyme family, a self-cleaving ribozyme in the hairpin ribozyme family, a self-cleaving ribozyme in the *Neurospora* Varkud satellite ribozyme family, a self-cleaving ribozyme in the twister ribozyme family, a self-cleaving ribozyme in the twister sister ribozyme family, a self-cleaving ribozyme in the hatchet ribozyme family, or a self-cleaving ribozyme in the pistol ribozyme family); or 3) an exogenous cleavage factor recognition sequence (such as Cys4).

Following the linker or spacer (e.g., 3' of the linker) is the second gRNA/donor DNA pair. The second gRNA/donor DNA pair comprises a second gRNA sequence encoding the both the guide RNA that is complementary to the nuclease target sequence and the scaffold sequence which complexes with the nuclease; and a second donor DNA sequence (here, also a CAN1 or ADE2 knockout) that encodes the template for homologous recombination with the target sequence comprising both the desired edit and one or more PAM site alterations. 3' to the second gRNA/donor DNA pair is a second self-cleaving ribozyme sequence, here encoding the HDV self-cleaving ribozyme, which mediates cleavage of the poly(A) tail that is the result of pol II transcription. Finally, 3' to the HDV ribozyme sequence is a pol II terminator which functions to terminate pol II transcription of the dual editing cassette. Although in this FIG. 1C the gRNA is shown 5' to the donor DNA in the gRNA/donor DNA pairs, in either or both gRNA/donor DNA pairs the gRNA may be 3' of the donor DNA. Further, FIG. 1C shows two editing cassettes in the construct; however, there may be a third, fourth, fifth or sixth gRNA/donor DNA pair in the construct, wherein each of the a third, fourth, fifth or sixth gRNA/donor DNA pairs are separated by one another by a linker or spacer sequence.

In addition to increased transcription and nuclear localization of gRNAs, the present disclosure is drawn to increasing the efficiency of nucleic acid-guided nuclease editing in yeast via multi-vector transformations (MVTs). As described in detail above, in nucleic acid-guided nuclease genome editing, precise edits are created via homology-directed repair of nuclease-mediated double strand breaks or single-strand nicks with a gRNA/donor DNA pair located on a plasmid. The number of edits per cell is limited by the fact that, typically, only one plasmid containing one editing cassette is able to confer a single edit in the genome of each cell transformed by an editing pool. The present disclosure demonstrates that, via the gap repair assembly process and adjusting the ratio of editing cassettes to vector backbones, individual yeast cells may be transformed by multiple vector backbones at once, thereby allowing the cell to be edited simultaneously by multiple editing cassettes contained within the vector backbones. This process is referred to herein as multi-vector transformation (MVT).

Multi-vector transformation occurs as a result of the gap repair plasmid cloning process, whereby a pool of linearized vector backbones—where each vector backbone comprises an antibiotic resistance gene or a portion of an antibiotic resistance gene as described infra—is co-transformed into yeast cells with a pool of editing cassettes that contain 1) a gRNA sequence, 2) a DNA donor sequence (preferably comprising in addition to a sequence for a desired edit, a PAM mutation), and 3) sequences homologous to the linearized plasmid backbone. Through the yeast cell's native homologous recombination machinery, the linearized plasmid backbone and editing cassette are joined together into an editing plasmid, and the editing plasmid can be selected for via the antibiotic resistance gene.

MVT is a variation on the gap repair assembly process where multiple editing cassettes (or multiple ribozyme-containing editing cassettes) combine with linearized backbones (e.g., linearized backbones of the same type or linearized backbones that comprise different antibiotic resistance genes) to create more than one unique editing plasmid inside of the single yeast cell. The multiple unique editing plasmids are maintained inside the single cell simultaneously due to the presence of the 2µ viral origin located on the editing plasmid, where the 2µ viral origin of replication is the multi-copy origin, typically maintaining a copy number of roughly 50 plasmids—in this case editing plasmids—in any given cell.

Figure 1D:
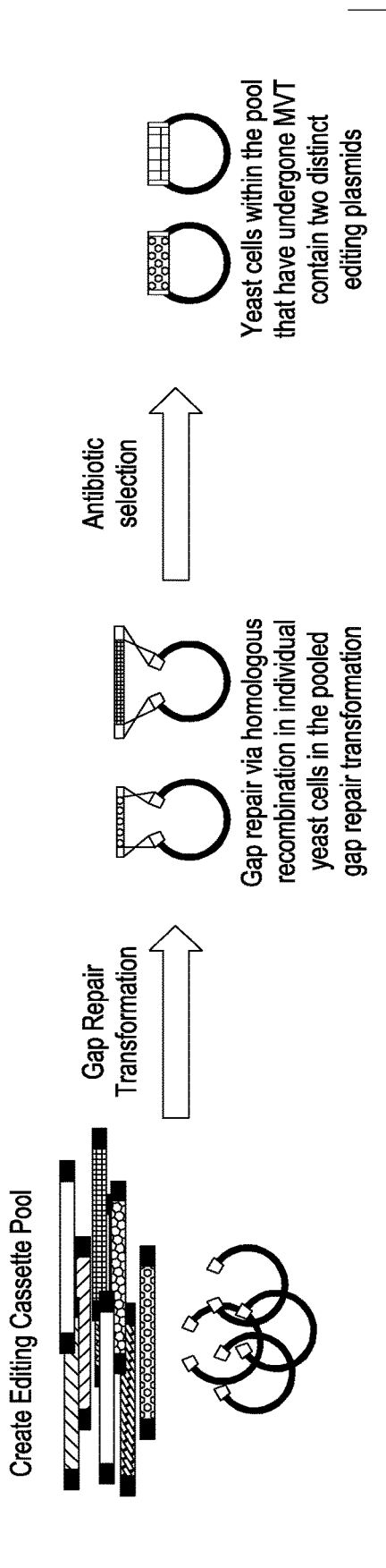
FIG. 1D is a simplified graphic of a method for editing yeast genomes using a single vector backbone and a library of editing cassettes, and adjusting the concentration of the editing cassettes in the transformation reaction to drive formation of more than one editing vector per cell to achieve two to many edits per cell per round.

Described herein are several ways in which multi-vector transformation editing can be optimized. First, by increasing the molar ratio of the editing cassette pool or ribozyme-containing editing cassette pool to the linearized vector backbone, the number of different editing vectors that are assembled via gap repair and maintained in each cell is increased. This embodiment is shown in FIG. 1D.

Figure 1E:
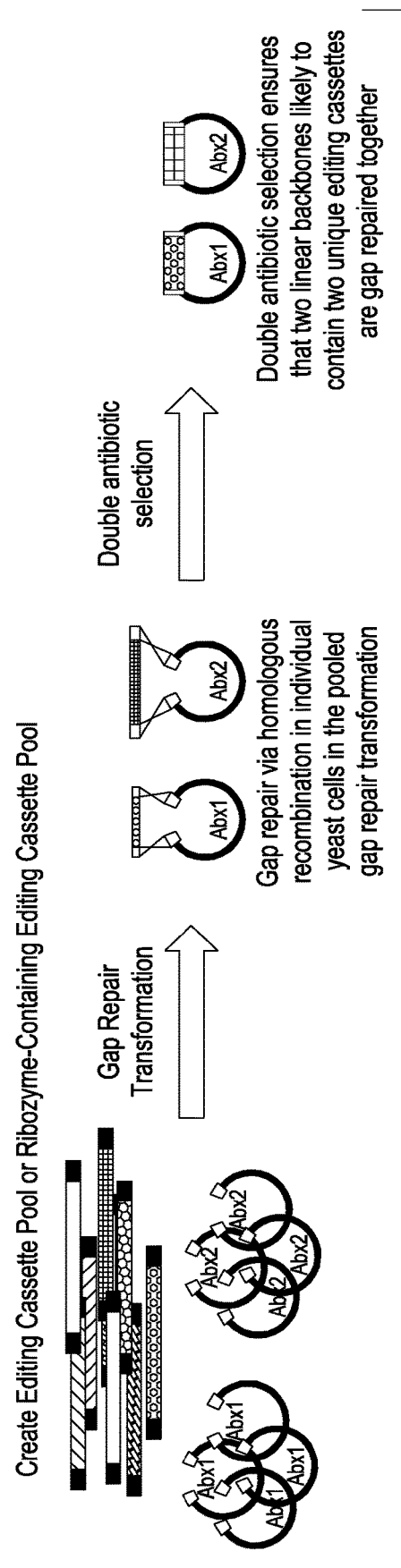
FIG. 1E is a simplified graphic of an alternative system for editing yeast genomes with two to many edits per round of editing using two different vector backbones.
Figure 1F:
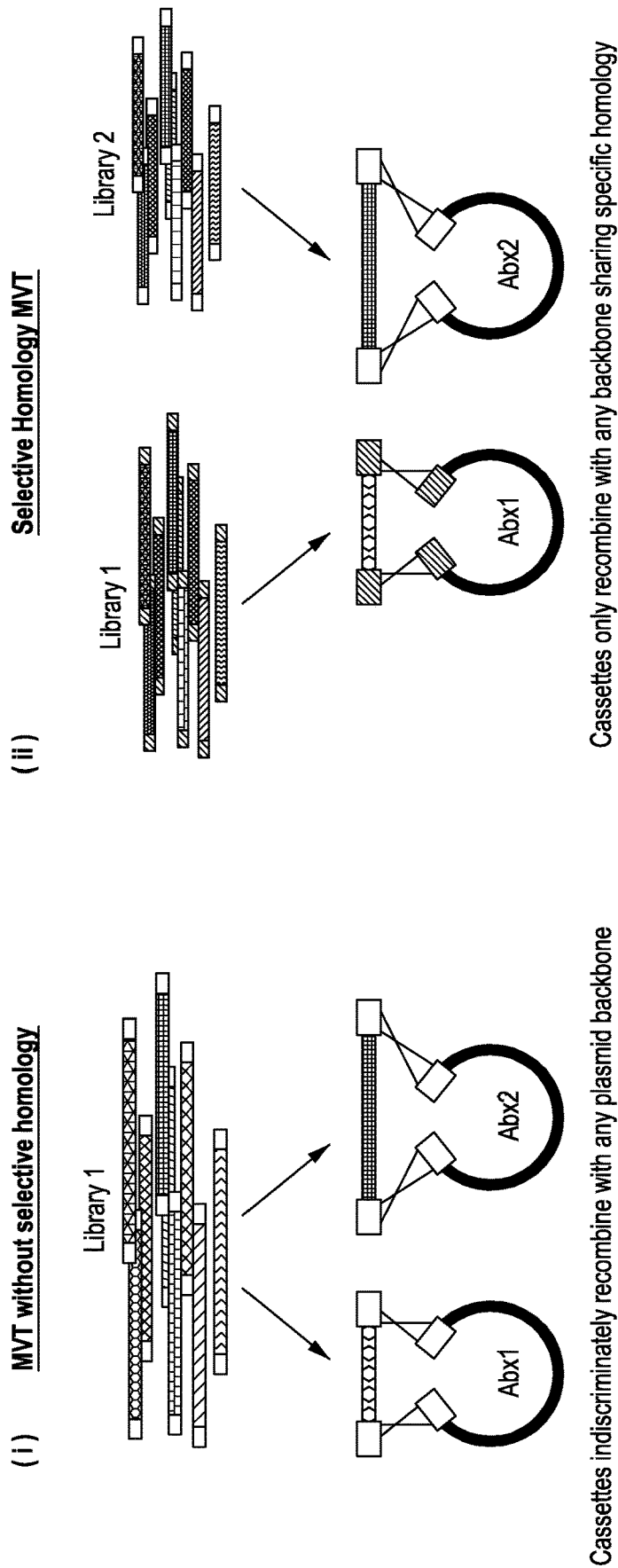
FIG. 1F (i) shows the result of multi-vector transformation without selective homology (as in the last panel of FIG. 1E) and FIG. 1F (ii) shows the result of multi-vector transformation with selective homology.

Second, the rate of MVT is increased when multiple linearized plasmid backbones with different selection genes (e.g., antibiotic resistance genes) are included in the transformation with the pool of editing cassettes or ribozyme-containing editing cassettes, followed by selection for yeast cells resistant to all antibiotic markers included on the linearized plasmid backbones. This alternative embodiment is shown in FIG. 1E. In this embodiment, only cells that have been transformed with linearized plasmid backbones with each of the selectable markers survive the selection thereby forcing multi-vector transformation. It has been determined that the probability of a unique editing cassette or ribozyme-containing editing cassette becoming incorporated via gap repair into a plasmid backbone is a function of the size of the editing cassette pool or ribozyme-containing editing cassette pool and the distribution of editing cassettes or ribozyme-containing editing cassettes within the pool. The more editing cassettes or ribozyme-containing editing cassettes in the library and the more uniform the pool of editing cassettes or ribozyme-containing editing cassettes, the higher the probability unique cassettes will be incorporated into the linearized plasmid backbones in each cell allowing for multiple edits per cell.

Third, FIG. 1F(ii) shows an alternative or expansion of the method shown in FIG. 1E. In FIG. 1F(i), the method shown in FIG. 1E is shown in abbreviated form, where a library of editing cassettes are inserted into two different vector backbones comprising different antibiotic resistance markers; however, the process of inserting the library of editing cassette into the two different vector backbones is random. In FIG. 1F(ii), the different vector backbones not only comprise different antibiotic resistance markers but also comprise different homologies for inserting the editing cassettes. That is, two different libraries of editing cassettes are used, one library of editing cassettes with regions of homology to be inserted into vector backbone A and one library of editing cassettes with regions of homology to be inserted into vector backbone B. As described in more detail infra, such a scheme can prevent "collisions" between edits.

Finally in yet another alternative to the method shown in FIG. 1E, instead of using two different antibiotic resistance genes a single antibiotic resistance gene is used, where one vector backbone codes for a first portion of the antibiotic resistance gene and a second vector backbone codes for a second portion of the antibiotic resistance gene; that is, a split antibiotic resistance gene is used. In such a system, the gene encoding an antibiotic resistance protein is split into two or more segments and fused to inteins that can be rejoined by protein trans-splicing. Each portion is carried on a vector backbone carrying an editing cassette. Delivery of the vector backbones to a population of cells results in cells that comprise a partial set of portions of the antibiotic resistance gene or a full set of portions of the antibiotic resistance genes. Only cells with a complete set of portions produce a fully-reconstituted antibiotic resistance gene via protein splicing and thus only these cells can resist selection. This process is described in more detail infra in relation to FIG. 1G.

Advantages of MVT editing include increasing the number of edits possible in each individual cell by placing selective pressure on each cell to maintain more than one editing plasmid. Further, MVT editing may be practiced with dual, triple or more editing cassettes or ribozyme-containing editing cassettes; that is, use of editing cassettes or ribozyme-containing editing cassettes that comprise two or more gRNA/donor DNA pairs to further increase the number of edits per cell per round of editing.

FIG. 1D a simplified graphic of a MVT system for editing yeast genomes. In FIG. 1D, a pool (e.g., library) of editing cassettes is combined with a linear vector backbone comprising 1) a coding sequence for a nuclease, 2) an antibiotic resistance gene, and 3) a 2µ origin of replication and the editing cassettes and linear vector backbone are transformed into yeast cells. Gap repair in the yeast cells inserts the editing cassettes into the linear vector backbone via homologous recombination between homologous sequences on the linear vector backbone and editing cassette thus creating an editing vector. Following transformation, cells that have been properly transformed are selected by antibiotic selection, resulting in a library of cells comprising assembled editing vectors. Again, the probability of a unique editing cassette or ribozyme-containing editing cassette becoming incorporated via gap repair into a plasmid backbone is a function of the size of the editing cassette pool or ribozyme-containing editing cassette pool and the distribution of editing cassettes or ribozyme-containing editing cassettes within the pool. The more editing cassettes or ribozyme-containing editing cassettes in the library and the more uniform the pool of editing cassettes or ribozyme-containing editing cassettes, the higher the probability unique cassettes will be incorporated into the linearized plasmid backbones in each cell allowing for multiple edits per cell. Thus, the present embodiment uses a single-type vector backbone but adjusting the size and uniformity of the editing cassette pool or ribozyme-containing editing cassette pool allows for multiple editing cassettes to be incorporated into vector backbones in each cell.

FIG. 1E is a simplified graphic of an alternative system for editing yeast genomes. In FIG. 1E, a pool (e.g., library) of editing cassettes or ribozyme-containing editing cassettes is combined with linear vector backbones comprising 1) a coding sequence for a nuclease, 2) an antibiotic resistance gene, and 3) a 2µ origin of replication. The editing cassettes or ribozyme-containing editing cassettes and linear vector backbone are then transformed into yeast cells. The difference between the processes in FIG. 1D and FIG. 1E is that in FIG. 1E, at least two different linear vector backbones are used, where the difference between the two vector backbones is that one vector backbone comprises a first antibiotic resistance gene (e.g., selection marker) and the other vector backbone comprises a second antibiotic resistance gene, and the first and second antibiotic resistance genes are different. In FIG. 1E, gap repair in the yeast cells inserts the editing cassettes or ribozyme-containing editing cassettes (e.g., library of editing cassettes or ribozyme-containing editing cassettes) into the linear vector backbones via homologous recombination between homologous sequences on the linear vector backbone and editing cassette or ribozyme-containing editing cassette to form editing vectors.

Following transformation, cells that have been properly transformed are selected by resistance to both the first and second antibiotics, resulting in a library of cells comprising assembled editing vectors. Because selective pressure on the cells requires the cells to take up and maintain editing vectors with both the first and second antibiotics, the cells are very likely to be transformed with two or more different editing vectors, and thus two or more gRNA/donor DNA pairs (e.g., editing sequences). Further, the 2µ origin of replication maintains each vector or plasmid in the yeast cell at approximately 50 copies. Note that here two different linear vector backbones with two different antibiotic markers are used; however, three, four, or five different linear vector backbones with three, four or five different antibiotic markers may be employed in the methods described herein. Thus, this alternative method, in addition to adjusting the size and uniformity of the editing cassette pool or ribozyme-containing editing cassette pool allowing for multiple editing cassettes to be incorporated into vector backbones in each cell, adds the concept of selective pressure to assure multiple vectors are maintained within each cell.

Figure 15:
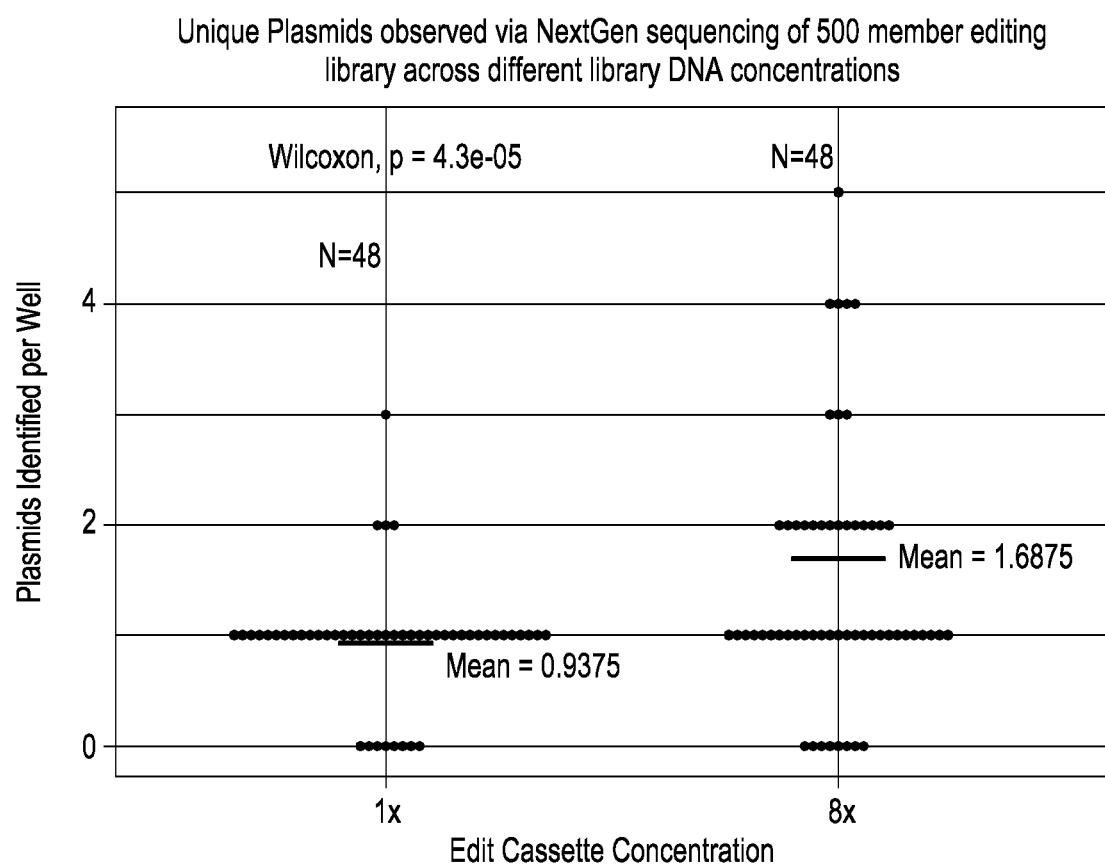
FIG. 15 shows the number of unique plasmids observed via NextGen sequencing of a 500-member editing library across different library concentrations.

In some embodiments, the backbone to insert molar ratio is roughly three cassettes for each backbone, which in practice amounts to 500 ng of backbone and 50 ng of editing cassettes. In the present methods, the cassette concentration is increased up to 8×, as shown in FIG. 15, and can be as high as 50×, or as high as 40×, or as high as 30×, or as high as 20×. The library size may range from as few as two different editing cassettes or ribozyme-containing editing cassettes up to 100,000 editing cassettes or ribozyme-containing editing cassettes or more.

FIG. 1F(i) is a simplified graphic showing the method of FIG. 1E in shorthand form. Note that there is a single library of editing cassettes and two different vector backbones where the vector backbones comprise different antibiotic resistance genes (Abx1 and Abx2). In this scheme, the editing cassettes from the library randomly are inserted into either vector backbone Abx1 or vector backbone Abx2. FIG. 1F(ii) is a "twist" on the method shown in FIG. 1E and FIG. 1F(i). Here, instead of one library of editing cassettes there are two libraries of editing cassettes where each library of editing cassettes where one library of editing cassettes has regions of homology to be inserted into vector backbone Abx1 and one library of editing cassettes has regions of homology to be inserted into vector backbone Abx2 by gap repair. In this scheme, editing cassettes are not randomly inserted into a single vector backbone, but may be selectively inserted into one of two, one of three, one of four, or more vector backbones where each different vector backbone comprises a different antibiotic resistance gene (or portion thereof as described infra). One advantage of this "twist" is that one may avoid "collision control" and experience less "edit incompatibility" between editing cassettes. For example, when performing saturation mutagenesis of a region in a genome, if a single vector backbone is used one editing cassette may cause genomic changes that inactivate the target regions for other edits to be made. However, if editing cassettes with predicted incompatibility are in the same library and thus are inserted into the same vector backbone (e.g., vector backbone Abx1), it is unlikely incompatible editing cassettes will be transformed and maintained in the same cell. That is, because of the selective pressure of two antibiotics in the edited cells, it is less likely that a cell will be transformed with and maintain two editing vectors with the same antibiotic resistance gene; instead, the cell will likely maintain two editing vectors with different antibiotic resistance genes, hence two editing cassettes that are compatible. Splitting the pool of editing cassettes in an intelligent manner between multiple vector backbones increases the likelihood that only "compatible" editing cassettes will be present in a single cell.

Figure 1G:
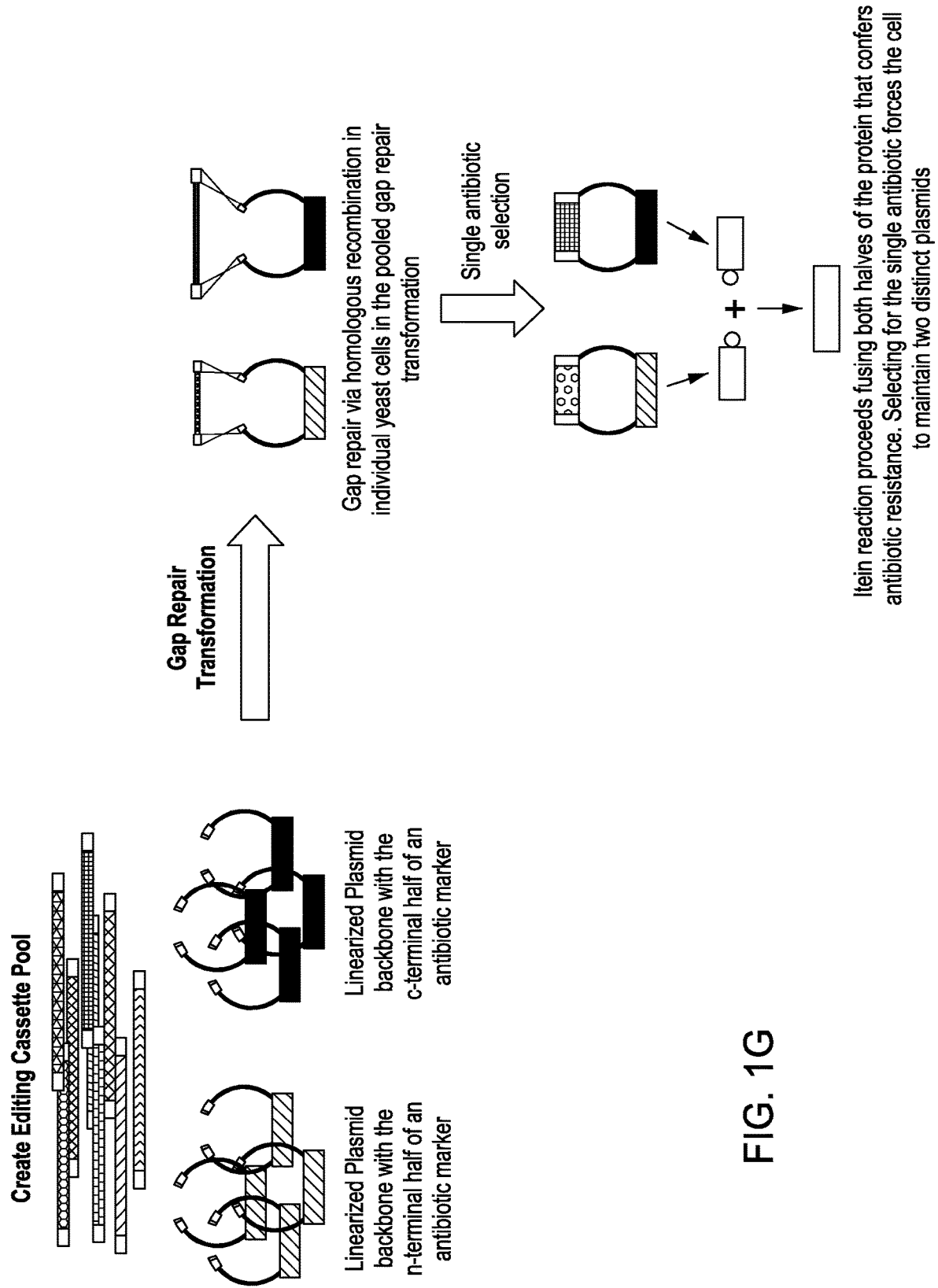
FIG. 1G is a simplified graphic of an alternative system for editing yeast genomes with two to many edits per round of editing using two different vector backbones, each with a portion of a coding sequence for an antibiotic marker.

FIG. 1G is a simplified graphic of an alternative system for editing yeast genomes related closely to the method described FIG. 1F(ii). In FIG. 1G, two pools (e.g., libraries) of editing cassettes or ribozyme-containing editing cassettes—where each library of editing cassettes comprises a different homology region for being inserted into a vector backbone—is combined with two different linear vector backbones. The first linear vector backbone comprises 1) a coding sequence for a nuclease, 2) a first portion of an antibiotic resistance gene fused to an N-terminal intein, 3) a homology insert region compatible with editing library 1, and 4) a 2μ origin of replication; and the second linear vector backbone comprises 1) a coding sequence for a nuclease, 2) a second portion of an antibiotic resistance gene fused to a C-terminal intein, 3) a homology insert region compatible with editing library 2, and 4) a 2μ origin of replication. In this embodiment, the coding region for a single antibiotic resistance gene is thus separated into portions, which is advantageous in that there is a limited number of antibiotics and antibiotic resistance genes known. Using inteins, the coding sequence for an antibiotic resistance gene can be broken up into two, three or more parts instead of using two, three or more different antibiotic resistance genes. Using a combination of inteins and multiple antibiotic resistance genes many unique editing vectors can be used to confer multiple unique edits.

The editing cassettes or ribozyme-containing editing cassettes and linear vector backbones are then transformed into yeast cells. Whereas the method depicted in FIG. 1E uses at least two different linear vector backbones where each comprises a different antibiotic resistance gene, here the different vector backbones comprise portions of a single antibiotic resistance gene fused to inteins. Inteins are self-splicing polypeptides with an ability to excise themselves from flanking protein regions with remarkable precision. (See, e.g., Pavankumar, Microorganisms, 6, 19 (2018) and Jillette, et al., Nature Communications, (2019)10:4968, both of which are incorporated by reference for all purposes.) Two well-known and well-characterized inteins are those derived from *Nostoc punctiforme* PCC73102 split alpha subunit of the DNA polymerase III intein (NpuDnaE) and from *Synechocystis* sp. PCC6803 DnaB helicase SspDnaB. In the process of excision, the inteins ligate the flanked host protein fragments. As in the previously methods (e.g., depicted in FIGS. 1D, 1E, and 1F(ii)), gap repair in the yeast cells inserts the editing cassettes or ribozyme-containing editing cassettes (e.g., libraries of editing cassettes or ribozyme-containing editing cassettes) into the linear vector backbones via homologous recombination between homologous sequences on the linear vector backbone and editing cassette or ribozyme-containing editing cassette to form editing vectors.

Following transformation, cells that have been properly transformed with all portions of the antibiotic resistance gene (here, in this FIG. 1G there are two) are selected by resistance to the single antibiotic. The portions of the antibiotic resistance gene are transcribed and translated and the fused N-terminal and C-terminal inteins have the ability to splice themselves out from the flanking protein fragments (exteins) post-transcriptionally, acting much like introns. Because selective pressure on the cells requires the cells to take up and maintain editing vectors with both the first and second portions of the single antibiotic resistance gene, the cells are very likely to be transformed with both editing vectors, and thus two or more gRNA/donor DNA pairs (e.g., editing sequences). Again, the 2μ origin of replication maintains each vector or plasmid in the yeast cell maintains the vectors at approximately 50 copies.

Note that in this example, two different linear vector backbones with two portions of a single antibiotic resistance gene are used; however, the antibiotic resistance gene may be split into three, four, or five portions fused to different N-terminal and C-terminal inteins; alternatively, e.g., four different linear vector backbones may be used with the first vector backbone comprising, e.g., a first portion of an Abx1 resistant gene fused to the N-terminus of intein1 (and a first homology for editing cassette inserts); the second vector backbone comprising a second portion of an Abx1 resistant gene fused to the C-terminus of intein1 (and a second homology for editing cassette inserts); the third vector backbone comprising a first portion of an Abx2 resistant gene fused to the N-terminus of intein2 (and a third homology for editing cassette inserts); and the fourth vector backbone comprising a second portion of an Abx2 resistant gene fused to the C-terminus of intein2 (and a fourth homology for editing cassette inserts). Like the method depicted in FIG. 1E, this alternative method—in addition to adjusting the size and uniformity of the editing cassette pool or ribozyme-containing editing cassette pool allowing for multiple editing cassettes to be incorporated into vector backbones in each cell—adds the concept of selective pressure to assure multiple vectors are maintained within each cell.

Figure 1H:
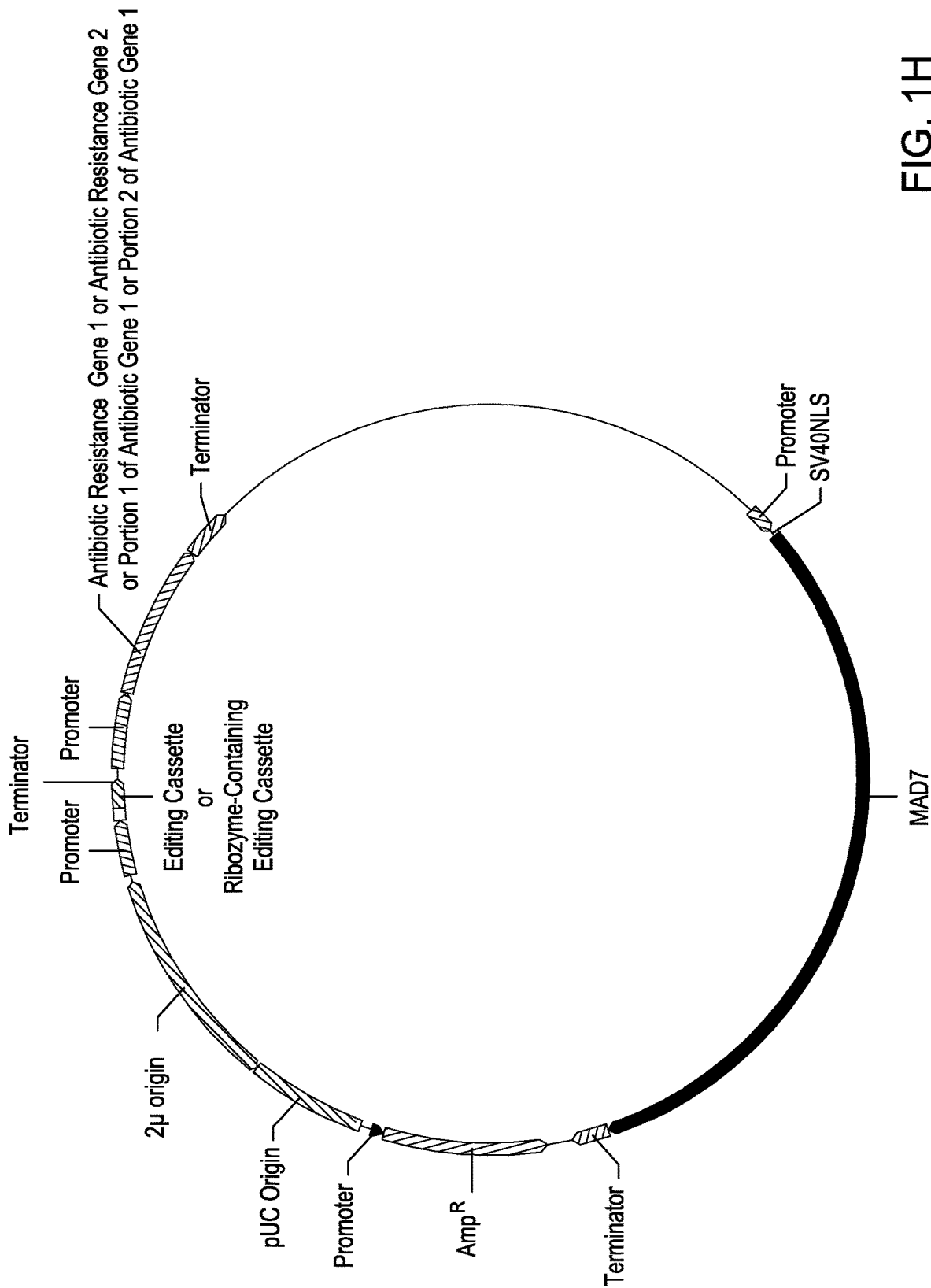
FIG. 1H is an exemplary map for a vector backbone for performing multiplex simultaneous nucleic acid-guided nuclease editing.

FIG. 1H is an exemplary editing vector map after gap repair, where the editing vector map comprises, inter alia, an editing cassette or ribozyme-containing editing cassette (or compound editing cassette or ribozyme-containing editing cassette), a selectable marker, and the coding sequence for the nuclease MAD7. In the vector map in FIG. 1F, a single editing cassette is shown. Beginning at 11:55 o'clock, there is a promoter driving transcription of the gRNA/donor DNA pair, and in some embodiments this promoter is a pol II promoter, followed by a terminator such as a pol II or SUP4 terminator; a promoter driving transcription of an antibiotic resistance gene 1 or 2 (chosen from at least two different antibiotic resistance genes) or two different portions of a single antibiotic resistance gene followed by a terminator; another promoter driving transcription of an SV40 nuclear localization sequence and the MAD7 nuclease coding sequence followed by a terminator; a promoter driving an ampicillin resistance gene (which is in a reverse orientation to the transcription of the other elements); a pUC origin of replication for propagation of the editing vector in bacteria; and a 2μ origin of replication for propagation of multiple copies of each editing vector in yeast. Again, it should be apparent to one of ordinary skill in the art given the present disclosure that there may be more than one gRNA/donor DNA pair in the editing cassette or ribozyme-containing editing cassette; that is—for a two-edit editing cassette or ribozyme-containing editing cassette—there may be a promoter driving transcription of a first gRNA, a first donor DNA sequence, followed by a second gRNA, and a second donor DNA sequence followed by a terminator. In addition, there optionally may be penta-T or penta-T+G motifs between the gRNA/donor DNA pairs; that is between the first gRNA/donor DNA sequence and the second gRNA/donor DNA sequence.

In each of the different methods and compositions herein it should be apparent to one of ordinary skill in the art given the present disclosure that the methods and compositions provide for multiple edits per round per cell by using a compound editing cassette in a single vector backbone or by using multiple vectors each with a different editing cassette as well as performing multiple rounds of editing (e.g., recursive editing) using these methods and compositions.

Figure 2A:
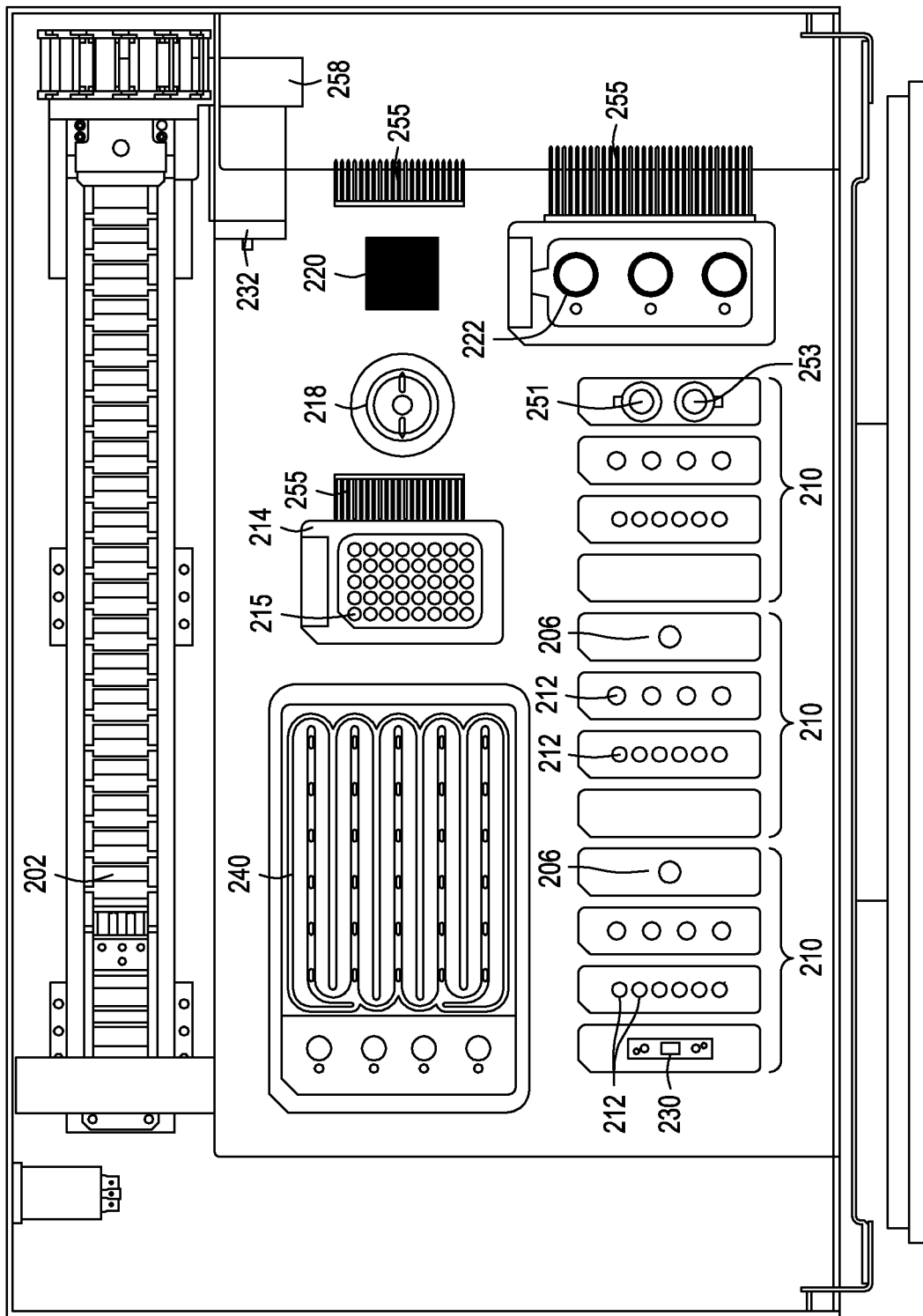
FIGS. 2A-2C depict three different views of an exemplary automated multi-module cell processing instrument for performing nucleic acid-guided nuclease editing employing a split protein reporter system.

Automated Cell Editing Instruments and Modules to Perform Nucleic Acid-Guided Nuclease Editing in Cells Automated Cell Editing Instruments FIG. 2A depicts an exemplary automated multi-module cell processing instrument to, e.g., perform one of the exemplary novel methods using the novel compositions described herein. The instrument, for example, may be and preferably is designed as a stand-alone desktop instrument for use within a laboratory environment. The instrument 200 (not labeled in this FIG. 2A, but see FIG. 2B) may incorporate a mixture of reusable and disposable components for performing the various integrated processes in conducting automated genome cleavage and/or editing in cells without human intervention. Illustrated is a gantry 202, providing an automated mechanical motion system (actuator) (not shown) that supplies XYZ axis motion control to, e.g., an automated (i.e., robotic) liquid handling system 258 including, e.g., an air displacement pipettor 232 which allows for cell processing among multiple modules without human intervention. In some automated multi-module cell processing instruments, the air displacement pipettor 232 is moved by gantry 202 and the various modules and reagent cartridges remain stationary; however, in other embodiments, the liquid handling system 258 may stay stationary while the various modules and reagent cartridges are moved. Also included in the automated multi-module cell processing instrument 200 are reagent cartridges 210 comprising reservoirs 212 and transformation module 230 (e.g., a flow-through electroporation device as described in detail in relation to FIGS. 5B-5F), as well as wash reservoirs 206, cell input reservoir 251 and cell output reservoir 253. The wash reservoirs 206 may be configured to accommodate large tubes, for example, wash solutions, or solutions that are used often throughout an iterative process. Although two of the reagent cartridges 210 comprise a wash reservoir 206 in FIG. 2A, the wash reservoirs instead could be included in a wash cartridge where the reagent and wash cartridges are separate cartridges. In such a case, the reagent cartridge 210 and a wash cartridge may be identical except for the consumables (reagents or other components contained within the various inserts) inserted therein.

In some implementations, the reagent cartridges 210 are disposable kits comprising reagents and cells for use in the automated multi-module cell processing/editing instrument 200. For example, a user may open and position each of the reagent cartridges 210 comprising various desired inserts and reagents within the chassis of the automated multi-module cell editing instrument 200 prior to activating cell processing. Further, each of the reagent cartridges 210 may be inserted into receptacles in the chassis having different temperature zones appropriate for the reagents contained therein.

Also illustrated in FIG. 2A is the robotic liquid handling system 258 including the gantry 202 and air displacement pipettor 232. Also shown is pipette tip box 214 with pipette tips 215. In some examples, the robotic handling system 258 may include an automated liquid handling system such as those manufactured by Tecan Group Ltd. of Mannedorf, Switzerland, Hamilton Company of Reno, Nev. (see, e.g., WO2018015544A1), or Beckman Coulter, Inc. of Fort Collins, Colo. (see, e.g., US20160018427A1). Pipette tips may be provided in a pipette transfer tip supply (not shown) for use with the air displacement pipettor 232.

Inserts or components of the reagent cartridges 210, in some implementations, are marked with machine-readable indicia (not shown), such as bar codes, for recognition by the robotic liquid handling system 258. For example, the robotic liquid handling system 258 may scan one or more inserts within each of the reagent cartridges 210 to confirm contents. In other implementations, machine-readable indicia may be marked upon each reagent cartridge 210, and a processing system (not shown, but see element 237 of FIG. 2B) of the automated multi-module cell editing instrument 200 may identify a stored materials map based upon the machine-readable indicia. In the embodiment illustrated in FIG. 2A, a cell growth module comprises a cell growth vial 218 (described in greater detail below in relation to FIGS. 3A-3D). Additionally seen is the TFF module 222 (described above in detail in relation to FIGS. 4A-4E). Also illustrated as part of the automated multi-module cell processing instrument 200 of FIG. 2A is a singulation module 240 (e.g., a solid wall isolation, incubation and normalization device (SWIIN device) is shown here) described herein in relation to FIGS. 6C-6F, served by, e.g., robotic liquid handling system 258 and air displacement pipettor 232. Additionally seen is a selection module 220. Also note the placement of three heatsinks 255.

Figure 2B:
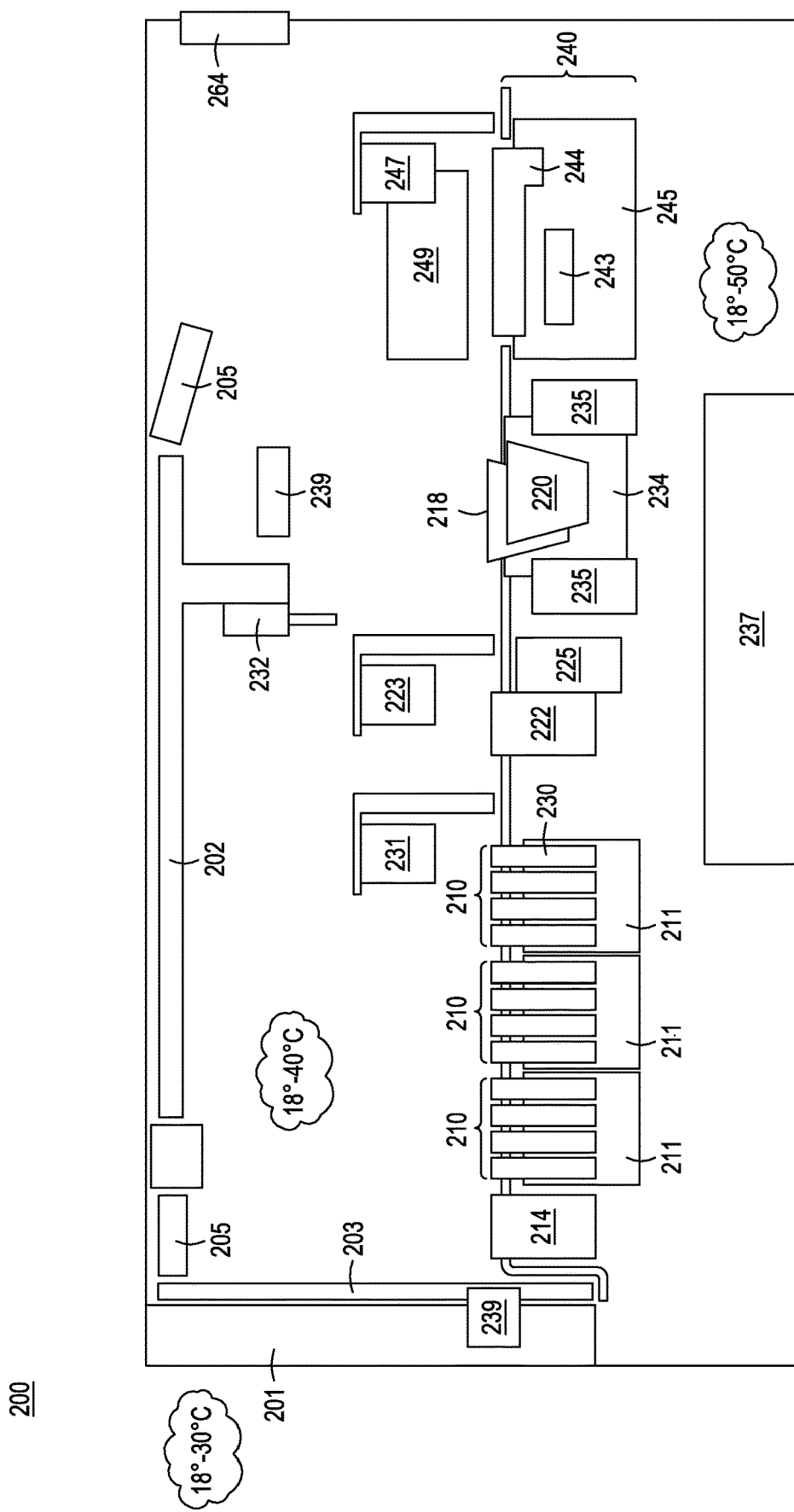

FIG. 2B is a simplified representation of the contents of the exemplary multi-module cell processing instrument 200 depicted in FIG. 2A. Cartridge-based source materials (such as in reagent cartridges 210), for example, may be positioned in designated areas on a deck of the instrument 200 for access by an air displacement pipettor 232. The deck of the multi-module cell processing instrument 200 may include a protection sink such that contaminants spilling, dripping, or overflowing from any of the modules of the instrument 200 are contained within a lip of the protection sink. Also seen are reagent cartridges 210, which are shown disposed with thermal assemblies 211 which can create temperature zones appropriate for different regions, and pipette tip box 214. Note that one of the reagent cartridges also comprises a flow-through electroporation device 230 (FTEP), served by FTEP interface (e.g., manifold arm) and actuator 231. Also seen is TFF module 222 with adjacent thermal assembly 225, where the TFF module is served by TFF interface (e.g., manifold arm) and actuator 223. Thermal assemblies 225, 235, and 245 encompass thermal electric devices such as Peltier devices, as well as heatsinks, fans and coolers. The rotating growth vial 218 is within a growth module 234, where the growth module is served by two thermal assemblies 235. Selection module is seen at 220. Also seen is the SWIIN module 240, comprising a SWIIN cartridge 240, where the SWIIN module also comprises a thermal assembly 245, cover 244, illumination 243 (in this embodiment, backlighting), evaporation and condensation control 249, and where the SWIIN module is served by SWIIN interface (e.g., manifold arm) and actuator 247. Also seen in this view is touch screen display 201, display actuator 203, illumination 205 (one on either side of multi-module cell processing instrument 200), and cameras 239 (one illumination device on either side of multi-module cell processing instrument 200). Finally, element 237 comprises electronics, such as circuit control boards, high-voltage amplifiers, power supplies, and power entry; as well as pneumatics, such as pumps, valves and sensors.

Figure 2C:
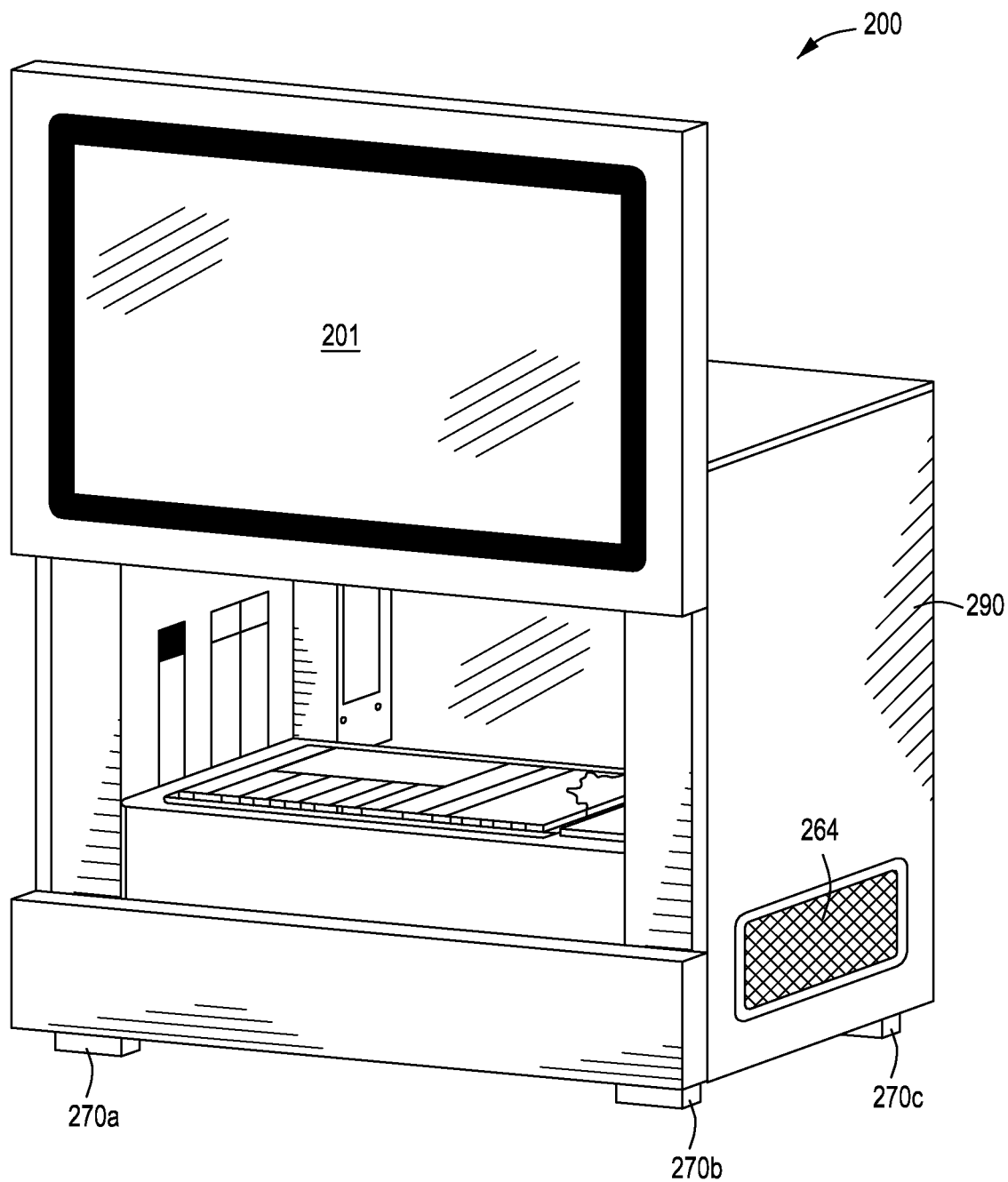

FIG. 2C illustrates a front perspective view of multi-module cell processing instrument 200 for use in as a desktop version of the automated multi-module cell editing instrument 200. For example, a chassis 290 may have a width of about 24-48 inches, a height of about 24-48 inches and a depth of about 24-48 inches. Chassis 290 may be and preferably is designed to hold all modules and disposable supplies used in automated cell processing and to perform all processes required without human intervention; that is, chassis 290 is configured to provide an integrated, stand-alone automated multi-module cell processing instrument. As illustrated in FIG. 2C, chassis 290 includes touch screen display 201, cooling grate 264, which allows for air flow via an internal fan (not shown). The touch screen display provides information to a user regarding the processing status of the automated multi-module cell editing instrument 200 and accepts inputs from the user for conducting the cell processing. In this embodiment, the chassis 290 is lifted by adjustable feet 270a, 270b, 270c and 270d (feet 270a-270c are shown in this FIG. 2C). Adjustable feet 270a-270d, for example, allow for additional air flow beneath the chassis 290 (foot 270d is not shown).

Inside the chassis 290, in some implementations, will be most or all of the components described in relation to FIGS. 2A and 2B, including the robotic liquid handling system disposed along a gantry, reagent cartridges 210 including a flow-through electroporation device, a rotating growth vial 218 in a cell growth module 234, a tangential flow filtration module 222, a SWIIN module 240 as well as interfaces and actuators for the various modules. In addition, chassis 290 houses control circuitry, liquid handling tubes, air pump controls, valves, sensors, thermal assemblies (e.g., heating and cooling units) and other control mechanisms. For examples of multi-module cell editing instruments, see U.S. Pat. No. 10,253,316, issued 9 Apr. 2019; U.S. Pat. No. 10,329,559, issued 25 Jun. 2019; U.S. Pat. No. 10,323,242, issued 18 Jun. 2019; U.S. Pat. No. 10,421,959, issued 24 Sep. 2019; U.S. Pat. No. 10,465,185, issued 5 Nov. 2019; U.S. Pat. No. 10,519,437, issued 31 Dec. 2019; and U.S. Ser. No. 16/680,643, filed 12 Nov. 2019; Ser. No. 16/666,964, filed 29 Oct. 2019; Ser. No. 16/750,369, filed 23 Jan. 2020, all of which are herein incorporated by reference in their entirety.

The Rotating Cell Growth Module

Figure 3A:
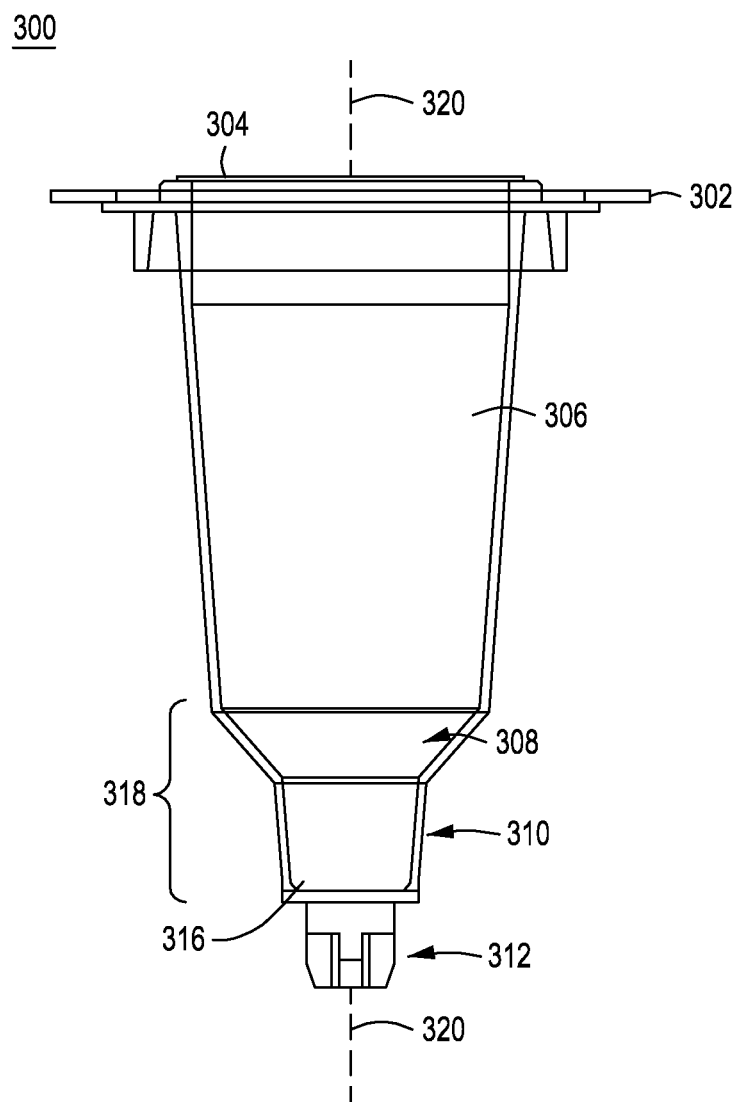
FIG. 3A depicts one embodiment of a rotating growth vial for use with the cell growth module described herein and in relation to FIGS. 3B-3D.

FIG. 3A shows one embodiment of a rotating growth vial 300 for use with the cell growth device and in the automated multi-module cell processing instruments described herein. The rotating growth vial 300 is an optically-transparent container having an open end 304 for receiving liquid media and cells, a central vial region 306 that defines the primary container for growing cells, a tapered-to-constricted region 318 defining at least one light path 310, a closed end 316, and a drive engagement mechanism 312. The rotating growth vial 300 has a central longitudinal axis 320 around which the vial rotates, and the light path 310 is generally perpendicular to the longitudinal axis of the vial. The first light path 310 is positioned in the lower constricted portion of the tapered-to-constricted region 318. Optionally, some embodiments of the rotating growth vial 300 have a second light path 308 in the tapered region of the tapered-to-constricted region 318. Both light paths in this embodiment are positioned in a region of the rotating growth vial that is constantly filled with the cell culture (cells+growth media) and are not affected by the rotational speed of the growth vial. The first light path 310 is shorter than the second light path 308 allowing for sensitive measurement of OD values when the OD values of the cell culture in the vial are at a high level (e.g., later in the cell growth process), whereas the second light path 308 allows for sensitive measurement of OD values when the OD values of the cell culture in the vial are at a lower level (e.g., earlier in the cell growth process).

The drive engagement mechanism 312 engages with a motor (not shown) to rotate the vial. In some embodiments, the motor drives the drive engagement mechanism 312 such that the rotating growth vial 300 is rotated in one direction only, and in other embodiments, the rotating growth vial 300 is rotated in a first direction for a first amount of time or periodicity, rotated in a second direction (i.e., the opposite direction) for a second amount of time or periodicity, and this process may be repeated so that the rotating growth vial 300 (and the cell culture contents) are subjected to an oscillating motion. Further, the choice of whether the culture is subjected to oscillation and the periodicity therefor may be selected by the user. The first amount of time and the second amount of time may be the same or may be different. The amount of time may be 1, 2, 3, 4, 5, or more seconds, or may be 1, 2, 3, 4 or more minutes. In another embodiment, in an early stage of cell growth the rotating growth vial 300 may be oscillated at a first periodicity (e.g., every 60 seconds), and then a later stage of cell growth the rotating growth vial 300 may be oscillated at a second periodicity (e.g., every one second) different from the first periodicity.

The rotating growth vial 300 may be reusable or, preferably, the rotating growth vial is consumable. In some embodiments, the rotating growth vial is consumable and is presented to the user pre-filled with growth medium, where the vial is hermetically sealed at the open end 304 with a foil seal. A medium-filled rotating growth vial packaged in such a manner may be part of a kit for use with a stand-alone cell growth device or with a cell growth module that is part of an automated multi-module cell processing system. To introduce cells into the vial, a user need only pipette up a desired volume of cells and use the pipette tip to punch through the foil seal of the vial. Open end 304 may optionally include an extended lip 302 to overlap and engage with the cell growth device. In automated systems, the rotating growth vial 300 may be tagged with a barcode or other identifying means that can be read by a scanner or camera (not shown) that is part of the automated system.

The volume of the rotating growth vial 300 and the volume of the cell culture (including growth medium) may vary greatly, but the volume of the rotating growth vial 300 must be large enough to generate a specified total number of cells. In practice, the volume of the rotating growth vial 300 may range from 1-250 mL, 2-100 mL, from 5-80 mL, 10-50 mL, or from 12-35 mL. Likewise, the volume of the cell culture (cells+growth media) should be appropriate to allow proper aeration and mixing in the rotating growth vial 400. Proper aeration promotes uniform cellular respiration within the growth media. Thus, the volume of the cell culture should be approximately 5-85% of the volume of the growth vial or from 20-60% of the volume of the growth vial. For example, for a 30 mL growth vial, the volume of the cell culture would be from about 1.5 mL to about 26 mL, or from 6 mL to about 18 mL.

The rotating growth vial 300 preferably is fabricated from a bio-compatible optically transparent material—or at least the portion of the vial comprising the light path(s) is transparent. Additionally, material from which the rotating growth vial is fabricated should be able to be cooled to about 4° C. or lower and heated to about 55° C. or higher to accommodate both temperature-based cell assays and long-term storage at low temperatures. Further, the material that is used to fabricate the vial must be able to withstand temperatures up to 55° C. without deformation while spinning. Suitable materials include cyclic olefin copolymer (COC), glass, polyvinyl chloride, polyethylene, polyamide, polypropylene, polycarbonate, poly(methyl methacrylate (PMMA), polysulfone, polyurethane, and co-polymers of these and other polymers. Preferred materials include polypropylene, polycarbonate, or polystyrene. In some embodiments, the rotating growth vial is inexpensively fabricated by, e.g., injection molding or extrusion.

Figure 3B:
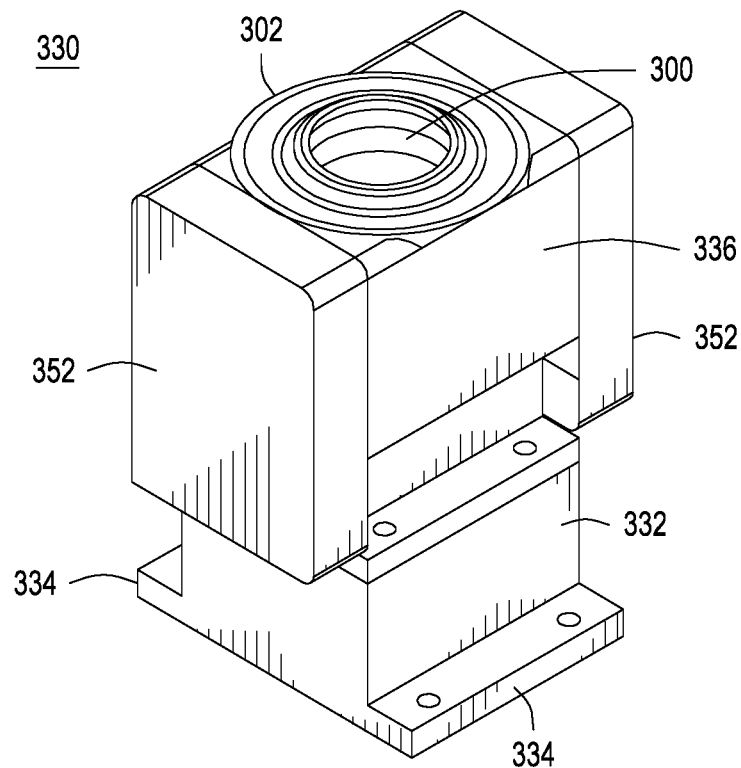
FIG. 3B illustrates a perspective view of one embodiment of a rotating growth vial in a cell growth module housing.
Figure 3C:
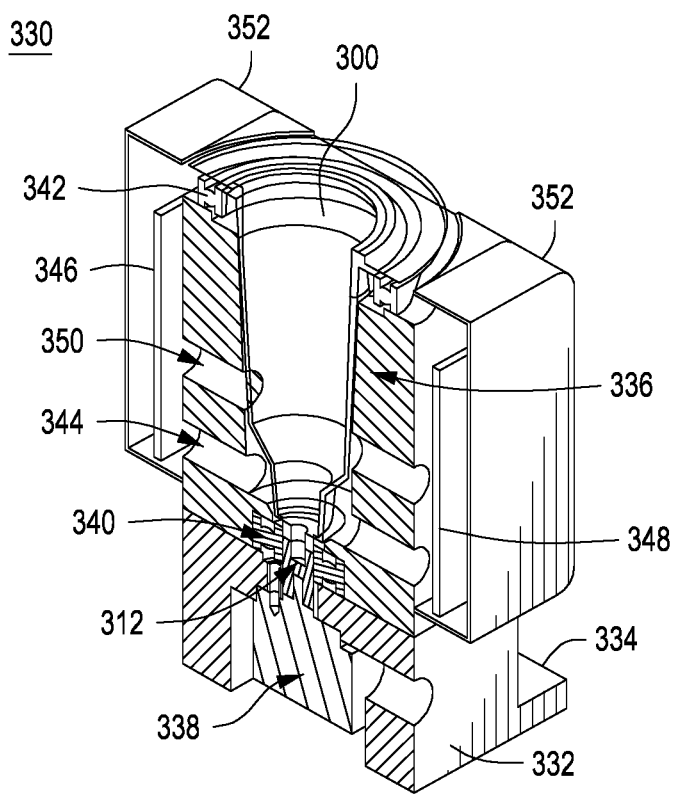
FIG. 3C depicts a cut-away view of the cell growth module from FIG. 3B.

FIG. 3B is a perspective view of one embodiment of a cell growth device 330. FIG. 3C depicts a cut-away view of the cell growth device 330 from FIG. 3B. In both figures, the rotating growth vial 300 is seen positioned inside a main housing 336 with the extended lip 302 of the rotating growth vial 300 extending above the main housing 336. Additionally, end housings 352, a lower housing 332 and flanges 334 are indicated in both figures. Flanges 334 are used to attach the cell growth device 330 to heating/cooling means or other structure (not shown). FIG. 3C depicts additional detail. In FIG. 3C, upper bearing 342 and lower bearing 340 are shown positioned within main housing 336. Upper bearing 342 and lower bearing 340 support the vertical load of rotating growth vial 300. Lower housing 332 contains the drive motor 338. The cell growth device 330 of FIG. 3C comprises two light paths: a primary light path 344, and a secondary light path 350. Light path 344 corresponds to light path 310 positioned in the constricted portion of the tapered-to-constricted portion of the rotating growth vial 300, and light path 350 corresponds to light path 308 in the tapered portion of the tapered-to-constricted portion of the rotating growth via 316. Light paths 310 and 308 are not shown in FIG. 3C but may be seen in FIG. 3A. In addition to light paths 344 and 340, there is an emission board 348 to illuminate the light path(s), and detector board 346 to detect the light after the light travels through the cell culture liquid in the rotating growth vial 300.

The motor 338 engages with drive mechanism 312 and is used to rotate the rotating growth vial 300. In some embodiments, motor 338 is a brushless DC type drive motor with built-in drive controls that can be set to hold a constant revolution per minute (RPM) between 0 and about 3000 RPM. Alternatively, other motor types such as a stepper, servo, brushed DC, and the like can be used. Optionally, the motor 338 may also have direction control to allow reversing of the rotational direction, and a tachometer to sense and report actual RPM. The motor is controlled by a processor (not shown) according to, e.g., standard protocols programmed into the processor and/or user input, and the motor may be configured to vary RPM to cause axial precession of the cell culture thereby enhancing mixing, e.g., to prevent cell aggregation, increase aeration, and optimize cellular respiration.

Main housing 336, end housings 352 and lower housing 332 of the cell growth device 330 may be fabricated from any suitable, robust material including aluminum, stainless steel, and other thermally conductive materials, including plastics. These structures or portions thereof can be created through various techniques, e.g., metal fabrication, injection molding, creation of structural layers that are fused, etc. Whereas the rotating growth vial 300 is envisioned in some embodiments to be reusable, but preferably is consumable, the other components of the cell growth device 330 are preferably reusable and function as a stand-alone benchtop device or as a module in a multi-module cell processing system.

The processor (not shown) of the cell growth device 330 may be programmed with information to be used as a "blank" or control for the growing cell culture. A "blank" or control is a vessel containing cell growth medium only, which yields 100% transmittance and 0 OD, while the cell sample will deflect light rays and will have a lower percent transmittance and higher OD. As the cells grow in the media and become denser, transmittance will decrease and OD will increase. The processor (not shown) of the cell growth device 330—may be programmed to use wavelength values for blanks commensurate with the growth media typically used in cell culture (whether, e.g., mammalian cells, bacterial cells, animal cells, yeast cells, etc.). Alternatively, a second spectrophotometer and vessel may be included in the cell growth device 330, where the second spectrophotometer is used to read a blank at designated intervals.

Figure 3D:
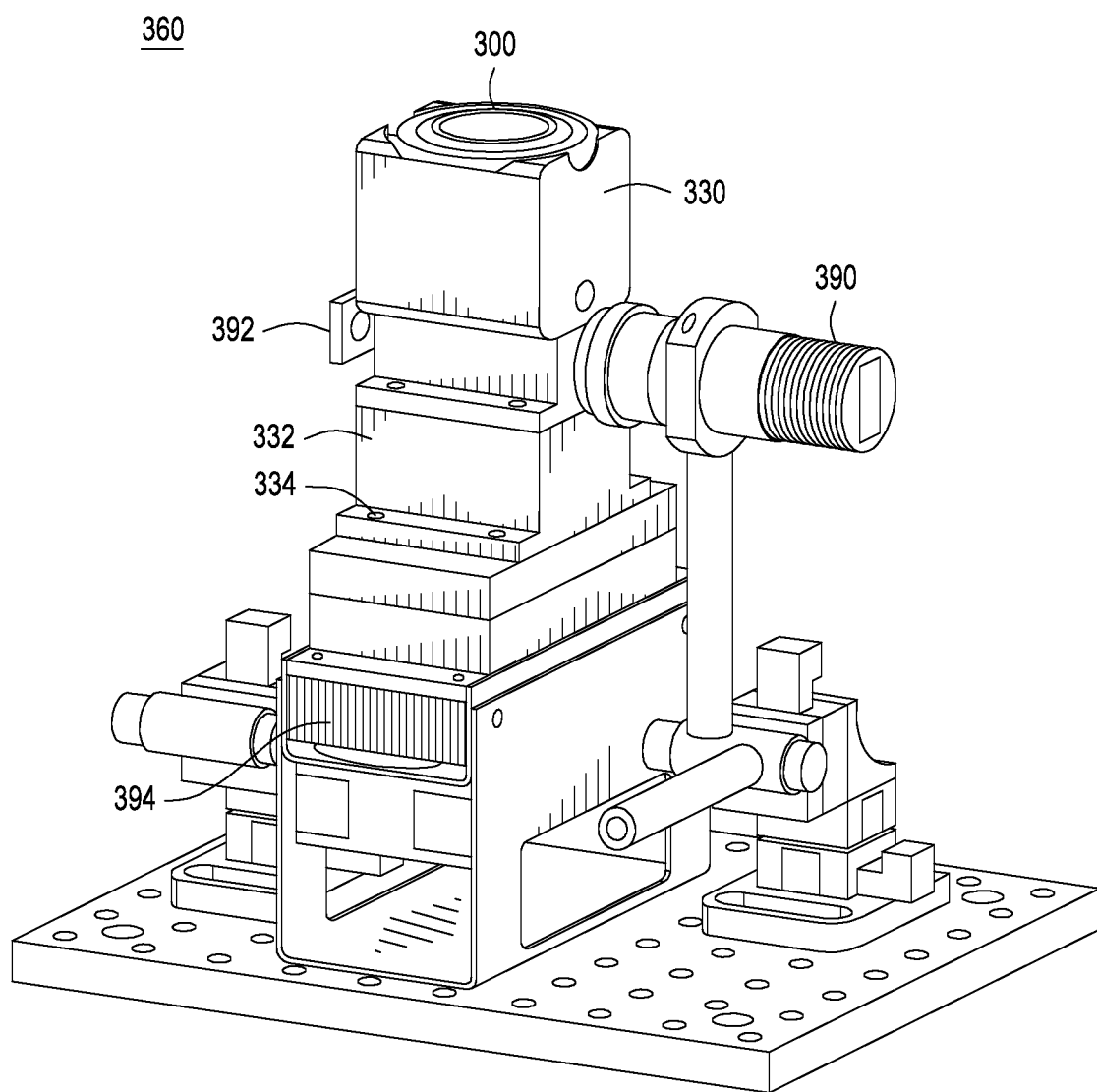
FIG. 3D illustrates the cell growth module of FIG. 3B coupled to LED, detector, and temperature regulating components.

FIG. 3D illustrates a cell growth device 330 as part of an assembly 360 comprising the cell growth device 330 of FIG. 3B coupled to light source 390, detector 392, and thermal components 394. The rotating growth vial 300 is inserted into the cell growth device. Components of the light source 390 and detector 392 (e.g., such as a photodiode with gain control to cover 5-log) are coupled to the main housing of the cell growth device. The lower housing 332 that houses the motor that rotates the rotating growth vial 300 is illustrated, as is one of the flanges 334 that secures the cell growth device 330 to the assembly. Also, the thermal components 394 illustrated are a Peltier device or thermoelectric cooler. In this embodiment, thermal control is accomplished by attachment and electrical integration of the cell growth device 330 to the thermal components 394 via the flange 334 on the base of the lower housing 332. Thermoelectric coolers are capable of "pumping" heat to either side of a junction, either cooling a surface or heating a surface depending on the direction of current flow. In one embodiment, a thermistor is used to measure the temperature of the main housing and then, through a standard electronic proportional-integral-derivative (PID) controller loop, the rotating growth vial 300 is controlled to approximately +/−0.5° C.

In use, cells are inoculated (cells can be pipetted, e.g., from an automated liquid handling system or by a user) into pre-filled growth media of a rotating growth vial 300 by piercing though the foil seal or film. The programmed software of the cell growth device 330 sets the control temperature for growth, typically 30° C., then slowly starts the rotation of the rotating growth vial 300. The cell/growth media mixture slowly moves vertically up the wall due to centrifugal force allowing the rotating growth vial 300 to expose a large surface area of the mixture to a normal oxygen environment. The growth monitoring system takes either continuous readings of the OD or OD measurements at pre-set or pre-programmed time intervals. These measurements are stored in internal memory and if requested the software plots the measurements versus time to display a growth curve. If enhanced mixing is required, e.g., to optimize growth conditions, the speed of the vial rotation can be varied to cause an axial precession of the liquid, and/or a complete directional change can be performed at programmed intervals. The growth monitoring can be programmed to automatically terminate the growth stage at a pre-determined OD, and then quickly cool the mixture to a lower temperature to inhibit further growth.

One application for the cell growth device 330 is to constantly measure the optical density of a growing cell culture. One advantage of the described cell growth device is that optical density can be measured continuously (kinetic monitoring) or at specific time intervals; e.g., every 5, 10, 15, 20, 30 45, or 60 seconds, or every 1, 2, 3, 4, 5, 6, 7, 8, 9, or 10 minutes. While the cell growth device 330 has been described in the context of measuring the optical density (OD) of a growing cell culture, it should, however, be understood by a skilled artisan given the teachings of the present specification that other cell growth parameters can be measured in addition to or instead of cell culture OD. As with optional measure of cell growth in relation to the solid wall device or module described supra, spectroscopy using visible, UV, or near infrared (NIR) light allows monitoring the concentration of nutrients and/or wastes in the cell culture and other spectroscopic measurements may be made; that is, other spectral properties can be measured via, e.g., dielectric impedance spectroscopy, visible fluorescence, fluorescence polarization, or luminescence. Additionally, the cell growth device 330 may include additional sensors for measuring, e.g., dissolved oxygen, carbon dioxide, pH, conductivity, and the like. For additional details regarding rotating growth vials and cell growth devices see U.S. Pat. No. 10,435,662, issued 8 Oct. 2019; U.S. Pat. No. 10,443,031, issued 15 Oct. 2019; and U.S. Ser. No. 16/552,981, filed 27 Aug. 2019 and Ser. No. 16/780,640, filed 3 Feb. 2020.

The Cell Concentration Module

As described above in relation to the rotating growth vial and cell growth module, in order to obtain an adequate number of cells for transformation or transfection, cells typically are grown to a specific optical density in medium appropriate for the growth of the cells of interest; however, for effective transformation or transfection, it is desirable to decrease the volume of the cells as well as render the cells competent via buffer or medium exchange. Thus, one sub-component or module that is desired in cell processing systems to perform the methods described herein is a module or component that can grow, perform buffer exchange, and/or concentrate cells and render them competent so that they may be transformed or transfected with the nucleic acids needed for engineering or editing the cell's genome.

Figure 4A:
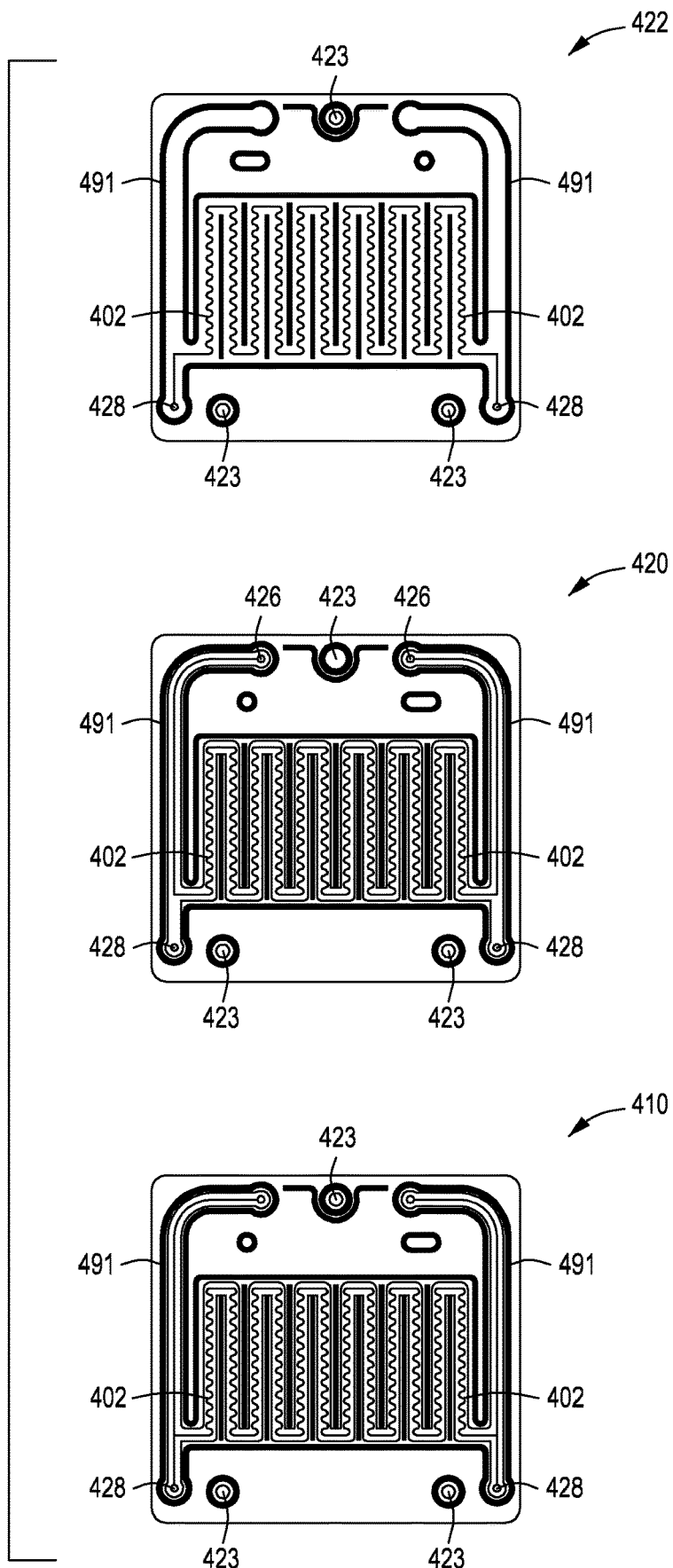
FIG. 4A depicts retentate (top) and permeate (bottom) members for use in a tangential flow filtration module (e.g., cell growth and/or concentration module), as well as the retentate and permeate members assembled into a tangential flow assembly (bottom).

FIG. 4A shows a retentate member 422 (top), permeate member 420 (middle) and a tangential flow assembly 410 (bottom) comprising the retentate member 422, membrane 424 (not seen in FIG. 4A), and permeate member 420 (also not seen). In FIG. 4A, retentate member 422 comprises a tangential flow channel 402, which has a serpentine configuration that initiates at one lower corner of retentate member 422—specifically at retentate port 428—traverses across and up then down and across retentate member 422, ending in the other lower corner of retentate member 422 at a second retentate port 428. Also seen on retentate member 422 are energy directors 491, which circumscribe the region where a membrane or filter (not seen in this FIG. 4A) is seated, as well as interdigitate between areas of channel 402. Energy directors 491 in this embodiment mate with and serve to facilitate ultrasonic welding or bonding of retentate member 422 with permeate/filtrate member 420 via the energy director component 491 on permeate/filtrate member 420 (at right). Additionally, countersinks 423 can be seen, two on the bottom one at the top middle of retentate member 422. Countersinks 423 are used to couple and tangential flow assembly 410 to a reservoir assembly (not seen in this FIG. 4A but see FIG. 4B).

Permeate/filtrate member 420 is seen in the middle of FIG. 4A and comprises, in addition to energy director 491, through-holes for retentate ports 428 at each bottom corner (which mate with the through-holes for retentate ports 428 at the bottom corners of retentate member 422), as well as a tangential flow channel 402 and two permeate/filtrate ports 426 positioned at the top and center of permeate member 420. The tangential flow channel 402 structure in this embodiment has a serpentine configuration and an undulating geometry, although other geometries may be used. Permeate member 420 also comprises countersinks 423, coincident with the countersinks 423 on retentate member 420.

On the left of FIG. 4A is a tangential flow assembly 410 comprising the retentate member 422 and permeate member 420 seen in this FIG. 4A. In this view, retentate member 422 is "on top" of the view, a membrane (not seen in this view of the assembly) would be adjacent and under retentate member 422 and permeate member 420 (also not seen in this view of the assembly) is adjacent to and beneath the membrane. Again countersinks 423 are seen, where the countersinks in the retentate member 422 and the permeate member 420 are coincident and configured to mate with threads or mating elements for the countersinks disposed on a reservoir assembly (not seen in FIG. 4A but see FIG. 4B).

A membrane or filter is disposed between the retentate and permeate members, where fluids can flow through the membrane but cells cannot and are thus retained in the flow channel disposed in the retentate member. Filters or membranes appropriate for use in the TFF device/module are those that are solvent resistant, are contamination free during filtration, and are able to retain the types and sizes of cells of interest. For example, in order to retain small cell types such as bacterial cells, pore sizes can be as low as 0.2 µm, however for other cell types, the pore sizes can be as high as 20 µm. Indeed, the pore sizes useful in the TFF device/module include filters with sizes from 0.20 µm, 0.21 µm, 0.22 µm, 0.23 µm, 0.24 µm, 0.25 µm, 0.26 µm, 0.27 µm, 0.28 µm, 0.29 µm, 0.30 µm, 0.31 µm, 0.32 µm, 0.33 µm, 0.34 µm, 0.35 µm, 0.36 µm, 0.37 µm, 0.38 µm, 0.39 µm, 0.40 µm, 0.41 µm, 0.42 µm, 0.43 µm, 0.44 µm, 0.45 µm, 0.46 µm, 0.47 µm, 0.48 µm, 0.49 µm, 0.50 µm and larger. The filters may be fabricated from any suitable non-reactive material including cellulose mixed ester (cellulose nitrate and acetate) (CME), polycarbonate (PC), polyvinylidene fluoride (PVDF), polyethersulfone (PES), polytetrafluoroethylene (PTFE), nylon, glass fiber, or metal substrates as in the case of laser or electrochemical etching.

The length of the channel structure 402 may vary depending on the volume of the cell culture to be grown and the optical density of the cell culture to be concentrated. The length of the channel structure typically is from 60 mm to 300 mm, or from 70 mm to 200 mm, or from 80 mm to 100 mm. The cross-section configuration of the flow channel 402 may be round, elliptical, oval, square, rectangular, trapezoidal, or irregular. If square, rectangular, or another shape with generally straight sides, the cross section may be from about 10 µm to 1000 µm wide, or from 200 µm to 800 µm wide, or from 300 µm to 700 µm wide, or from 400 µm to 600 µm wide; and from about 10 µm to 1000 µm high, or from 200 µm to 800 µm high, or from 300 µm to 700 µm high, or from 400 µm to 600 µm high. If the cross section of the flow channel 102 is generally round, oval or elliptical, the radius of the channel may be from about 50 µm to 1000 µm in hydraulic radius, or from 5 µm to 800 µm in hydraulic radius, or from 200 µm to 700 µm in hydraulic radius, or from 300 µm to 600 µm wide in hydraulic radius, or from about 200 to 500 µm in hydraulic radius. Moreover, the volume of the channel in the retentate 422 and permeate 420 members may be different depending on the depth of the channel in each member.

Figure 4B:
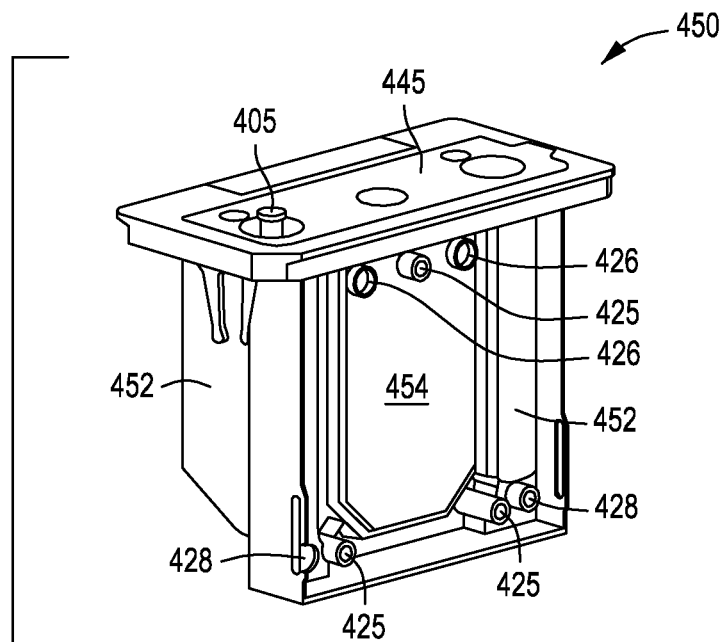
FIG. 4B depicts two side perspective views of a reservoir assembly of a tangential flow filtration module.
Figure 4B:
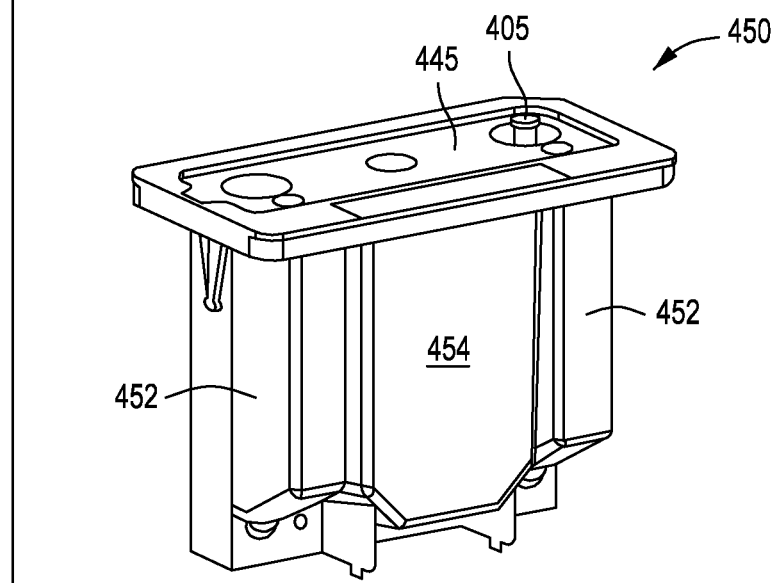

FIG. 4B shows front perspective (right) and rear perspective (left) views of a reservoir assembly 450 configured to be used with the tangential flow assembly 410 seen in FIG. 4A. Seen in the front perspective view (e.g., "front" being the side of reservoir assembly 450 that is coupled to the tangential flow assembly 410 seen in FIG. 4A) are retentate reservoirs 452 on either side of permeate reservoir 454. Also seen are permeate ports 426, retentate ports 428, and three threads or mating elements 425 for countersinks 423 (countersinks 423 not seen in this FIG. 4B). Threads or mating elements 425 for countersinks 423 are configured to mate or couple the tangential flow assembly 410 (seen in FIG. 4A) to reservoir assembly 450. Alternatively or in addition, fasteners, sonic welding or heat stakes may be used to mate or couple the tangential flow assembly 410 to reservoir assembly 450. In addition is seen gasket 445 covering the top of reservoir assembly 450. Gasket 445 is described in detail in relation to FIG. 4E and one reservoir has a pipette tip 405 inserted therein. At left in FIG. 4B is a rear perspective view of reservoir assembly 450, where "rear" is the side of reservoir assembly 450 that is not coupled to the tangential flow assembly. Seen are retentate reservoirs 452, permeate reservoir 454, gasket 445, and one reservoir has a pipette tip 405 inserted therein.

The TFF device may be fabricated from any robust material in which channels (and channel branches) may be milled including stainless steel, silicon, glass, aluminum, or plastics including cyclic-olefin copolymer (COC), cyclo-olefin polymer (COP), polystyrene, polyvinyl chloride, polyethylene, polyamide, polyethylene, polypropylene, acrylonitrile butadiene, polycarbonate, polyetheretheketone (PEEK), poly(methyl methylacrylate) (PMMA), polysulfone, and polyurethane, and co-polymers of these and other polymers. If the TFF device/module is disposable, preferably it is made of plastic. In some embodiments, the material used to fabricate the TFF device/module is thermally-conductive so that the cell culture may be heated or cooled to a desired temperature. In certain embodiments, the TFF device is formed by precision mechanical machining, laser machining, electro discharge machining (for metal devices); wet or dry etching (for silicon devices); dry or wet etching, powder or sandblasting, photostructuring (for glass devices); or thermoforming, injection molding, hot embossing, or laser machining (for plastic devices) using the materials mentioned above that are amenable to this mass production techniques.

Figure 4C:
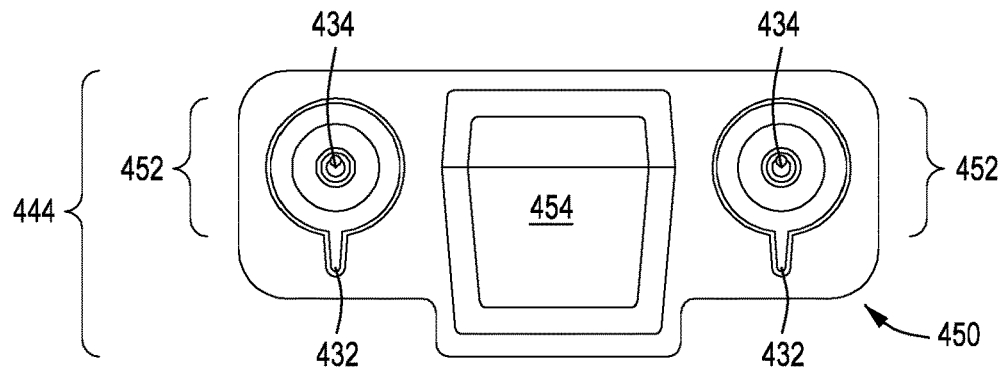
FIGS. 4C-4E depict an exemplary top, with fluidic and pneumatic ports and gasket suitable for the reservoir assemblies shown in FIG. 4B.
Figure 4D:
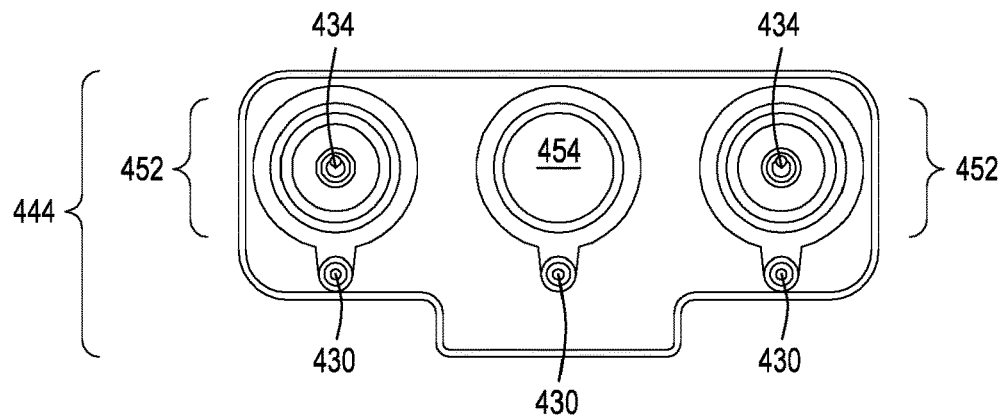
Figure 4E:
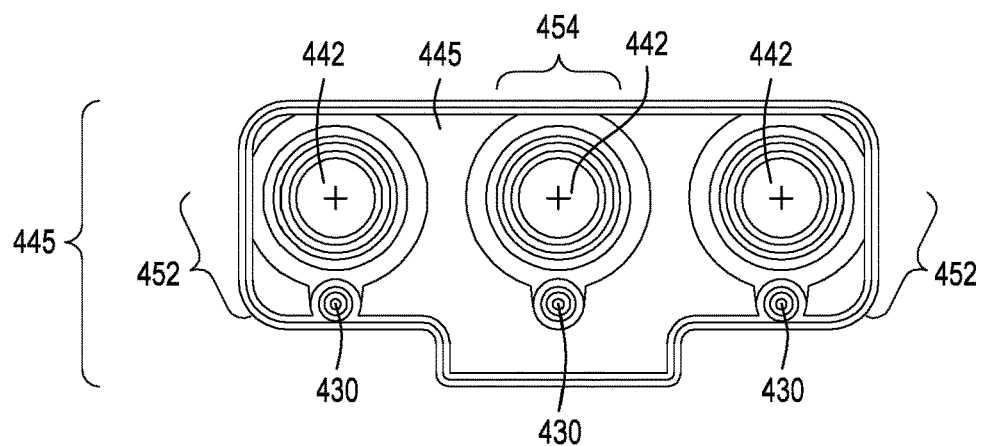

FIG. 4C depicts a top-down view of the reservoir assemblies 450 shown in FIG. 4B. FIG. 4D depicts a cover 444 for reservoir assembly 450 shown in FIGS. 4B and 4E depicts a gasket 445 that in operation is disposed on cover 444 of reservoir assemblies 450 shown in FIG. 4B. FIG. 4C is a top-down view of reservoir assembly 450, showing the tops of the two retentate reservoirs 452, one on either side of permeate reservoir 454. Also seen are grooves 432 that will mate with a pneumatic port (not shown), and fluid channels 434 that reside at the bottom of retentate reservoirs 452, which fluidically couple the retentate reservoirs 452 with the retentate ports 428 (not shown), via the through-holes for the retentate ports in permeate member 420 and membrane 424 (also not shown). FIG. 4D depicts a cover 444 that is configured to be disposed upon the top of reservoir assembly 450. Cover 444 has round cut-outs at the top of retentate reservoirs 452 and permeate/filtrate reservoir 454. Again, at the bottom of retentate reservoirs 452 fluid channels 434 can be seen, where fluid channels 434 fluidically couple retentate reservoirs 452 with the retentate ports 428 (not shown). Also shown are three pneumatic ports 430 for each retentate reservoir 452 and permeate/filtrate reservoir 454. FIG. 4E depicts a gasket 445 that is configures to be disposed upon the cover 444 of reservoir assembly 450. Seen are three fluid transfer ports 442 for each retentate reservoir 452 and for permeate/filtrate reservoir 454. Again, three pneumatic ports 430, for each retentate reservoir 452 and for permeate/filtrate reservoir 454, are shown.

The overall work flow for cell growth comprises loading a cell culture to be grown into a first retentate reservoir, optionally bubbling air or an appropriate gas through the cell culture, passing or flowing the cell culture through the first retentate port then tangentially through the TFF channel structure while collecting medium or buffer through one or both of the permeate ports 426, collecting the cell culture through a second retentate port 404 into a second retentate reservoir, optionally adding additional or different medium to the cell culture and optionally bubbling air or gas through the cell culture, then repeating the process, all while measuring, e.g., the optical density of the cell culture in the retentate reservoirs continuously or at desired intervals. Measurements of optical densities (OD) at programmed time intervals are accomplished using a 600 nm Light Emitting Diode (LED) that has been columnated through an optic into the retentate reservoir(s) containing the growing cells. The light continues through a collection optic to the detection system which consists of a (digital) gain-controlled silicone photodiode. Generally, optical density is shown as the absolute value of the logarithm with base 10 of the power transmission factors of an optical attenuator: OD=−log 10 (Power out/Power in). Since OD is the measure of optical attenuation—that is, the sum of absorption, scattering, and reflection—the TFF device OD measurement records the overall power transmission, so as the cells grow and become denser in population, the OD (the loss of signal) increases. The OD system is pre-calibrated against OD standards with these values stored in an on-board memory accessible by the measurement program.

In the channel structure, the membrane bifurcating the flow channels retains the cells on one side of the membrane (the retentate side 422) and allows unwanted medium or buffer to flow across the membrane into a filtrate or permeate side (e.g., permeate member 420) of the device. Bubbling air or other appropriate gas through the cell culture both aerates and mixes the culture to enhance cell growth. During the process, medium that is removed during the flow through the channel structure is removed through the permeate/filtrate ports 426. Alternatively, cells can be grown in one reservoir with bubbling or agitation without passing the cells through the TFF channel from one reservoir to the other.

The overall work flow for cell concentration using the TFF device/module involves flowing a cell culture or cell sample tangentially through the channel structure. As with the cell growth process, the membrane bifurcating the flow channels retains the cells on one side of the membrane and allows unwanted medium or buffer to flow across the membrane into a permeate/filtrate side (e.g., permeate member 420) of the device. In this process, a fixed volume of cells in medium or buffer is driven through the device until the cell sample is collected into one of the retentate ports 404, and the medium/buffer that has passed through the membrane is collected through one or both of the permeate/filtrate ports 426. All types of prokaryotic and eukaryotic cells—both adherent and non-adherent cells—can be grown in the TFF device. Adherent cells may be grown on beads or other cell scaffolds suspended in medium that flow through the TFF device.

The medium or buffer used to suspend the cells in the cell concentration device/module may be any suitable medium or buffer for the type of cells being transformed or transfected, such as LB, SOC, TPD, YPG, YPAD, MEM, DMEM, IMDM, RPMI, Hanks', PBS and Ringer's solution, where the media may be provided in a reagent cartridge as part of a kit. For culture of adherent cells, cells may be disposed on beads, microcarriers, or other type of scaffold suspended in medium. Most normal mammalian tissue-derived cells—except those derived from the hematopoietic system—are anchorage dependent and need a surface or cell culture support for normal proliferation. In the rotating growth vial described herein, microcarrier technology is leveraged. Microcarriers of particular use typically have a diameter of 100-300 µm and have a density slightly greater than that of the culture medium (thus facilitating an easy separation of cells and medium for, e.g., medium exchange) yet the density must also be sufficiently low to allow complete suspension of the carriers at a minimum stirring rate in order to avoid hydrodynamic damage to the cells. Many different types of microcarriers are available, and different microcarriers are optimized for different types of cells. There are positively charged carriers, such as Cytodex 1 (dextran-based, GE Healthcare), DE-52 (cellulose-based, Sigma-Aldrich Labware), DE-53 (cellulose-based, Sigma-Aldrich Labware), and HLX 11-170 (polystyrene-based); collagen- or ECM-(extracellular matrix) coated carriers, such as Cytodex 3 (dextran-based, GE Healthcare) or HyQ-sphere Pro-F 102-4 (polystyrene-based, Thermo Scientific); non-charged carriers, like HyQ-sphere P 102-4 (Thermo Scientific); or macroporous carriers based on gelatin (Cultisphere, Percell Biolytica) or cellulose (Cytopore, GE Healthcare).

In both the cell growth and concentration processes, passing the cell sample through the TFF device and collecting the cells in one of the retentate ports 404 while collecting the medium in one of the permeate/filtrate ports 426 is considered "one pass" of the cell sample. The transfer between retentate reservoirs "flips" the culture. The retentate and permeatee ports collecting the cells and medium, respectively, for a given pass reside on the same end of TFF device/module with fluidic connections arranged so that there are two distinct flow layers for the retentate and permeate/filtrate sides, but if the retentate port 404 resides on the retentate member of device/module (that is, the cells are driven through the channel above the membrane and the filtrate (medium) passes to the portion of the channel below the membrane), the permeate/filtrate port 426 will reside on the permeate member of device/module and vice versa (that is, if the cell sample is driven through the channel below the membrane, the filtrate (medium) passes to the portion of the channel above the membrane). Due to the high pressures used to transfer the cell culture and fluids through the flow channel of the TFF device, the effect of gravity is negligible.

At the conclusion of a "pass" in either of the growth and concentration processes, the cell sample is collected by passing through the retentate port 404 and into the retentate reservoir (not shown). To initiate another "pass", the cell sample is passed again through the TFF device, this time in a flow direction that is reversed from the first pass. The cell sample is collected by passing through the retentate port 404 and into retentate reservoir (not shown) on the opposite end of the device/module from the retentate port 404 that was used to collect cells during the first pass. Likewise, the medium/buffer that passes through the membrane on the second pass is collected through the permeate port 426 on the opposite end of the device/module from the permeate port 426 that was used to collect the filtrate during the first pass, or through both ports. This alternating process of passing the retentate (the concentrated cell sample) through the device/module is repeated until the cells have been grown to a desired optical density, and/or concentrated to a desired volume, and both permeate ports (i.e., if there are more than one) can be open during the passes to reduce operating time. In addition, buffer exchange may be effected by adding a desired buffer (or fresh medium) to the cell sample in the retentate reservoir, before initiating another "pass", and repeating this process until the old medium or buffer is diluted and filtered out and the cells reside in fresh medium or buffer. Note that buffer exchange and cell growth may (and typically do) take place simultaneously, and buffer exchange and cell concentration may (and typically do) take place simultaneously. For further information and alternative embodiments on TFFs see, e.g., U.S. Ser. No. 62/728,365, filed 7 Sep. 2018; 62/857,599, filed 5 Jun. 2019; and 62/867,415, filed 27 Jun. 2019.

The Cell Transformation Module

Figure 5A:
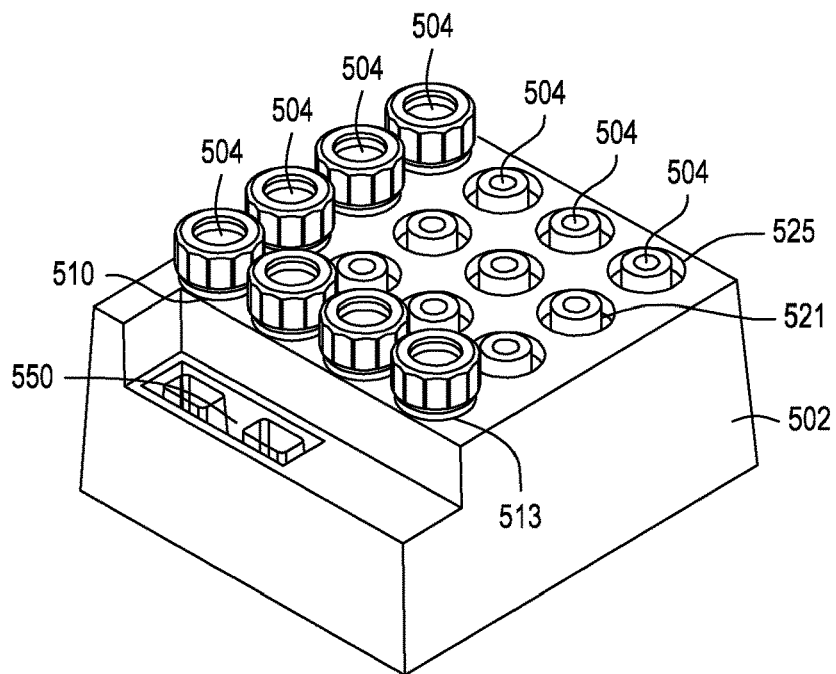
FIG. 5A depicts an exemplary combination reagent cartridge and electroporation device (e.g., transformation module) that may be used in a multi-module cell processing instrument.

FIG. 5A depicts an exemplary combination reagent cartridge and electroporation device ("cartridge") that may be used in an automated multi-module cell processing instrument along with the TFF module. In addition, in certain embodiments the material used to fabricate the cartridge is thermally-conductive, as in certain embodiments the cartridge contacts a thermal device (not shown), such as a Peltier device or thermoelectric cooler, that heats or cools reagents in the reagent reservoirs or reservoirs 510, 513, 521, 525. Reagent reservoirs or reservoirs 510, 513, 521, 525 may be reservoirs into which individual tubes 504 of reagents are inserted as shown in FIG. 5A, or the reagent reservoirs may hold the reagents without inserted tubes. Additionally, the reservoirs 510, 513, 521, 525 in a reagent cartridge may be configured for any combination of tubes, co-joined tubes, and direct-fill of reagents.

In one embodiment, the reagent reservoirs or reservoirs 504 of reagent cartridge are configured to hold various size tubes, including, e.g., 250 ml tubes, 25 ml tubes, 10 ml tubes, 5 ml tubes, and Eppendorf or microcentrifuge tubes. In yet another embodiment, all reservoirs may be configured to hold the same size tube, e.g., 5 ml tubes, and reservoir inserts may be used to accommodate smaller tubes in the reagent reservoir. In yet another embodiment—particularly in an embodiment where the reagent cartridge is disposable—the reagent reservoirs hold reagents without inserted tubes. In this disposable embodiment, the reagent cartridge may be part of a kit, where the reagent cartridge is pre-filled with reagents and the receptacles or reservoirs sealed with, e.g., foil, heat seal acrylic or the like and presented to a consumer where the reagent cartridge can then be used in an automated multi-module cell processing instrument. As one of ordinary skill in the art will appreciate given the present disclosure, the reagents contained in the reagent cartridge will vary depending on work flow; that is, the reagents will vary depending on the processes to which the cells are subjected in the automated multi-module cell processing instrument, e.g., protein production, cell transformation and culture, cell editing, etc.

Reagents such as cell samples, enzymes, buffers, nucleic acid vectors, expression cassettes, proteins or peptides, reaction components (such as, e.g., $MgCl_2$, dNTPs, nucleic acid assembly reagents, gap repair reagents, and the like), wash solutions, ethanol, and magnetic beads for nucleic acid purification and isolation, etc. may be positioned in the reagent cartridge at a known position. In some embodiments of the cartridge, the cartridge comprises a script (not shown) readable by a processor (not shown) for dispensing the reagents. Also, the cartridge as one component in an automated multi-module cell processing instrument may comprise a script specifying two, three, four, five, ten or more processes to be performed by the automated multi-module cell processing instrument. In certain embodiments, the reagent cartridge is disposable and is pre-packaged with reagents tailored to performing specific cell processing protocols, e.g., genome editing or protein production. Because the reagent cartridge contents vary while components/modules of the automated multi-module cell processing instrument or system may not, the script associated with a particular reagent cartridge matches the reagents used and cell processes performed. Thus, e.g., reagent cartridges may be pre-packaged with reagents for genome editing and a script that specifies the process steps for performing genome editing in an automated multi-module cell processing instrument, or, e.g., reagents for protein expression and a script that specifies the process steps for performing protein expression in an automated multi-module cell processing instrument.

For example, the reagent cartridge may comprise a script to pipette competent cells from a reservoir, transfer the cells to a transformation module, pipette a nucleic acid solution comprising a vector with expression cassette from another reservoir in the reagent cartridge, transfer the nucleic acid solution to the transformation module, initiate the transformation process for a specified time, then move the transformed cells to yet another reservoir in the reagent cassette or to another module such as a cell growth module in the automated multi-module cell processing instrument. In another example, the reagent cartridge may comprise a script to transfer a nucleic acid solution comprising a vector from a reservoir in the reagent cassette, nucleic acid solution comprising editing oligonucleotide cassettes in a reservoir in the reagent cassette, and a nucleic acid assembly mix from another reservoir to the nucleic acid assembly/desalting module, if present. The script may also specify process steps performed by other modules in the automated multi-module cell processing instrument. For example, the script may specify that the nucleic acid assembly/desalting reservoir be heated to 50° C. for 30 min to generate an assembled product; and desalting and resuspension of the assembled product via magnetic bead-based nucleic acid purification involving a series of pipette transfers and mixing of magnetic beads, ethanol wash, and buffer.

As described in relation to FIGS. 5B and 5C below, the exemplary reagent cartridges for use in the automated multi-module cell processing instruments may include one or more electroporation devices, preferably flow-through electroporation (FTEP) devices. In yet other embodiments, the reagent cartridge is separate from the transformation module. Electroporation is a widely-used method for permeabilization of cell membranes that works by temporarily generating pores in the cell membranes with electrical stimulation. Applications of electroporation include the delivery of DNA, RNA, siRNA, peptides, proteins, antibodies, drugs or other substances to a variety of cells such as mammalian cells (including human cells), plant cells, archea, yeasts, other eukaryotic cells, bacteria, and other cell types. Electrical stimulation may also be used for cell fusion in the production of hybridomas or other fused cells. During a typical electroporation procedure, cells are suspended in a buffer or medium that is favorable for cell survival. For bacterial cell electroporation, low conductance mediums, such as water, glycerol solutions and the like, are often used to reduce the heat production by transient high current. In traditional electroporation devices, the cells and material to be electroporated into the cells (collectively "the cell sample") are placed in a cuvette embedded with two flat electrodes for electrical discharge. For example, Bio-Rad (Hercules, Calif.) makes the GENE PULSER XCELL™ line of products to electroporate cells in cuvettes. Traditionally, electroporation requires high field strength; however, the flow-through electroporation devices included in the reagent cartridges achieve high efficiency cell electroporation with low toxicity. The reagent cartridges of the disclosure allow for particularly easy integration with robotic liquid handling instrumentation that is typically used in automated instruments and systems such as air displacement pipettors. Such automated instrumentation includes, but is not limited to, off-the-shelf automated liquid handling systems from Tecan (Mannedorf, Switzerland), Hamilton (Reno, Nev.), Beckman Coulter (Fort Collins, Colo.), etc.

Figure 5B:
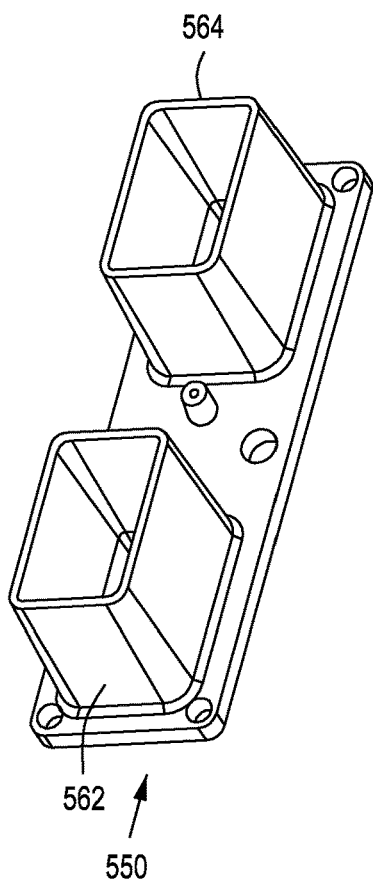
FIG. 5B is a top perspective view of one embodiment of an exemplary flow-through electroporation device that may be part of a reagent cartridge.
Figure 5C:
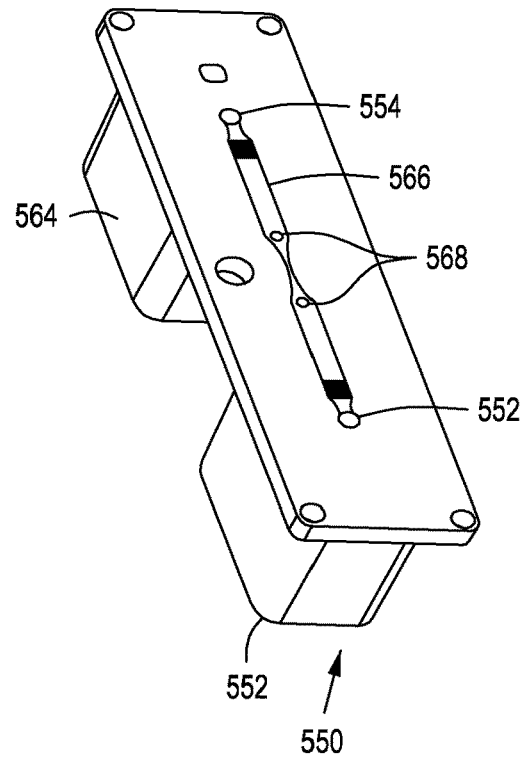
FIG. 5C depicts a bottom perspective view of one embodiment of an exemplary flow-through electroporation device that may be part of a reagent cartridge.

FIGS. 5B and 5C are top perspective and bottom perspective views, respectively, of an exemplary FTEP device 550 that may be part of (e.g., a component in) the reagent cartridge in FIG. 5A or may be a stand-alone module; that is, not a part of a reagent cartridge or other module. FIG. 5B depicts an FTEP device 550. The FTEP device 550 has wells that define cell sample inlets 552 and cell sample outlets 554. FIG. 5C is a bottom perspective view of the FTEP device 550 of FIG. 5B. An inlet well 552 and an outlet well 554 can be seen in this view. Also seen in FIG. 5C are the bottom of an inlet 562 corresponding to well 552, the bottom of an outlet 564 corresponding to the outlet well 554, the bottom of a defined flow channel 566 and the bottom of two electrodes 568 on either side of flow channel 566. The FTEP devices may comprise push-pull pneumatic means to allow multi-pass electroporation procedures; that is, cells to be electroporated may be "pulled" from the inlet toward the outlet for one pass of electroporation, then be "pushed" from the outlet end of the FTEP device toward the inlet end to pass between the electrodes again for another pass of electroporation. Further, this process may be repeated one to many times. For additional information regarding FTEP devices, see, e.g., U.S. Pat. No. 10,435,713, issued 8 Oct. 2019; U.S. Pat. No. 10,443,074, issued 15 Oct. 2019; U.S. Pat. No. 10,323,258, issued 18 Jun. 2019; U.S. Pat. No. 10,508,288, issued 17 Dec. 2019; U.S. Pat. No. 10,415,058, issued 17 Sep. 2019; and U.S. Ser. No. 16/550,790, filed 26 Aug. 2019; and Ser. No. 16/571,080, filed 14 Sep. 2019. Further, other embodiments of the reagent cartridge may provide or accommodate electroporation devices that are not configured as FTEP devices, such as those described in U.S. Ser. No. 16/109,156, filed 22 Aug. 2018. For reagent cartridges useful in the present automated multi-module cell processing instruments, see, e.g., U.S. Pat. No. 10,376,889, issued 13 Aug. 2019; U.S. Pat. No. 10,406,525, issued 10 Sep. 2019; U.S. Pat. No. 10,478,822, issued 19 Nov. 2019; U.S. Pat. No. 10,576,474, issued 3 Feb. 2020; and U.S. Ser. No. 16/749,757, filed 22 Jan. 2020.

Figure 5D:
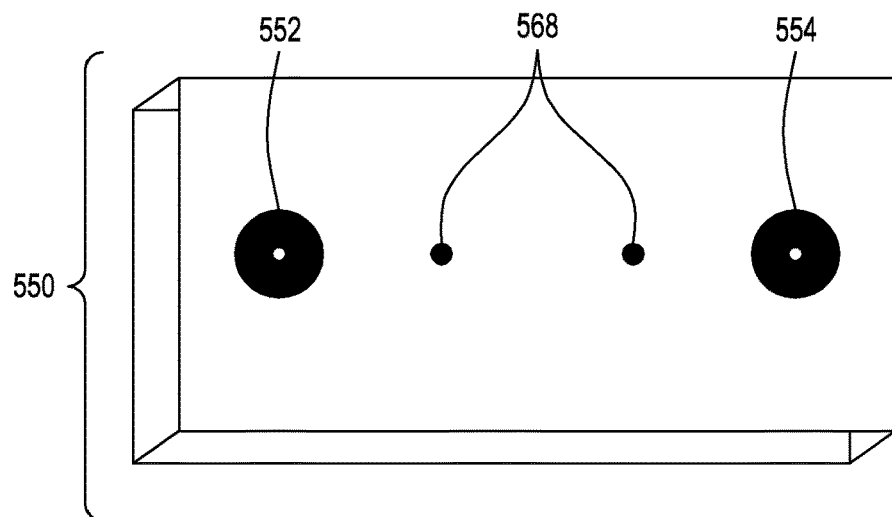
FIGS. 5D-5F depict a top perspective view, a top view of a cross section, and a side perspective view of a cross section of an FTEP device useful in a multi-module automated cell processing instrument such as that shown in FIGS. 2A-2C.
Figure 5E:
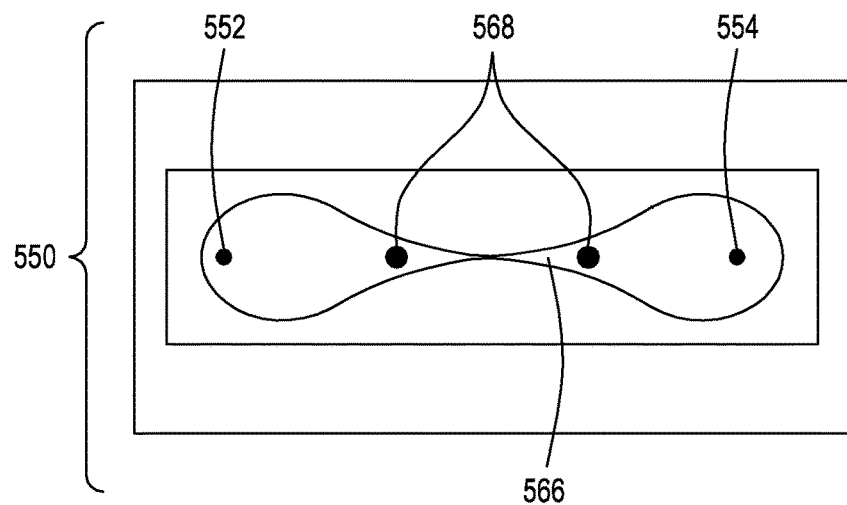
Figure 5F:
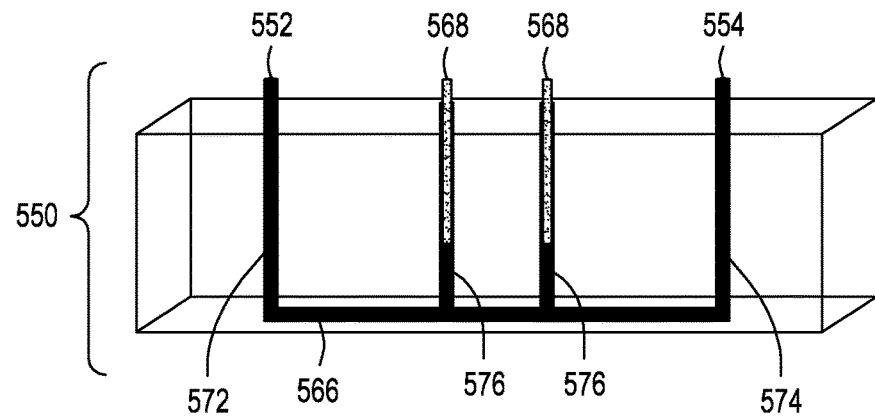

Additional details of the FTEP devices are illustrated in FIGS. 5D-5F. Note that in the FTEP devices in FIGS. 5D-5F the electrodes are placed such that a first electrode is placed between an inlet and a narrowed region of the flow channel, and the second electrode is placed between the narrowed region of the flow channel and an outlet. FIG. 5D shows a top planar view of an FTEP device 550 having an inlet 552 for introducing a fluid containing cells and exogenous material into FTEP device 550 and an outlet 554 for removing the transformed cells from the FTEP following electroporation. The electrodes 568 are introduced through channels (not shown) in the device. FIG. 5E shows a cutaway view from the top of the FTEP device 550, with the inlet 552, outlet 554, and electrodes 568 positioned with respect to a flow channel 566. FIG. 5F shows a side cutaway view of FTEP device 550 with the inlet 552 and inlet channel 572, and outlet 554 and outlet channel 574. The electrodes 568 are positioned in electrode channels 576 so that they are in fluid communication with the flow channel 566, but not directly in the path of the cells traveling through the flow channel 566. Note that the first electrode is placed between the inlet and the narrowed region of the flow channel, and the second electrode is placed between the narrowed region of the flow channel and the outlet. The electrodes 568 in this aspect of the device are positioned in the electrode channels 576 which are generally perpendicular to the flow channel 566 such that the fluid containing the cells and exogenous material flows from the inlet channel 572 through the flow channel 566 to the outlet channel 574, and in the process fluid flows into the electrode channels 576 to be in contact with the electrodes 568. In this aspect, the inlet channel, outlet channel and electrode channels all originate from the same planar side of the device. In certain aspects, however, the electrodes may be introduced from a different planar side of the FTEP device than the inlet and outlet channels.

In the FTEP devices of the disclosure, the toxicity level of the transformation results in greater than 30% viable cells after electroporation, preferably greater than 35%, 40%, 45%, 50%, 55%, 60%, 70%, 75%, 80%, 85%, 90%, 95% or even 99% viable cells following transformation, depending on the cell type and the nucleic acids being introduced into the cells.

The housing of the FTEP device can be made from many materials depending on whether the FTEP device is to be reused, autoclaved, or is disposable, including stainless steel, silicon, glass, resin, polyvinyl chloride, polyethylene, polyamide, polystyrene, polyethylene, polypropylene, acrylonitrile butadiene, polycarbonate, polyetheretheketone (PEEK), polysulfone and polyurethane, co-polymers of these and other polymers. Similarly, the walls of the channels in the device can be made of any suitable material including silicone, resin, glass, glass fiber, polyvinyl chloride, polyethylene, polyamide, polyethylene, polypropylene, acrylonitrile butadiene, polycarbonate, polyetheretheketone (PEEK), polysulfone and polyurethane, co-polymers of these and other polymers. Preferred materials include crystal styrene, cyclo-olefin polymer (COP) and cyclic olephin co-polymers (COC), which allow the device to be formed entirely by injection molding in one piece with the exception of the electrodes and, e.g., a bottom sealing film if present.

The FTEP devices described herein (or portions of the FTEP devices) can be created or fabricated via various techniques, e.g., as entire devices or by creation of structural layers that are fused or otherwise coupled. For example, for metal FTEP devices, fabrication may include precision mechanical machining or laser machining; for silicon FTEP devices, fabrication may include dry or wet etching; for glass FTEP devices, fabrication may include dry or wet etching, powderblasting, sandblasting, or photostructuring; and for plastic FTEP devices fabrication may include thermoforming, injection molding, hot embossing, or laser machining. The components of the FTEP devices may be manufactured separately and then assembled, or certain components of the FTEP devices (or even the entire FTEP device except for the electrodes) may be manufactured (e.g., using 3D printing) or molded (e.g., using injection molding) as a single entity, with other components added after molding. For example, housing and channels may be manufactured or molded as a single entity, with the electrodes later added to form the FTEP unit. Alternatively, the FTEP device may also be formed in two or more parallel layers, e.g., a layer with the horizontal channel and filter, a layer with the vertical channels, and a layer with the inlet and outlet ports, which are manufactured and/or molded individually and assembled following manufacture.

In specific aspects, the FTEP device can be manufactured using a circuit board as a base, with the electrodes, filter and/or the flow channel formed in the desired configuration on the circuit board, and the remaining housing of the device containing, e.g., the one or more inlet and outlet channels and/or the flow channel formed as a separate layer that is then sealed onto the circuit board. The sealing of the top of the housing onto the circuit board provides the desired configuration of the different elements of the FTEP devices of the disclosure. Also, two to many FTEP devices may be manufactured on a single substrate, then separated from one another thereafter or used in parallel. In certain embodiments, the FTEP devices are reusable and, in some embodiments, the FTEP devices are disposable. In additional embodiments, the FTEP devices may be autoclavable.

The electrodes 508 can be formed from any suitable metal, such as copper, stainless steel, titanium, aluminum, brass, silver, rhodium, gold or platinum, or graphite. One preferred electrode material is alloy 303 (UNS330300) austenitic stainless steel. An applied electric field can destroy electrodes made from of metals like aluminum. If a multiple-use (i.e., non-disposable) flow-through FTEP device is desired—as opposed to a disposable, one-use flow-through FTEP device—the electrode plates can be coated with metals resistant to electrochemical corrosion. Conductive coatings like noble metals, e.g., gold, can be used to protect the electrode plates.

As mentioned, the FTEP devices may comprise push-pull pneumatic means to allow multi-pass electroporation procedures; that is, cells to electroporated may be "pulled" from the inlet toward the outlet for one pass of electroporation, then be "pushed" from the outlet end of the flow-through FTEP device toward the inlet end to pass between the electrodes again for another pass of electroporation. This process may be repeated one to many times.

Depending on the type of cells to be electroporated (e.g., bacterial, yeast, mammalian) and the configuration of the electrodes, the distance between the electrodes in the flow channel can vary widely. For example, where the flow channel decreases in width, the flow channel may narrow to between 10 μm and 5 mm, or between 25 μm and 3 mm, or between 50 μm and 2 mm, or between 75 μm and 1 mm. The distance between the electrodes in the flow channel may be between 1 mm and 10 mm, or between 2 mm and 8 mm, or between 3 mm and 7 mm, or between 4 mm and 6 mm. The overall size of the FTEP device may be from 3 cm to 15 cm in length, or 4 cm to 12 cm in length, or 4.5 cm to 10 cm in length. The overall width of the FTEP device may be from 0.5 cm to 5 cm, or from 0.75 cm to 3 cm, or from 1 cm to 2.5 cm, or from 1 cm to 1.5 cm.

The region of the flow channel that is narrowed is wide enough so that at least two cells can fit in the narrowed portion side-by-side. For example, a typical bacterial cell is 1 μm in diameter; thus, the narrowed portion of the flow channel of the FTEP device used to transform such bacterial cells will be at least 2 μm wide. In another example, if a mammalian cell is approximately 50 μm in diameter, the narrowed portion of the flow channel of the FTEP device used to transform such mammalian cells will be at least 100 μm wide. That is, the narrowed portion of the FTEP device will not physically contort or "squeeze" the cells being transformed.

In embodiments of the FTEP device where reservoirs are used to introduce cells and exogenous material into the FTEP device, the reservoirs range in volume from 100 μL, to 10 mL, or from 500 μL, to 75 mL, or from 1 mL to 5 mL. The flow rate in the FTEP ranges from 0.1 mL to 5 mL per minute, or from 0.5 mL to 3 mL per minute, or from 1.0 mL to 2.5 mL per minute. The pressure in the FTEP device ranges from 1-30 psi, or from 2-10 psi, or from 3-5 psi.

To avoid different field intensities between the electrodes, the electrodes should be arranged in parallel. Furthermore, the surface of the electrodes should be as smooth as possible without pin holes or peaks. Electrodes having a roughness Rz of 1 to 10 μm are preferred. In another embodiment of the invention, the flow-through electroporation device comprises at least one additional electrode which applies a ground potential to the FTEP device.

Cell Singulation and Enrichment Device

Figure 6A:
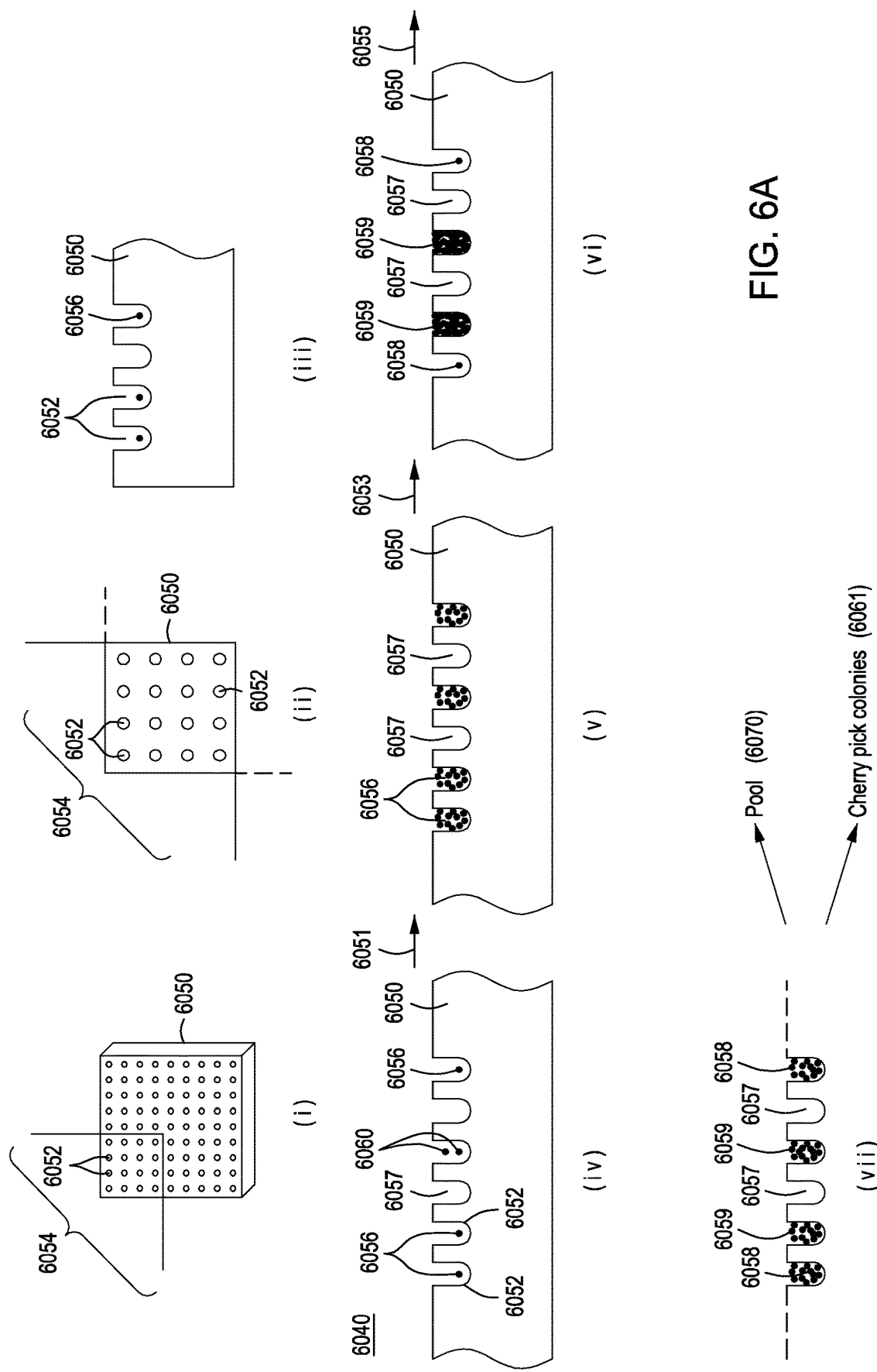
FIG. 6A depicts a simplified graphic of a workflow for singulating, editing and normalizing cells in a solid wall device.

FIG. 6A depicts a solid wall device 6050 and a workflow for singulating cells in microwells in the solid wall device. At the top left of the figure (i), there is depicted solid wall device 6050 with microwells 6052. A section 6054 of substrate 6050 is shown at (ii), also depicting microwells 6052. At (iii), a side cross-section of solid wall device 6050 is shown, and microwells 6052 have been loaded, where, in this embodiment, Poisson or substantial Poisson loading has taken place; that is, each microwell has one or no cells, and the likelihood that any one microwell has more than one cell is low. At (iv), workflow 6040 is illustrated where substrate 6050 having microwells 6052 shows microwells 6056 with one cell per microwell, microwells 6057 with no cells in the microwells, and one microwell 6060 with two cells in the microwell. In step 6051, the cells in the microwells are allowed to double approximately 2-150 times to form clonal colonies (v), then editing is allowed to occur 6053. Shown are microwells 6057 where no cells were distributed in a well and wells 6056 where a single cell was distributed in the well.

After editing 6053, many cells in the colonies of cells that have been edited die as a result of the double-strand cuts caused by active editing and there is a lag in growth for the edited cells that do survive but must repair and recover following editing (microwells 6058), where cells that do not undergo editing thrive (microwells 6059) (vi). All cells are allowed to continue grow 6055 to establish colonies and normalize, where the colonies of edited cells in microwells 6058 catch up in size and/or cell number with the cells in microwells 6059 that do not undergo editing (vii). Once the cell colonies are normalized, either pooling 6070 of all cells in the microwells can take place, in which case the cells are enriched for edited cells by eliminating the bias from non-editing cells and fitness effects from editing; alternatively, colony growth in the microwells is monitored after editing, and slow growing colonies (e.g., the cells in microwells 6058) are identified and selected 6061 (e.g., "cherry picked") resulting in even greater enrichment of edited cells.

In growing the cells, the medium used will depend, of course, on the type of cells being edited—e.g., bacterial, yeast or mammalian. For example, medium for yeast cell growth includes LB, SOC, TPD, YPG, YPAD, MEM and DMEM.

Figure 6B:
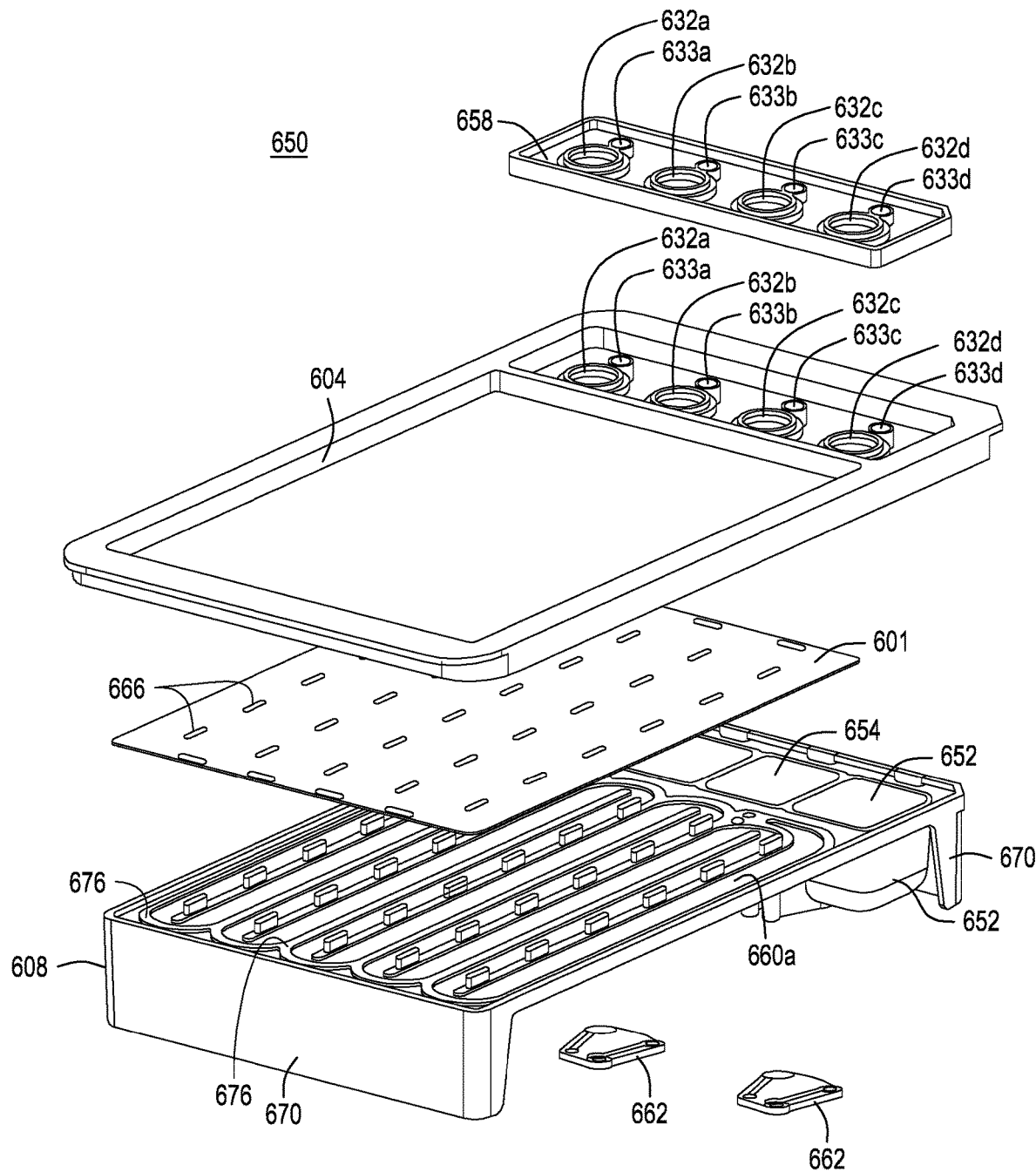
FIGS. 6B-6D depict an embodiment of a solid wall isolation incubation and normalization (SWIIN) module.

A module useful for performing the method depicted in FIG. 6A is a solid wall isolation, incubation, and normalization (SWIIN) module. FIG. 6B depicts an embodiment of a SWIIN module 650 from an exploded top perspective view. In SWIIN module 650 the retentate member is formed on the bottom of a top of a SWIIN module component and the permeate member is formed on the top of the bottom of a SWIIN module component.

The SWIIN module 650 in FIG. 6B comprises from the top down, a reservoir gasket or cover 658, a retentate member 604 (where a retentate flow channel cannot be seen in this FIG. 6B), a perforated member 601 swaged with a filter (filter not seen in FIG. 6B), a permeate member 608 comprising integrated reservoirs (permeate reservoirs 652 and retentate reservoirs 654), and two reservoir seals 662, which seal the bottom of permeate reservoirs 652 and retentate reservoirs 654. A permeate channel 660a can be seen disposed on the top of permeate member 608, defined by a raised portion 676 of serpentine channel 660a, and ultrasonic tabs 664 (not shown in this FIG. 6B, but see FIG. 6C) can be seen disposed on the top of permeate member 608 as well. The perforations that form the wells on perforated member 601 are not seen in this FIG. 6B; however, through-holes 666 to accommodate the ultrasonic tabs 664 are seen. In addition, supports 670 are disposed at either end of SWIIN module 650 to support SWIIN module 650 and to elevate permeate member 608 and retentate member 604 above reservoirs 652 and 654 to minimize bubbles or air entering the fluid path from the permeate reservoir to serpentine channel 660a or the fluid path from the retentate reservoir to serpentine channel 660b (neither fluid path is seen in this FIG. 6B).

In this FIG. 6B, it can be seen that the serpentine channel 660a that is disposed on the top of permeate member 608 traverses permeate member 608 for most of the length of permeate member 608 except for the portion of permeate member 608 that comprises permeate reservoirs 652 and retentate reservoirs 654 and for most of the width of permeate member 608. As used herein with respect to the distribution channels in the retentate member or permeate member, "most of the length" means about 95% of the length of the retentate member or permeate member, or about 90%, 85%, 80%, 75%, or 70% of the length of the retentate member or permeate member. As used herein with respect to the distribution channels in the retentate member or permeate member, "most of the width" means about 95% of the width of the retentate member or permeate member, or about 90%, 85%, 80%, 75%, or 70% of the width of the retentate member or permeate member.

In this embodiment of a SWIIN module, the perforated member includes through-holes to accommodate ultrasonic tabs disposed on the permeate member. Thus, in this embodiment the perforated member is fabricated from 316 stainless steel, and the perforations form the walls of microwells while a filter or membrane is used to form the bottom of the microwells. Typically, the perforations (microwells) are approximately 150 μm-200 μm in diameter, and the perforated member is approximately 125 μm deep, resulting in microwells having a volume of approximately 2.5 nl, with a total of approximately 200,000 microwells. The distance between the microwells is approximately 279 µm center-to-center. Though here the microwells have a volume of approximately 2.5 nl, the volume of the microwells may be from 1 to 25 nl, or preferably from 2 to 10 nl, and even more preferably from 2 to 4 nl. As for the filter or membrane, like the filter described previously, filters appropriate for use are solvent resistant, contamination free during filtration, and are able to retain the types and sizes of cells of interest. For example, in order to retain small cell types such as bacterial cells, pore sizes can be as low as 0.10 µm, however for other cell types (e.g., such as for mammalian cells), the pore sizes can be as high as 10.0 µm-20.0 µm or more. Indeed, the pore sizes useful in the cell concentration device/module include filters with sizes from 0.10 µm, 0.11 µm, 0.12 µm, 0.13 µm, 0.14 µm, 0.15 µm, 0.16 µm, 0.17 µm, 0.18 µm, 0.19 µm, 0.20 µm, 0.21 µm, 0.22 µm, 0.23 µm, 0.24 µm, 0.25 µm, 0.26 µm, 0.27 µm, 0.28 µm, 0.29 µm, 0.30 µm, 0.31 µm, 0.32 µm, 0.33 µm, 0.34 µm, 0.35 µm, 0.36 µm, 0.37 µm, 0.38 µm, 0.39 µm, 0.40 µm, 0.41 µm, 0.42 µm, 0.43 µm, 0.44 µm, 0.45 µm, 0.46 µm, 0.47 µm, 0.48 µm, 0.49 µm, 0.50 µm and larger. The filters may be fabricated from any suitable material including cellulose mixed ester (cellulose nitrate and acetate) (CME), polycarbonate (PC), polyvinylidene fluoride (PVDF), polyethersulfone (PES), polytetrafluoroethylene (PTFE), nylon, or glass fiber.

The cross-section configuration of the mated serpentine channel may be round, elliptical, oval, square, rectangular, trapezoidal, or irregular. If square, rectangular, or another shape with generally straight sides, the cross section may be from about 2 mm to 15 mm wide, or from 3 mm to 12 mm wide, or from 5 mm to 10 mm wide. If the cross section of the mated serpentine channel is generally round, oval or elliptical, the radius of the channel may be from about 3 mm to 20 mm in hydraulic radius, or from 5 mm to 15 mm in hydraulic radius, or from 8 mm to 12 mm in hydraulic radius.

Serpentine channels 660a (seen) and the counterpart 660b (not seen but would be disposed on the bottom of retentate member 604) can have approximately the same volume or a different volume. For example, each "side" or portion 660a, 660b of the serpentine channel may have a volume of, e.g., 2 mL, or serpentine channel 660a of permeate member 608 may have a volume of 2 mL, and the serpentine channel 660b of retentate member 604 may have a volume of, e.g., 3 mL. The volume of fluid in the serpentine channel may range from about 2 mL to about 80 mL, or about 4 mL to 60 mL, or from 5 mL to 40 mL, or from 6 mL to 20 mL (note these volumes apply to a SWIIN module comprising a, e.g., 50-500K perforation member). The volume of the reservoirs may range from 5 mL to 50 mL, or from 7 mL to 40 mL, or from 8 mL to 30 mL or from 10 mL to 20 mL, and the volumes of all reservoirs may be the same or the volumes of the reservoirs may differ (e.g., the volume of the permeate reservoirs is greater than that of the retentate reservoirs).

The serpentine channel portions 660a (seen) and the counterpart 660b (not seen but would be disposed on the bottom of retentate member 604) of the permeate member 608 and retentate member 604, respectively, are approximately 200 mm long, 130 mm wide, and 4 mm thick, though in other embodiments, the retentate and permeate members can be from 75 mm to 400 mm in length, or from 100 mm to 300 mm in length, or from 150 mm to 250 mm in length; from 50 mm to 250 mm in width, or from 75 mm to 200 mm in width, or from 100 mm to 150 mm in width; and from 2 mm to 15 mm in thickness, or from 4 mm to 10 mm in thickness, or from 5 mm to 8 mm in thickness. Embodiments the retentate (and permeate) members may be fabricated from PMMA (poly(methyl methacrylate) or other materials may be used, including polycarbonate, cyclic olefin copolymer (COC), glass, polyvinyl chloride, polyethylene, polyamide, polypropylene, polysulfone, polyurethane, and co-polymers of these and other polymers. Preferably at least the retentate member is fabricated from a transparent material so that the cells can be visualized (see, e.g., FIG. 6E and the description thereof). For example, a video camera may be used to monitor cell growth by, e.g., density change measurements based on an image of an empty well, with phase contrast, or if, e.g., a chromogenic marker, such as a chromogenic protein, is used to add a distinguishable color to the cells. Chromogenic markers such as blitzen blue, dreidel teal, virginia violet, vixen purple, prancer purple, tinsel purple, maccabee purple, donner magenta, cupid pink, seraphina pink, scrooge orange, and leor orange (the Chromogenic Protein Paintbox, all available from ATUM (Newark, Calif.)) obviate the need to use fluorescence, although fluorescent cell markers, fluorescent proteins, and chemiluminescent cell markers may also be used.

Because the retentate member preferably is transparent, colony growth in the SWIIN module can be monitored by automated devices such as those sold by JoVE (ScanLag™ system, Cambridge, Mass.) (also see Levin-Reisman, et al., Nature Methods, 7:737-39 (2010)). Cell growth for, e.g., mammalian cells may be monitored by, e.g., the growth monitor sold by IncuCyte (Ann Arbor, Mich.) (see also, Choudhry, PLos One, 11(2):e0148469 (2016)). Further, automated colony pickers may be employed, such as those sold by, e.g., TECAN (Pickolo™ system, Mannedorf, Switzerland); Hudson Inc. (RapidPick™, Springfield, N.J.); Molecular Devices (QPix 400™ system, San Jose, Calif.); and Singer Instruments (PIXL™ system, Somerset, UK).

Due to the heating and cooling of the SWIIN module, condensation may accumulate on the retentate member which may interfere with accurate visualization of the growing cell colonies. Condensation of the SWIIN module 650 may be controlled by, e.g., moving heated air over the top of (e.g., retentate member) of the SWIIN module 650, or by applying a transparent heated lid over at least the serpentine channel portion 660b of the retentate member 604. See, e.g., FIG. 6E and the description thereof infra.

In SWIIN module 650 cells and medium—at a dilution appropriate for Poisson or substantial Poisson distribution of the cells in the microwells of the perforated member—are flowed into serpentine channel 660b from ports in retentate member 604, and the cells settle in the microwells while the medium passes through the filter into serpentine channel 660a in permeate member 608. The cells are retained in the microwells of perforated member 601 as the cells cannot travel through the filter. Appropriate medium may be introduced into permeate member 608 through permeate ports (not seen). The medium flows upward through filter (not seen) to nourish the cells in the microwells (perforations) of perforated member 601. Additionally, buffer exchange can be effected by cycling medium through the retentate and permeate members. In operation, the cells are deposited into the microwells, are grown for an initial, e.g., 2-100 doublings, editing is induced by, e.g., raising the temperature of the SWIIN to 42° C. to induce a temperature inducible promoter or by removing growth medium from the permeate member and replacing the growth medium with a medium comprising a chemical component that induces an inducible promoter.

Once editing has taken place, the temperature of the SWIIN may be decreased, or the inducing medium may be removed and replaced with fresh medium lacking the chemical component thereby de-activating the inducible promoter. The cells then continue to grow in the SWIIN module 650 until the growth of the cell colonies in the microwells is normalized. For the normalization protocol, once the colonies are normalized, the colonies are flushed from the microwells by applying fluid or air pressure (or both) to the permeate member serpentine channel 660a and thus to the filter (not seen) and pooled. Alternatively, if cherry picking is desired, the growth of the cell colonies in the microwells is monitored, and slow-growing colonies are directly selected; or, fast-growing colonies are eliminated.

Figure 6C:
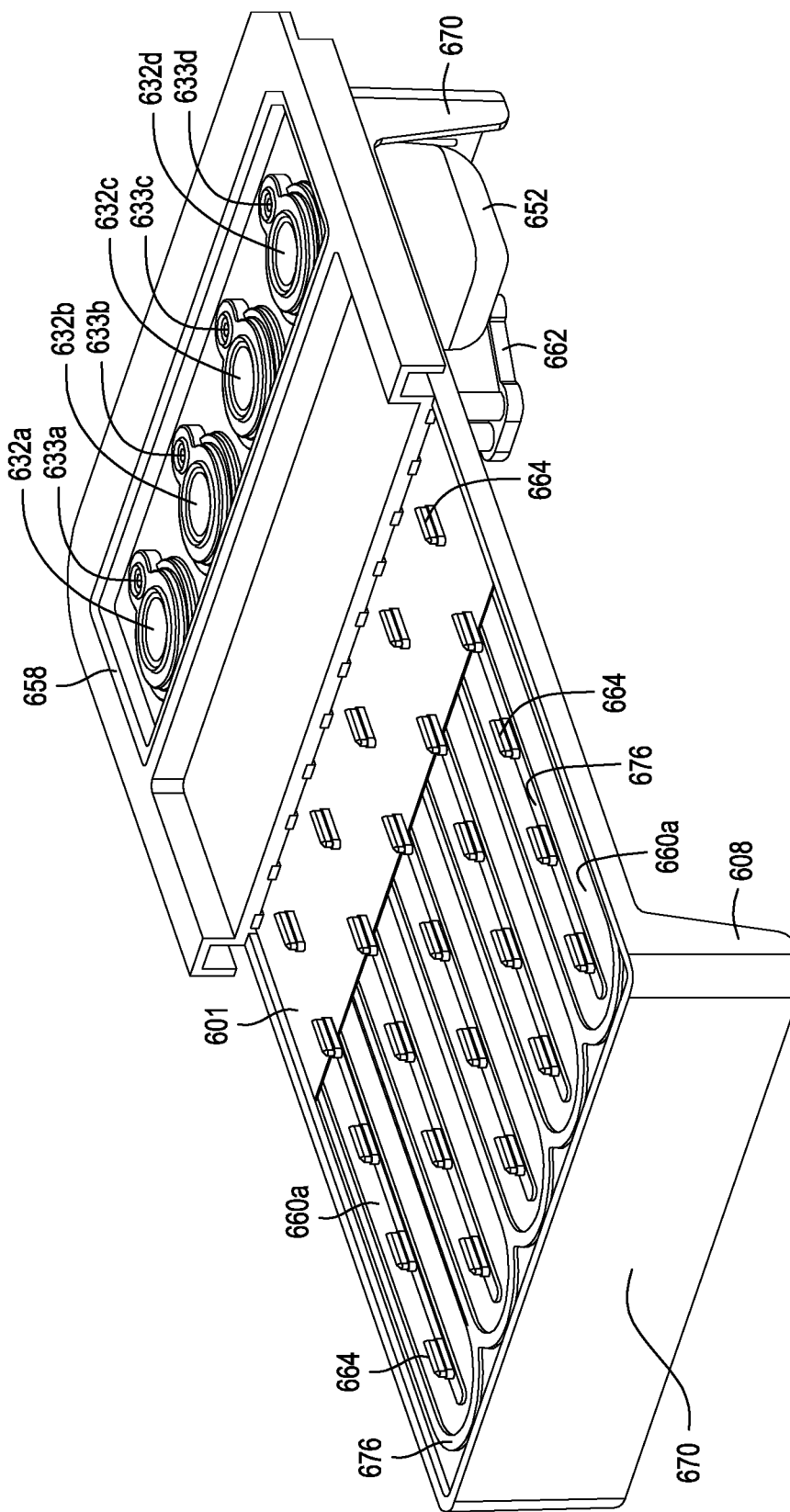

FIG. 6C is a top perspective view of a SWIIN module with the retentate and perforated members in partial cross section. In this FIG. 6C, it can be seen that serpentine channel 660a is disposed on the top of permeate member 608 is defined by raised portions 676 and traverses permeate member 608 for most of the length and width of permeate member 608 except for the portion of permeate member 608 that comprises the permeate and retentate reservoirs (note only one retentate reservoir 652 can be seen). Moving from left to right, reservoir gasket 658 is disposed upon the integrated reservoir cover 678 (cover not seen in this FIG. 6C) of retentate member 604. Gasket 658 comprises reservoir access apertures 632a, 632b, 632c, and 632d, as well as pneumatic ports 633a, 633b, 633c and 633d. Also at the far left end is support 670. Disposed under permeate reservoir 652 can be seen one of two reservoir seals 662. In addition to the retentate member being in cross section, the perforated member 601 and filter (the filter is not seen in this FIG. 6C) are in cross section. Note that there are a number of ultrasonic tabs 664 disposed at the right end of SWIIN module 650 and on raised portion 676 which defines the channel turns of serpentine channel 660a, including ultrasonic tabs 664 extending through through-holes 666 of perforated member 601 (through-holes 666 are not seen in FIG. 6C but see FIG. 6B). There is also a support 670 at the end distal reservoirs 652, 654 of permeate member 608.

Figure 6D:
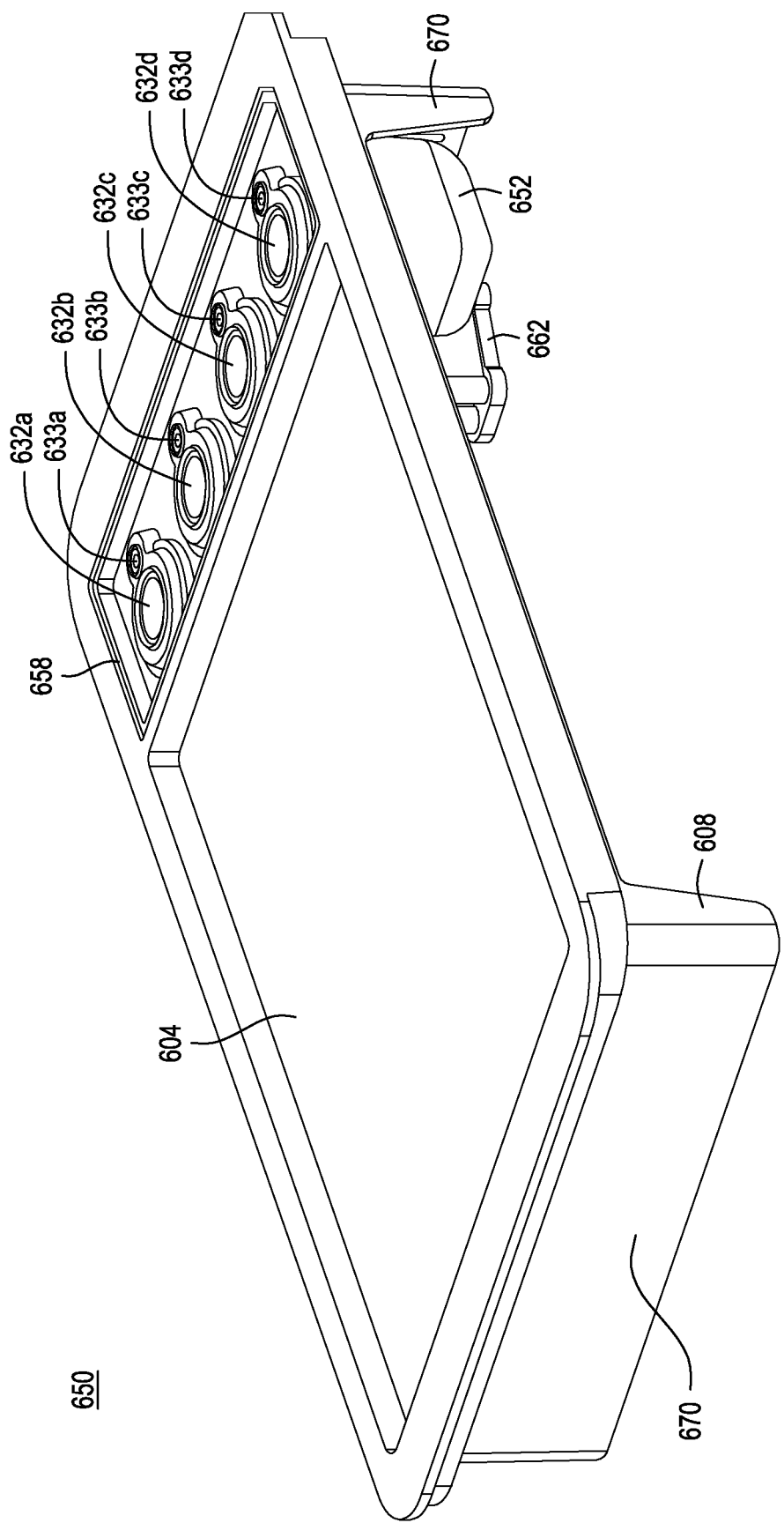

FIG. 6D is a side perspective view of an assembled SWIIIN module 650, including, from right to left, reservoir gasket 658 disposed upon integrated reservoir cover 678 (not seen) of retentate member 604. Gasket 658 may be fabricated from rubber, silicone, nitrile rubber, polytetrafluoroethylene, a plastic polymer such as polychlorotrifluoroethylene, or other flexible, compressible material. Gasket 658 comprises reservoir access apertures 632a, 632b, 632c, and 632d, as well as pneumatic ports 633a, 633b, 633c and 633d. Also at the far-left end is support 670 of permeate member 608. In addition, permeate reservoir 652 can be seen, as well as one reservoir seal 662. At the far-right end is a second support 670.

Imaging of cell colonies growing in the wells of the SWIIN is desired in most implementations for, e.g., monitoring both cell growth and device performance and imaging is necessary for cherry-picking implementations. Real-time monitoring of cell growth in the SWIIN requires backlighting, retentate plate (top plate) condensation management and a system-level approach to temperature control, air flow, and thermal management. In some implementations, imaging employs a camera or CCD device with sufficient resolution to be able to image individual wells. For example, in some configurations a camera with a 9-pixel pitch is used (that is, there are 9 pixels center-to-center for each well). Processing the images may, in some implementations, utilize reading the images in grayscale, rating each pixel from low to high, where wells with no cells will be brightest (due to full or nearly-full light transmission from the backlight) and wells with cells will be dim (due to cells blocking light transmission from the backlight). After processing the images, thresholding is performed to determine which pixels will be called "bright" or "dim", spot finding is performed to find bright pixels and arrange them into blocks, and then the spots are arranged on a hexagonal grid of pixels that correspond to the spots. Once arranged, the measure of intensity of each well is extracted, by, e.g., looking at one or more pixels in the middle of the spot, looking at several to many pixels at random or pre-set positions, or averaging X number of pixels in the spot. In addition, background intensity may be subtracted. Thresholding is again used to call each well positive (e.g., containing cells) or negative (e.g., no cells in the well). The imaging information may be used in several ways, including taking images at time points for monitoring cell growth. Monitoring cell growth can be used to, e.g., remove the "muffin tops" of fast-growing cells followed by removal of all cells or removal of cells in "rounds" as described above, or recover cells from specific wells (e.g., slow-growing cell colonies); alternatively, wells containing fast-growing cells can be identified and areas of UV light covering the fast-growing cell colonies can be projected (or rastered with shutters) onto the SWIIN to irradiate or inhibit growth of those cells. Imaging may also be used to assure proper fluid flow in the serpentine channel 660.

Figure 6E:
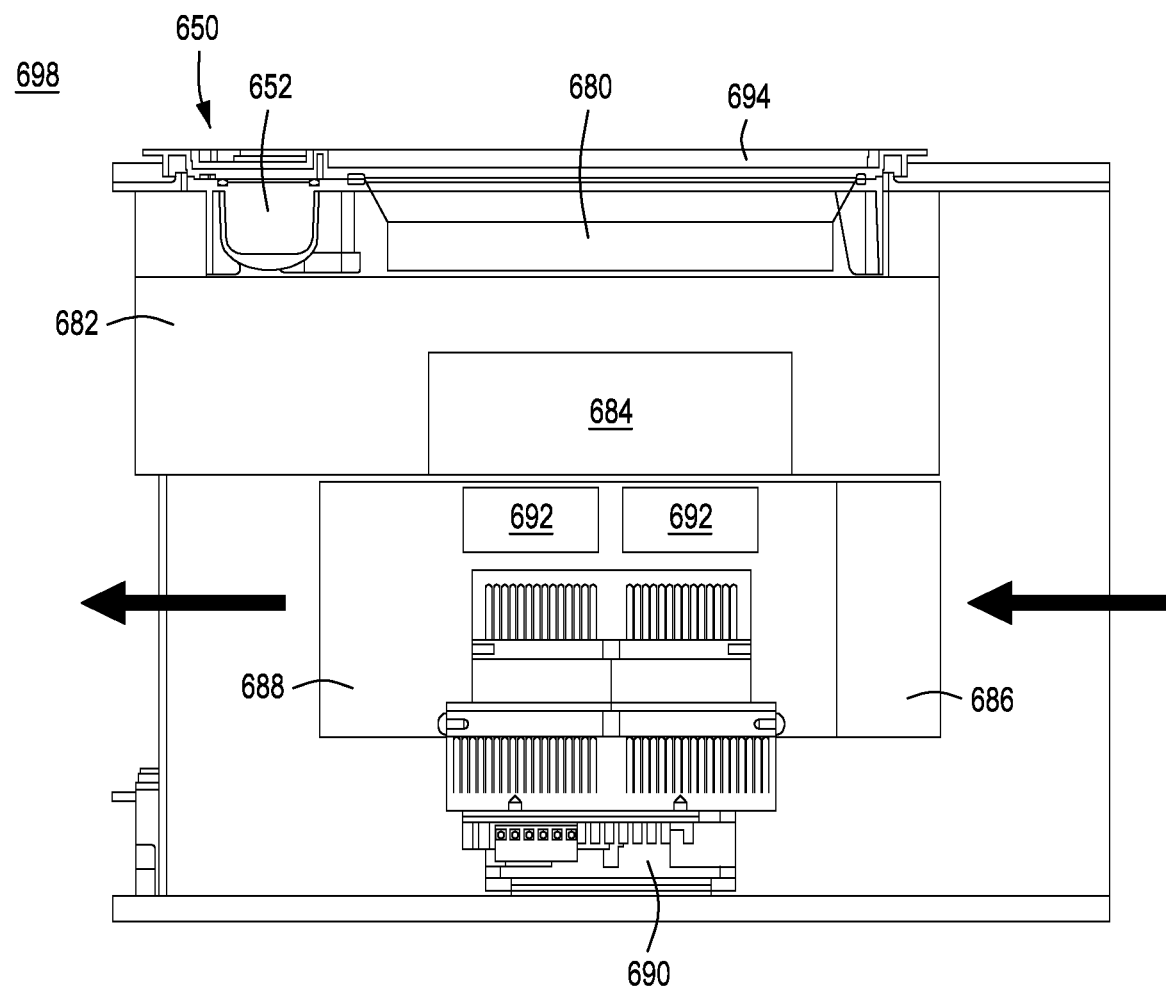
FIG. 6E depicts the embodiment of the SWIIN module in FIGS. 6B-6D further comprising a heater and a heated cover.

FIG. 6E depicts the embodiment of the SWIIN module in FIGS. 6B-6D further comprising a heat management system including a heater and a heated cover. The heater cover facilitates the condensation management that is required for imaging. Assembly 698 comprises a SWIIN module 650 seen lengthwise in cross section, where one permeate reservoir 652 is seen. Disposed immediately upon SWIIN module 650 is cover 694 and disposed immediately below SWIIN module 650 is backlight 680, which allows for imaging. Beneath and adjacent to the backlight and SWIIN module is insulation 682, which is disposed over a heatsink 684. In this FIG. 6E, the fins of the heatsink would be in-out of the page. In addition there is also axial fan 686 and heat sink 688, as well as two thermoelectric coolers 692, and a controller 690 to control the pneumatics, thermoelectric coolers, fan, solenoid valves, etc. The arrows denote cool air coming into the unit and hot air being removed from the unit. It should be noted that control of heating allows for growth of many different types of cells (prokaryotic and eukaryotic) as well as strains of cells that are, e.g., temperature sensitive, etc., and allows use of temperature-sensitive promoters. Temperature control allows for protocols to be adjusted to account for differences in transformation efficiency, cell growth and viability. For more details regarding solid wall isolation incubation and normalization devices see U.S. Ser. No. 16/399,988, filed 30 Apr. 2019; Ser. No. 16/454,865, filed 26 Jun. 2019; and Ser. No. 16/540,606, filed 14 Aug. 2019. For alternative isolation, incubation and normalization modules, see U.S. Ser. No. 16/536,049, filed 8 Aug. 2019.

Use of the Automated Multi-Module Cell Processing Instrument

Figure 7:
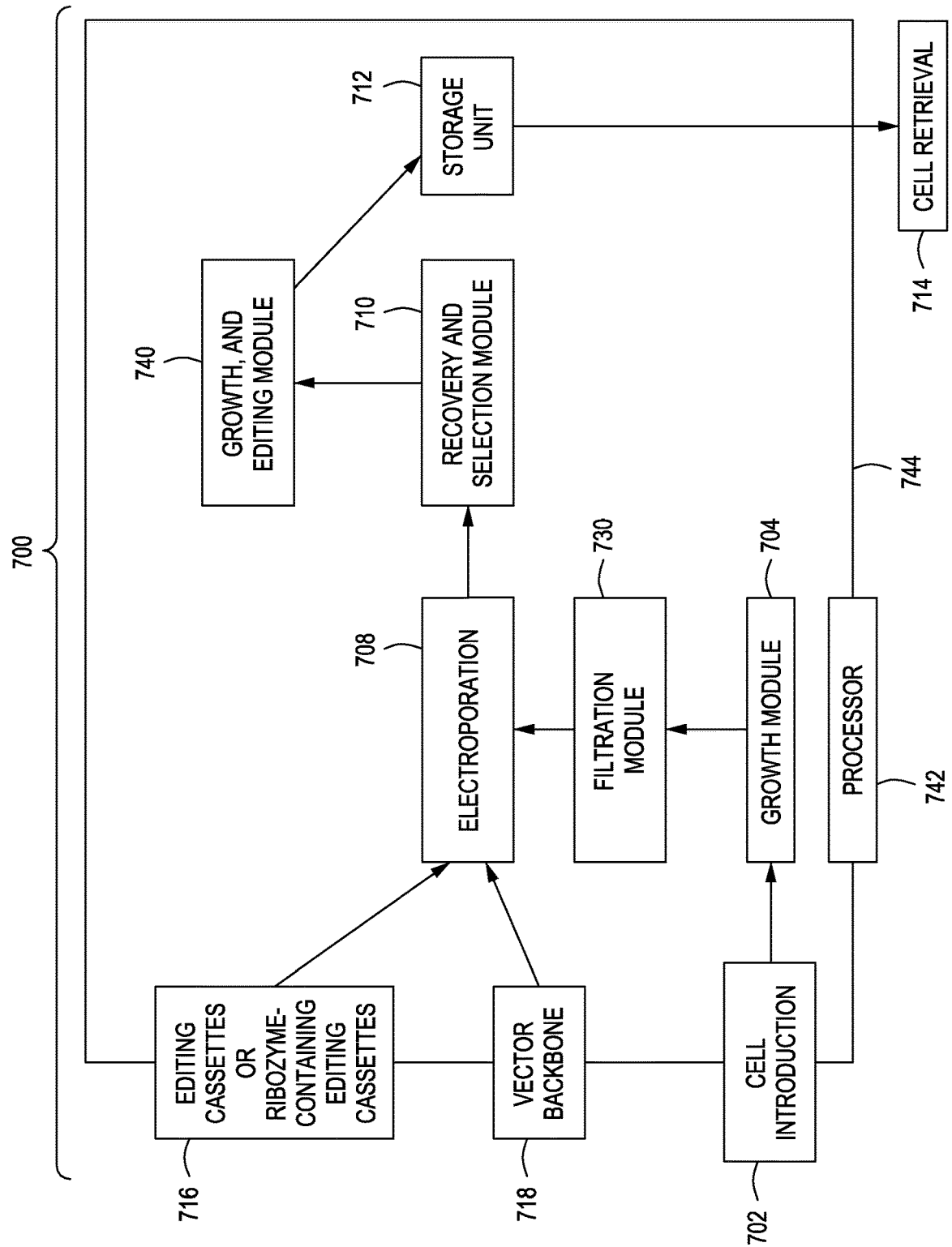
FIG. 7 is a simplified process diagram of an embodiment of an exemplary automated multi-module cell processing instrument.

FIG. 7 is a simplified block diagram of an embodiment of an exemplary automated multi-module cell processing instrument comprising a bulk liquid growth module for induced editing and enrichment for edited cells. The cell processing instrument 700 may include a housing 744, a reservoir of cells to be transformed or transfected 702, and a growth module (a cell growth device) 704. The cells to be transformed are transferred from a reservoir to the growth module to be cultured until the cells hit a target OD. Once the cells hit the target OD, the growth module may cool or freeze the cells for later processing, or the cells may be transferred to a filtration/concentration module 730 where the cells are rendered electrocompetent and concentrated to a volume optimal for cell transformation. Once concentrated, the cells are then transferred to an electroporation device 708 (e.g., transformation/transfection module).

In addition to the reservoir for storing the cells, the system 700 may include a reservoir for storing editing cassettes or ribozyme-containing editing cassettes 716 and a vector backbone 718. Both the editing cassettes or ribozyme-containing editing cassettes and the vector backbone are transferred from the reagent cartridge to, e.g., an electroporation device 708, which already contains the cell culture grown to a target OD and rendered electrocompetent via filtration module 730. In electroporation device 708, the assembled nucleic acids are introduced into the cells. Following electroporation, the cells are transferred into a combined recovery/selection module 710. For examples of multi-module cell editing instruments, see U.S. Pat. No. 10,253,316, issued 9 Apr. 2019; U.S. Pat. No. 10,329,559, issued 25 Jun. 2019; U.S. Pat. No. 10,323,242, issued 18 Jun. 2019; U.S. Pat. No. 10,421,959, issued 24 Sep. 2019; U.S. Pat. No. 10,465,185, issued 5 Nov. 2019; U.S. Pat. No. 10,519,437, issued 31 Dec. 2019; and U.S. Ser. No. 16/680,643, filed 12 Nov. 2019; Ser. No. 16/666,964, filed 29 Oct. 2019; Ser. No. 16/750,369, filed 23 Jan. 2020, all of which are herein incorporated by reference in their entirety.

Following recovery, and, optionally, selection 710, the cells are transferred to a growth, and editing module 740. The cells are allowed to grow and editing take place. In some embodiments, editing is induced by transcription of one or both of the nuclease and the gRNA being under the control of an inducible promoter. In some embodiments, the inducible promoter is a pL promoter where the promoter is activated by a rise in temperature and "deactivated" by lowering the temperature.

The recovery, selection, growth, editing and storage modules may all be separate, may be arranged and combined as shown in FIG. 2A, or may be arranged or combined in other configurations. In certain embodiments, recovery and selection are performed in one module, and growth and editing are performed in a separate module. Alternatively, recovery, selection, growth, editing, and re-growth are performed in a single module.

Once the cells are edited and re-grown (e.g., recovered from editing), the cells may be stored, e.g., in a storage module 712, where the cells can be kept at, e.g., 4° C. until the cells are retrieved 714 for further study. Alternatively, the cells may be used in another round of editing. The multi-module cell processing instrument is controlled by a processor 742 configured to operate the instrument based on user input, as directed by one or more scripts, or as a combination of user input or a script. The processor 742 may control the timing, duration, temperature, and operations of the various modules of the system 700 and the dispensing of reagents. For example, the processor 742 may cool the cells post-transformation until editing is desired, upon which time the temperature may be raised to a temperature conducive of genome editing and cell growth. The processor may be programmed with standard protocol parameters from which a user may select, a user may specify one or more parameters manually or one or more scripts associated with the reagent cartridge may specify one or more operations and/or reaction parameters. In addition, the processor may notify the user (e.g., via an application to a smart phone or other device) that the cells have reached the target OD as well as update the user as to the progress of the cells in the various modules in the multi-module system.

The automated multi-module cell processing instrument 700 is a nuclease-directed genome editing system and can be used in single editing systems where, e.g., two or more edits to a cellular genome are introduced using a single editing process via multiplex editing cassettes. The system may be configured to perform sequential editing, e.g., using different nuclease-directed systems sequentially to provide two or more genome edits in a cell in each of two or more rounds of editing; and/or recursive editing, e.g. utilizing a single nuclease-directed system to introduce sequentially two or more genome edits in a cell in each of two or more round of editing.

Figure 8:
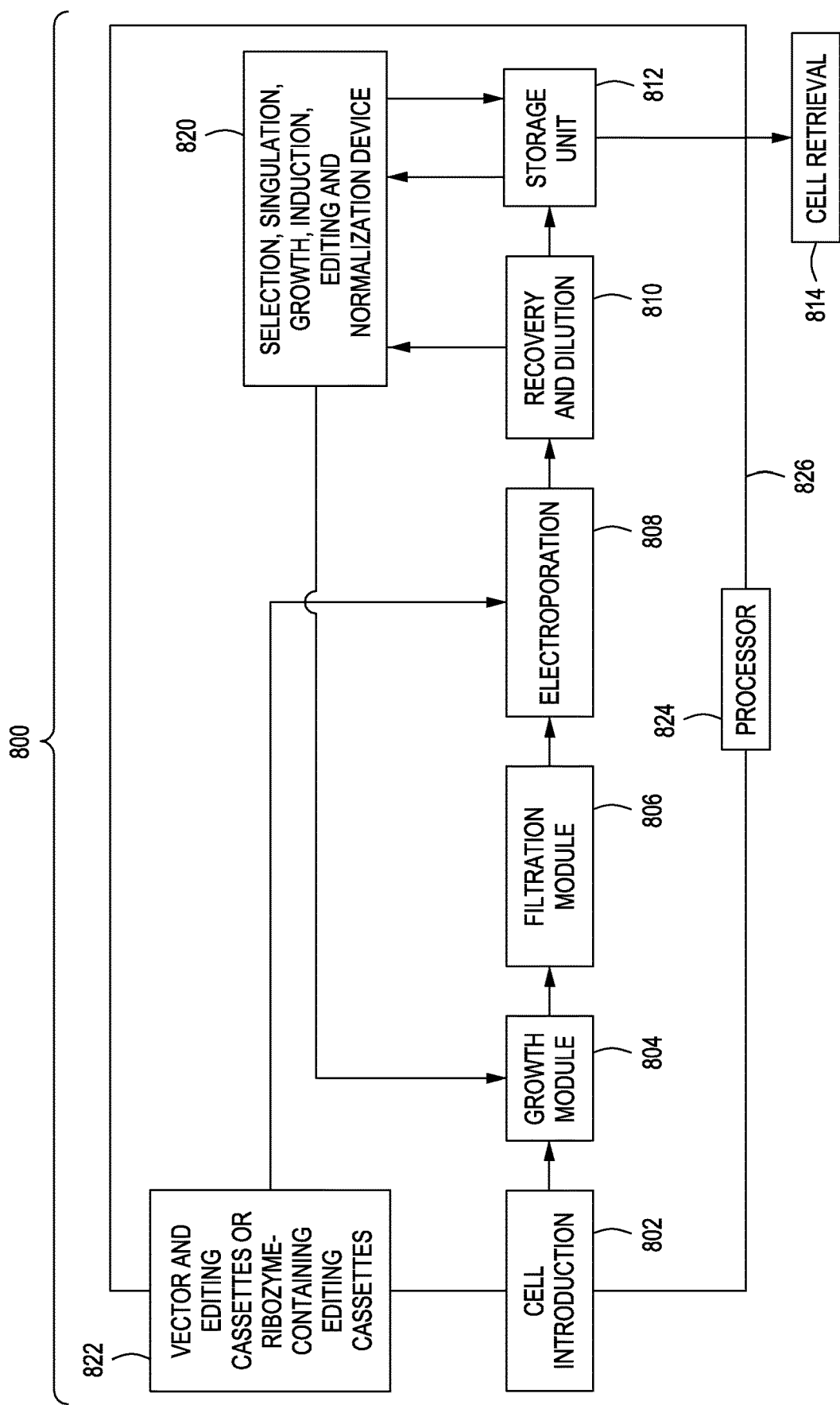
FIG. 8 is a simplified process diagram of an embodiment of an exemplary automated multi-module cell processing instrument comprising a solid wall singulation/growth/editing/normalization module for recursive yeast cell editing.

FIG. 8 illustrates another embodiment of a multi-module cell processing instrument. This embodiment depicts an exemplary system that performs recursive gene editing on a yeast cell population. The cell processing instrument 800 may include a housing 826, a reservoir for storing cells to be transformed or transfected 802, and a cell growth module (comprising, e.g., a rotating growth vial) 804. The cells to be transformed are transferred from a reservoir to the cell growth module to be cultured until the cells hit a target OD. Once the cells hit the target OD, the growth module may cool or freeze the cells for later processing or transfer the cells to a cell concentration module 806 where the cells are subjected to buffer exchange and rendered electrocompetent, and the volume of the cells may be reduced substantially. Once the cells have been concentrated to an appropriate volume, the cells are transferred to electroporation device 808. In addition to the reservoir for storing cells 812, the multi-module cell processing instrument includes a reservoir for storing the vector backbone and editing cassettes or ribozyme-containing editing cassettes 822. The vector backbones and editing cassettes or ribozyme-containing editing cassettes are transferred to the electroporation device 808, which already contains the cell culture grown to a target OD. In the electroporation device 808, the nucleic acids are electroporated into the cells. Following electroporation, the cells are transferred into an optional recovery and dilution module 810, where the cells recover briefly post-transformation.

After recovery, the cells may be transferred to a storage module 812, where the cells can be stored at, e.g., 4° C. for later processing or retrieved 814, or the cells may be diluted and transferred to a selection/singulation/growth/induction/editing/normalization (SWIIN) module 820. In the SWIIN 820, the cells are arrayed such that there is an average of one cell per microwell. The arrayed cells may be in selection medium to select for cells that have been transformed or transfected with the editing vector(s). Once singulated, the cells grow through 2-50 doublings and establish colonies. Once colonies are established, editing is induced by providing conditions (e.g., temperature, addition of an inducing or repressing chemical) to induce editing. Editing is then initiated and allowed to proceed, the cells are allowed to grow to terminal size (e.g., normalization of the colonies) in the microwells and then are treated to conditions that cure the editing vector from this round. Once cured, the cells can be flushed out of the microwells and pooled, then transferred to the storage (or recovery) unit 812 or can be transferred back to the growth module 804 for another round of editing. In between pooling and transfer to a growth module, there typically is one or more additional steps, such as cell recovery, medium exchange (rendering the cells electrocompetent), cell concentration (typically concurrently with medium exchange by, e.g., filtration. Note that the selection/ singulation/growth/induction/editing/normalization and curing modules may be the same module, where all processes are performed in, e.g., a solid wall device, or selection and/or dilution may take place in a separate vessel before the cells are transferred to the solid wall singulation/growth/induction/editing/normalization/editing module (SWIIN). Similarly, the cells may be pooled after normalization, transferred to a separate vessel, and cured in the separate vessel. As an alternative to singulation in, e.g., a solid wall device, the transformed cells may be grown in—and editing can be induced in—bulk liquid. Once the putatively-edited cells are pooled, they may be subjected to another round of editing, beginning with growth, cell concentration and treatment to render electrocompetent, and transformation by yet another donor nucleic acid in another editing cassette via the electroporation module 808.

In electroporation device 808, the yeast cells selected from the first round of editing are transformed by a second set of editing cassettes or ribozyme-containing editing cassettes and vector backbones and the cycle is repeated until the cells have been transformed and edited by a desired number of, e.g., editing cassettes. The multi-module cell processing instrument exemplified in FIG. 8 is controlled by a processor 824 configured to operate the instrument based on user input or is controlled by one or more scripts including at least one script associated with the reagent cartridge. The processor 824 may control the timing, duration, and temperature of various processes, the dispensing of reagents, and other operations of the various modules of the instrument 800. For example, a script or the processor may control the dispensing of cells, reagents, vectors, and editing oligonucleotides; which editing oligonucleotides are used for cell editing and in what order; the time, temperature and other conditions used in the recovery and expression module, the wavelength at which OD is read in the cell growth module, the target OD to which the cells are grown, and the target time at which the cells will reach the target OD. In addition, the processor may be programmed to notify a user (e.g., via an application) as to the progress of the cells in the automated multi-module cell processing instrument.

It should be apparent to one of ordinary skill in the art given the present disclosure that the process described may be recursive and multiplexed; that is, cells may go through the workflow described in relation to FIG. 7 or 8, then the resulting edited culture may go through another (or several or many) rounds of additional editing (e.g., recursive editing) with different editing cassettes (or ribozyme-containing editing cassettes). For example, the cells from round 1 of editing may be diluted and an aliquot of the edited cells edited by editing cassette A may be combined with editing cassette B, an aliquot of the edited cells edited by editing cassette A may be combined with editing cassette C, an aliquot of the edited cells edited by editing cassette A may be combined with editing cassette D, and so on for a second round of editing. After round two, an aliquot of each of the double-edited cells may be subjected to a third round of editing, where, e.g., aliquots of each of the AB-, AC-, AD-edited cells are combined with additional editing cassettes, such as editing cassettes X, Y, and Z. That is that double-edited cells AB may be combined with and edited by editing cassettes X, Y, and Z to produce triple-edited edited cells ABX, ABY, and ABZ; double-edited cells AC may be combined with and edited by editing cassettes X, Y, and Z to produce triple-edited cells ACX, ACY, and ACZ; and double-edited cells AD may be combined with and edited by editing cassettes X, Y, and Z to produce triple-edited cells ADX, ADY, and ADZ, and so on. In this process, many permutations and combinations of edits can be executed, leading to very diverse cell populations and cell libraries. That is, the methods and compositions disclosed herein allow for multi-vector transformation with 1) a library of backbones having the same selective marker or a library of backbones having more than one selective marker; and 2) a library of editing cassettes or ribozyme-containing editing cassette having a single gRNA/donor DNA pair or a library of editing cassettes or ribozyme-containing editing cassettes having two or more gRNA/donor DNA pairs. These multi-vector transformations can then be performed sequentially any number of times to introduce many edits into each cell.

In any recursive process, it is advantageous to "cure" the editing vectors (e.g., the gap-repaired vector backbone+the editing cassette or ribozyme-containing editing cassette). "Curing" is a process in which one or more editing vectors used in the prior round of editing is eliminated from the transformed cells. Curing can be accomplished by, e.g., cleaving the editing vector(s) using a curing plasmid thereby rendering the editing vectors nonfunctional; diluting the editing vector(s) in the cell population via cell growth (that is, the more growth cycles the cells go through, the fewer daughter cells will retain the editing vector(s)), or by, e.g., utilizing a heat-sensitive origin of replication on the editing vector. The conditions for curing will depend on the mechanism used for curing; that is, in this example, how the curing plasmid cleaves the editing vector.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Example 1: Editing Cassette and Backbone Amplification and Assembly

Editing Cassette Preparation: 5 nM of oligonucleotides synthesized on a chip were amplified using Q5 polymerase in 50 µL volumes. The PCR conditions were 95° C. for 1 minute; 8 rounds of 95° C. for 30 seconds/60° C. for 30 seconds/72° C. for 2.5 minutes; with a final hold at 72° C. for 5 minutes. Following amplification, the PCR products were subjected to SPRI cleanup, where 30 µL SPRI mix was added to the 50 µL PCR reactions and incubated for 2 minutes. The tubes were subjected to a magnetic field for 2 minutes, the liquid was removed, and the beads were washed 2× with 80% ethanol, allowing 1 minute between washes. After the final wash, the beads were allowed to dry for 2 minutes, 50 µL 0.5×TE pH 8.0 was added to the tubes, and the beads were vortexed to mix. The slurry was incubated at room temperature for 2 minutes, then subjected to the magnetic field for 2 minutes. The eluate was removed and the DNA quantified.

Following quantification, a second amplification procedure was carried out using a dilution of the eluate from the SPRI cleanup. PCR was performed under the following conditions: 95° C. for 1 minute; 18 rounds of 95° C. for 30 seconds/72° C. for 2.5 minutes; with a final hold at 72° C. for 5 minutes. Amplicons were checked on a 2% agarose gel and pools with the cleanest output(s) were identified. Amplification products appearing to have heterodimers or chimeras were not used.

Backbone Preparation: A 10-fold serial dilution series of purified backbone was performed, and each of the diluted backbone series was amplified under the following conditions: 95° C. for 1 minute; then 30 rounds of 95° C. for 30 seconds/60° C. for 1.5 minutes/72° C. for 2.5 minutes; with a final hold at 72° C. for 5 minutes. After amplification, the amplified backbone was subjected to SPRI cleanup as described above in relation to the cassettes. The backbone was eluted into 100 µL ddH$_2$O and quantified before isothermal assembly.

Gibson Assembly: 150 ng backbone DNA was combined with 100 ng cassette DNA. An equal volume of 2× Gibson Master Mix was added, and the reaction was incubated for 45 minutes at 50° C. After assembly, the assembled backbone and cassettes were subjected to SPRI cleanup, as described above.

Example 2: Growth in the Cell Growth Module

Figure 9:
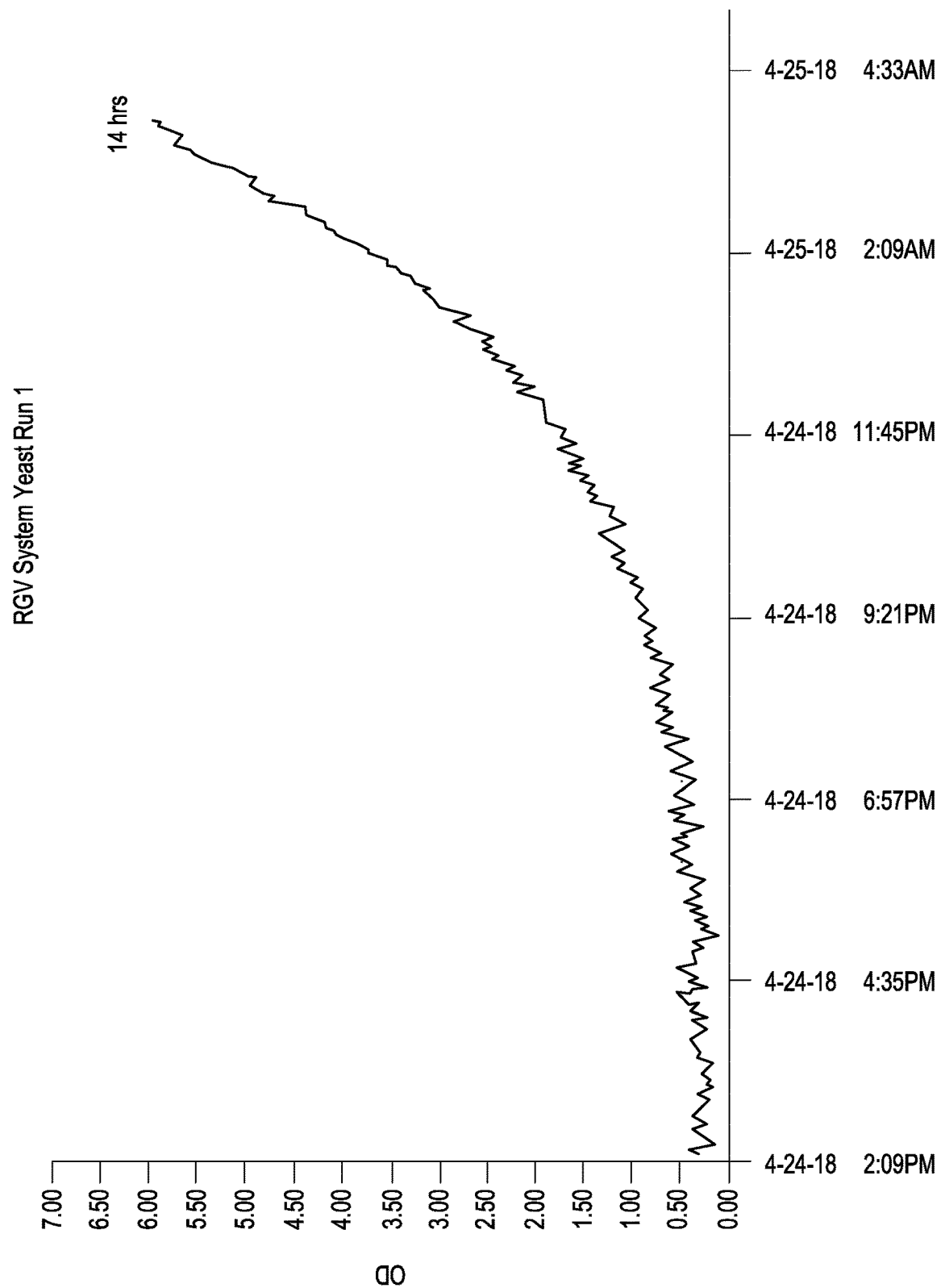
FIG. 9 is a graph demonstrating real-time monitoring of growth of *S. cerevisiae* yeast cell culture $OD_{600}$ employing the cell growth device as described in relation to FIGS. 3A-3D where a 2-paddle rotating growth vial was used.

One embodiment of the cell growth device as described herein was used to grow a yeast cell culture which was monitored in real time using an embodiment of the cell growth device described herein. The rotating growth vial/cell growth device was used to measure OD$_{600}$ in real time of yeast s288c cells in YPAD medium. The cells were grown at 30° C. using oscillating rotation and employing a 2-paddle rotating growth vial. FIG. 9 is a graph showing the results. Note that OD$_{600}$ 6.0 was reached in 14 hours.

Example 3: Cell Concentration

Figure 10:
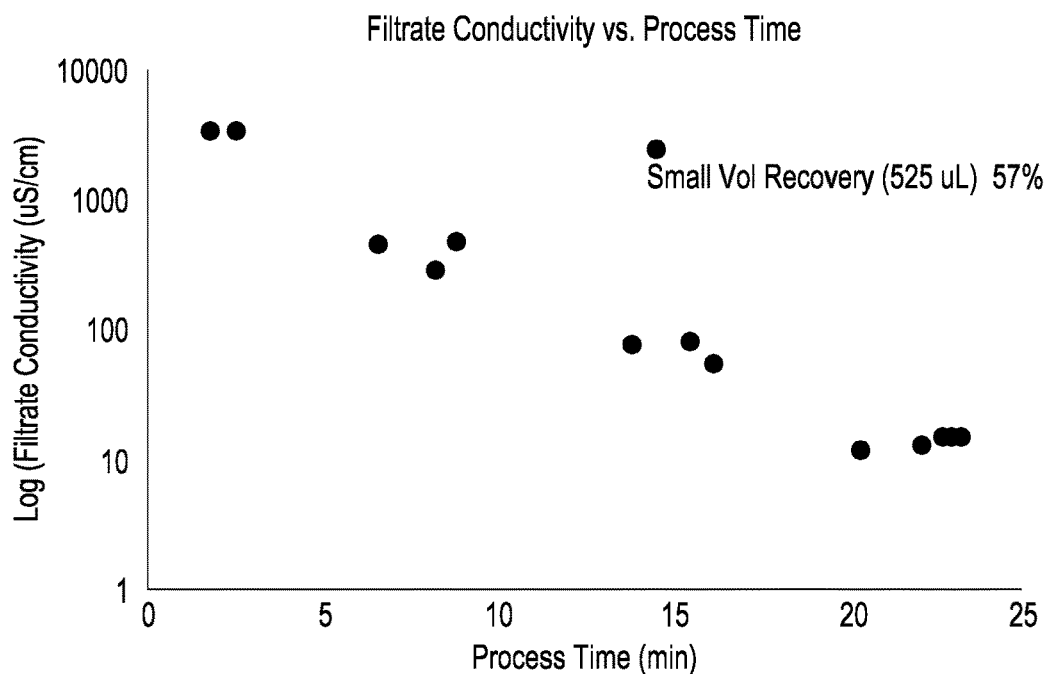
FIG. 10 is a graph plotting filtrate conductivity against filter processing time for a yeast culture processed in the cell concentration device/module described in relation to FIGS. 4A-4E.

The TFF module as described above in relation to FIGS. 4A-4E has been used successfully to process and perform buffer exchange on yeast cultures. A yeast culture was initially concentrated to approximately 5 ml using two passes through the TFF device in opposite directions. The cells were washed with 50 ml of 1M sorbitol three times, with three passes through the TFF device after each wash. After the third pass of the cells following the last wash with 1M sorbitol, the cells were passed through the TFF device two times, wherein the yeast cell culture was concentrated to approximately 525 µl. FIG. 10 presents the filter buffer exchange performance for yeast cells determined by measuring filtrate conductivity and filter processing time. Target conductivity (~10 µS/cm) was achieved in approximately 23 minutes utilizing three 50 ml 1M sorbitol washes and three passes through the TFF device for each wash. The volume of the cells was reduced from 20 ml to 525 µl. Recovery of approximately 90% of the cells has been achieved.

Example 4: Production and Transformation of Electrocompetent S. Cerevisiae

For testing transformation of the FTEP device in yeast, S. Cerevisiae cells were created using the methods as generally set forth in Bergkessel and Guthrie, Methods Enzymol., 529:311-20 (2013). Briefly, YPAD media was inoculated for overnight growth, with 3 ml inoculate to produce 100 ml of cells. Every 100 ml of culture processed resulted in approximately 1 ml of competent cells. Cells were incubated at 30° C. in a shaking incubator until they reached an OD600 of 1.5+/−0.1.

A conditioning buffer was prepared using 100 mM lithium acetate, 10 mM dithiothreitol, and 50 mL of buffer for every 100 mL of cells grown and kept at room temperature. Cells were harvested in 250 ml bottles at 4300 rpm for 3 minutes, and the supernatant removed. The cell pellets were suspended in 100 ml of cold 1 M sorbitol, spun at 4300 rpm for 3 minutes and the supernatant once again removed. The cells were suspended in conditioning buffer, then the suspension transferred into an appropriate flask and shaken at 200 RPM and 30° C. for 30 minutes. The suspensions were transferred to 50 ml conical vials and spun at 4300 rpm for 3 minutes. The supernatant was removed and the pellet resuspended in cold 1 M sorbitol. These steps were repeated three times for a total of three wash-spin-decant steps. The pellet was suspended in sorbitol to a final OD of 150+/−20.

A comparative electroporation experiment was performed to determine the efficiency of transformation of the electrocompetent S. cerevisiae using the FTEP device. The flow rate was controlled with a syringe pump (Harvard apparatus PHD ULTRA™ 4400). The suspension of cells with DNA was loaded into a 1 mL glass syringe (Hamilton 81320 Syringe, PTFE Luer Lock) before mounting on the pump. The output from the function generator was turned on immediately after starting the flow. The processed cells flowed directly into a tube with 1M sorbitol with carbenicillin. Cells were collected until the same volume electroporated in the NEPAGENE™ had been processed, at which point the flow and the output from the function generator were stopped. After a 3-hour recovery in an incubator shaker at 30° C. and 250 rpm, cells were plated to determine the colony forming units (CFUs) that survived electroporation and failed to take up a plasmid and the CFUs that survived electroporation and took up a plasmid. Plates were incubated at 30° C. Yeast colonies are counted after 48-76 hrs.

Figure 11:
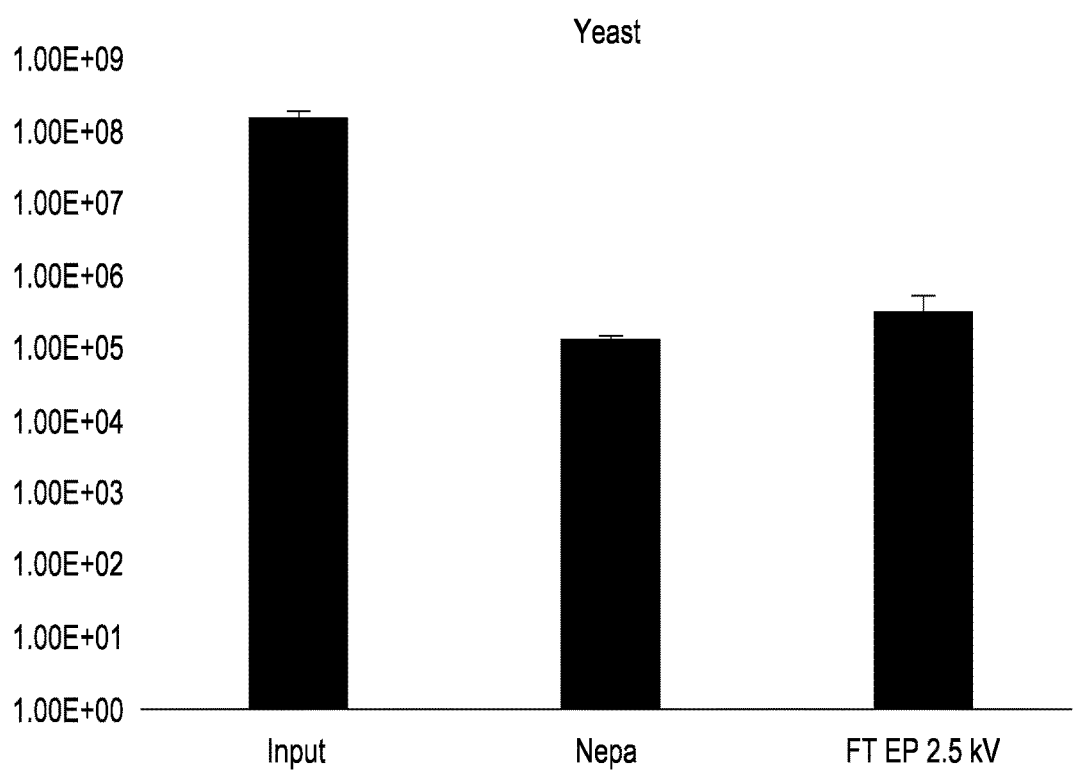
FIG. 11 is a bar graph showing the results of electroporation of *S. cerevisiae* using an FTEP device as described in relation to FIGS. 5A-5F and a comparator electroporation method.

The flow-through electroporation experiments were benchmarked against 2 mm electroporation cuvettes (Bull dog Bio) using an in vitro high voltage electroporator (NEPAGENE™ ELEPO21). Stock tubes of cell suspensions with DNA were prepared and used for side-to-side experiments with the NEPAGENE™ and the flow-through electroporation. The results are shown in FIG. 11. The device showed better transformation and survival of electrocompetent S. Cerevisiae at 2.5 kV voltages as compared to the NEPAGENE™ method. Input is total number of cells that were processed.

Example 5: Sinjulation of Yeast Colonies in a Solid Wall Device

Electrocompetent yeast cells were transformed with a cloned library, an isothermal assembled library, or a process control sgRNA plasmid (escapee surrogate). Electrocompetent Saccharomyces cerevisiae cells were prepared as follows: The afternoon before transformation was to occur, 10 mL of YPAD was inoculated with the selected Saccharomyces cerevisiae strain. The culture was shaken at 250 RPM and 30° C. overnight. The next day, 100 mL of YPAD was added to a 250-mL baffled flask and inoculated with the overnight culture (around 2 mL of overnight culture) until the OD600 reading reached 0.3+/−0.05. The culture was placed in the 30° C. incubator shaking at 250 RPM and allowed to grow for 4-5 hours, with the OD checked every hour. When the culture reached an OD600 of approximately 1.5, 50 mL volumes were poured into two 50-mL conical vials, then centrifuged at 4300 RPM for 2 minutes at room temperature. The supernatant was removed from all 50 ml conical tubes, while avoiding disturbing the cell pellet. 50 mL of a Lithium Acetate/Dithiothreitol solution was added to each conical tube and the pellet was gently resuspended. Both suspensions were transferred to a 250 mL flask and placed in the shaker; then shaken at 30° C. and 200 RPM for 30 minutes.

After incubation was complete, the suspension was transferred to two 50-mL conical vials. The suspensions then were centrifuge at 4300 RPM for 3 minutes, then the supernatant was discarded. Following the lithium acetate/Dithiothreitol treatment step, cold liquids were used and the cells were kept on ice until electroporation. 50 mL of 1 M sorbitol was added and the pellet was resuspended, then centrifuged at 4300 RPM, 3 minutes, 4° C., after which the supernatant was discarded. The 1M sorbitol wash was repeated twice for a total of three washes. 50 uL of 1 M sorbitol was added to one pellet, cells were resuspended, then transferred to the other tube to suspend the second pellet. The volume of the cell suspension was measured and brought to 1 mL with cold 1 M sorbitol. At this point the cells were electrocompetent and could be transformed with a cloned library, an isothermal assembled library, or process control sgRNA plasmids.

In brief, a required number of 2-mm gap electroporation cuvettes were prepared by labeling the cuvettes and then chilling on ice. The appropriate plasmid—or DNA mixture—was added to each corresponding cuvette and placed back on ice. 100 uL of electrocompetent cells was transferred to each labelled cuvette, and each sample was electroporated using appropriate electroporator conditions. 900 uL of room temperature YPAD Sorbitol media was then added to each cuvette. The cell suspension was transferred to a 14 ml culture tube and then shaken at 30° C., 250 RPM for 3 hours. After a 3 hr recovery, 9 ml of YPAD containing the appropriate antibiotic, e.g., geneticin or Hygromycin B, was added. At this point the transformed cells were processed in parallel in the solid wall device and the standard plating protocol, so as to compare "normalization" in the sold wall device with the standard benchtop process. Immediately before cells the cells were introduced to the permeable-bottom solid wall device, the 0.45 µM filter forming the bottom of the microwells was treated with a 0.1% TWEEN™ (polysorbate 20, or IUPAC polyoxyethylene (20) sorbitan monolaurate) solution to effect proper spreading/distribution of the cells into the microwells of the solid wall device. The filters were placed into a Swinnex Filter Holder (47 mm, Millipore®, SX0004700) and 3 ml of a solution with 0.85% NaCl and 0.1% TWEEN™ (polysorbate 20, or IUPAC polyoxyethylene (20) sorbitan monolaurate) was pulled through the solid wall device and filter through using a vacuum. Different TWEEN™ (polysorbate 20, or IUPAC polyoxyethylene (20) sorbitan monolaurate) concentrations were evaluated, and it was determined that for a 47 mm diameter solid wall device with a 0.45 µM filter forming the bottom of the microwells, a pre-treatment of the solid wall device+filter with 0.1% TWEEN™ (polysorbate 20, or IUPAC polyoxyethylene (20) sorbitan monolaurate) was preferred (data not shown).

After the 3-hour recovery in YPAD the transformed cells were diluted and a 3 ml volume of the diluted cells was processed through the TWEEN™ (polysorbate 20, or IUPAC polyoxyethylene (20) sorbitan monolaurate)-treated solid wall device and filter, again using a vacuum. The number of successfully transformed cells was expected to be approximately 1.0E+06 to 1.0E+08, with the goal of loading approximately 10,000 transformed cells into the current 47 mm permeable-bottom solid wall device (having ~30,000 wells). Serial dilutions of $10^{-1}$, $10^{-2}$, and $10^{-3}$ were prepared, then 100 µL volumes of each of these dilutions were combined with 3 ml 0.85% NaCl, and the samples were loaded onto solid wall devices. Each permeable-bottom solid wall device was then removed from the Swinnex filter holder and transferred to an LB agar plate containing carbenicillin (100 µg/ml), chloramphenicol (25 µg/ml) and arabinose (1% final concentration). The solid wall devices were placed metal side "up," so that the permeable-bottom membrane was touching the surface of the agar such that the nutrients from the plate could travel up through the filter "bottom" of the wells. The solid wall devices on the YPD agar plates were incubated for 2-3 days at 30° C.

At the end of the incubation the perforated disks and filters (still assembled) were removed from the supporting nutrient source (in this case an agar plate) and were photographed with a focused, "transilluminating" light source so that the number and distribution of loaded microwells on the solid wall device could be assessed (data not shown). To retrieve cells from the permeable-bottom solid wall device, the filter was transferred to a labeled sterile 100 mm petri dish which contained 15 ml of sterile 0.85% NaCl, then the petri dish was placed in a shaking incubator set to 30° C./80 RPM to gently remove the cells from the filter and resuspend the cells in the 0.85% NaCl. The cells were allowed cells to shake for 15 minutes, then were transferred to a sterile tube, e.g., a 50 ml conical centrifuge tube. The OD600 of the cell suspension was measured; at this point the cells can be processed in different ways depending on the purpose of the study. For example, if an ADE2 stop codon mutagenesis library is used, successfully-edited cells should result in colonies with a red color phenotype when the resuspended cells are spread onto YPD agar plates and allowed to grow for 4-7 days. This phenotypic difference allows for a quantification of percentage of edited cells and the extent of normalization of edited and unedited cells.

Example 6: Multiplex Editing of Yeast

Figure 12:
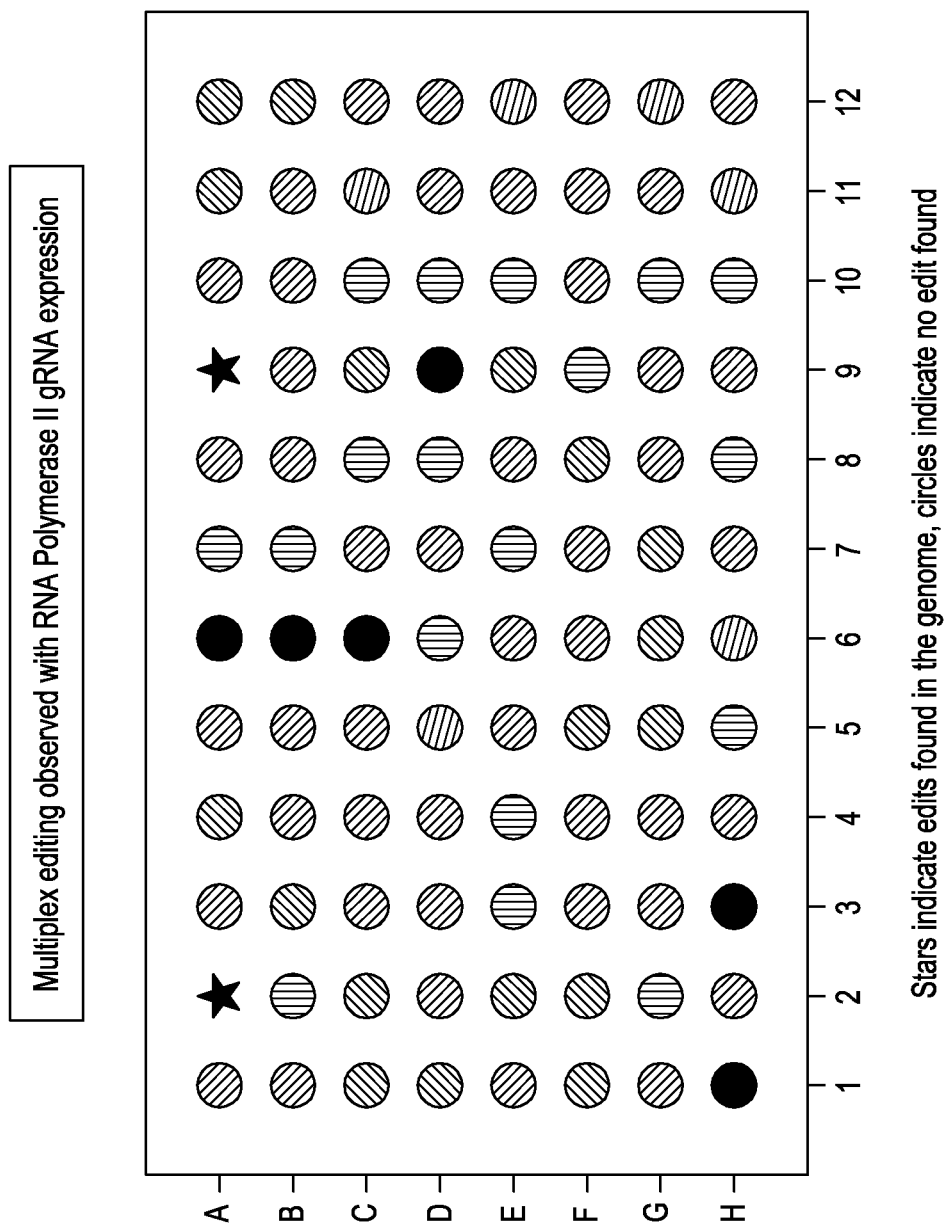
FIG. 12 shows the results of multiplex editing observed with ribozyme-containing editing cassettes.

FIG. 12 shows the results of multiplex editing of yeast using an RNA pol II gRNA expression system. A 500-member library of editing cassettes, designed to created silent swap mutations in various CDSs in the yeast genome was transformed into yeast along with a cassette backbone containing RNA pol II gRNA expression machinery, MAD7 expression machinery and a selectable drug marker, KanMX. Transformed cells were selected for via antibiotic containing agar. Individual colonies from the agar were picked into selective liquid media grown overnight. DNA from the overnight cultures was then extracted and shotgun sequenced on a NextSeq. Genomic DNA from the extractions was aligned against the intended edited sequence of the cassette contained within the individual colonies. A star on the plate indicates that the correct intended edit was found in the individual colony. A circle on the plate indicates the intended edit was not found in the genomic DNA.

Figure 13:
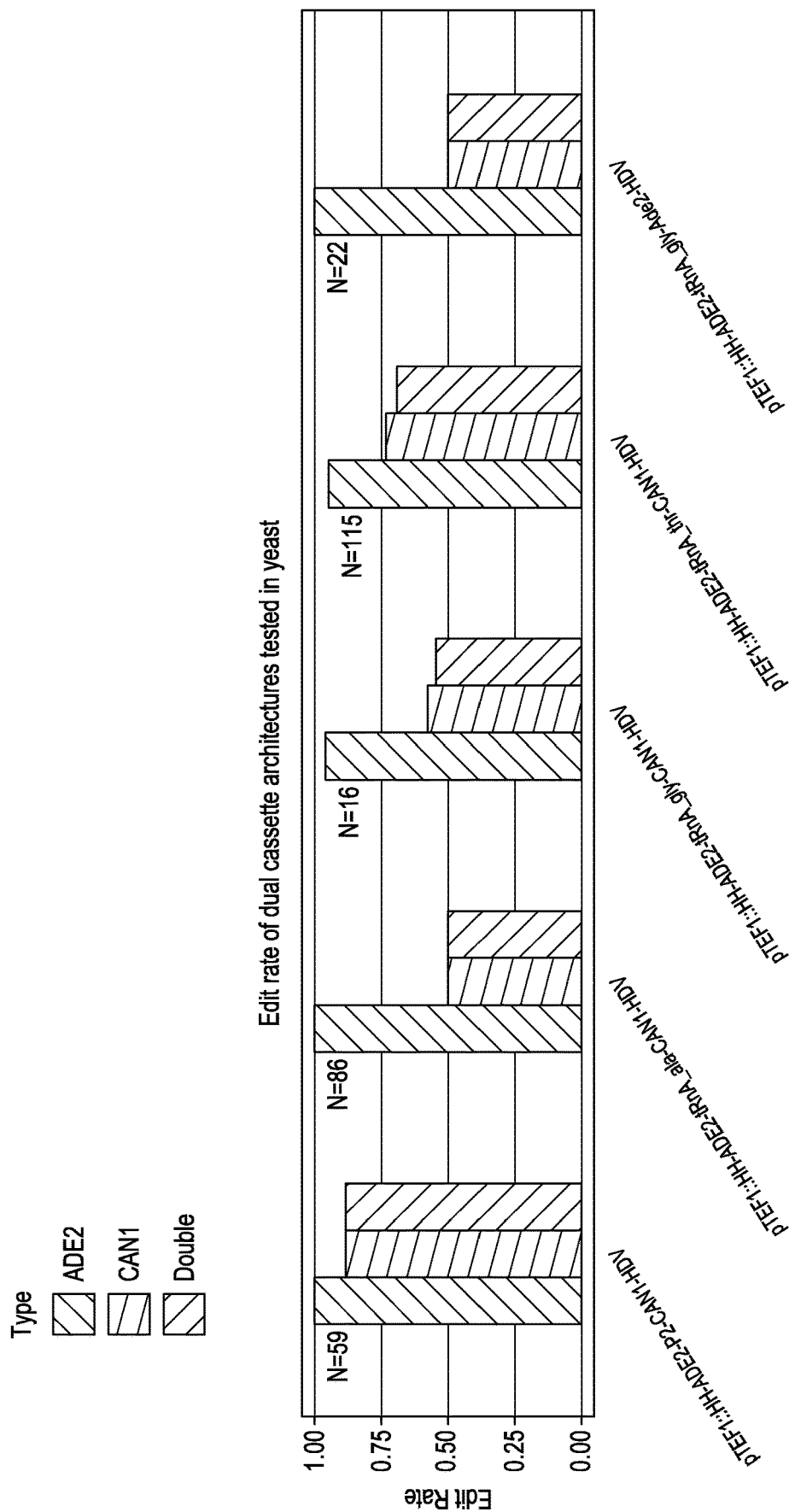
FIG. 13 shows the edit rates obtained for each gene targeted for edits by dual ribozyme-containing editing cassettes tested in yeast.

FIG. 13 is a graph showing the edit rates for dual cassette architectures tested in yeast where knockout edits are made to each of the CAN1 and ADE2 genes. Here, a phenotypic readout was used. ADE2 knockouts result in a red phenotype for the cell colonies and CAN1 knockouts allow for growth on canavanine agar medium. The first set of three bars shows a 95% edit rate for the ADE2 gene, an 85% edit rate for the CAN1 gene, and an 85% edit rate for both the CAN1 and ADE2 genes. These results correspond to a dual cassette architecture pTEF1-HH-ADE2-P2-CAN1-HDV, where "pTEF1" denotes the Pol II promoter, "HH" denotes the hammerhead ribozyme, "ADE2" denotes the ADE2 editing cassette comprising both the gRNA and donor DNA, "P2" denotes a primer sequence, "CAN1" denotes the CAN1 editing cassette comprising both the gRNA and donor DNA, and "HDV" denotes the HDV ribozyme. The second set of three bars shows a 95% edit rate for the ADE2 gene, a 50% edit rate for the CAN1 gene, and a 50% edit rate for both the CAN1 and ADE2 genes. These results correspond to the dual cassette architecture pTEF1-HH-ADE2-tRNA(ala)-CAN1-HDV, where "tRNA(ala)" denotes the tRNA for alanine. The third set of three bars shows a 90% edit rate for the ADE2 gene, a 55% edit rate for the CAN1 gene, and a 50% edit rate for both the CAN1 and ADE2 genes. The third set of three bars corresponds to the dual cassette architecture pTEF1-HH-ADE2-tRNA(gly)-CAN1-HDV, where "tRNA(gly)" denotes the tRNA for glycine. The fourth set of three bars shows a 90% edit rate for the ADE2 gene, a 75% edit rate for the CAN1 gene, and a 70% edit rate for both the CAN1 and ADE2 genes. The fourth set of three bars corresponds to the dual cassette architecture pTEF1-HH-ADE2-tRNA(thr)-CAN1-HDV, where "tRNA(thr)" denotes the tRNA for threonine. The last set of three bars shows a 95% edit rate for the CAN1 gene, a 50% edit rate for the ADE2 gene and a 50% edit rate for both the CAN1 and ADE2 genes. The last set of three bars corresponds to the dual cassette architecture pTEF1-HH-CAN1-tRNA(gly)-ADE2-HDV, where "tRNA(gly)" denotes the tRNA for glycine. Thus, the dual editing cassette architecture described herein results in at least 50% of edited cells comprising both the ADE2 and CAN1 edits.

Example 7: Multiplex Simultaneous Editing in Yeast

In the methods used herein, electrocompetent *S. cerevisiae* cells were transformed with a linear vector backbone and a library of editing cassettes. Electrocompetent *Saccharomyces cerevisiae* cells were prepared as follows: The afternoon before transformation was to occur, 10 mL of YPAD was inoculated with the selected *Saccharomyces cerevisiae* strain. The culture was shaken at 250 RPM and 30° C. overnight. The next day, 100 mL of YPAD was added to a 250-mL baffled flask and inoculated with the overnight culture (around 2 mL of overnight culture) until the OD600 reading reached 0.3+/−0.05. The culture was placed in the 30° C. incubator shaking at 250 RPM and allowed to grow for 4-5 hours, with the OD checked every hour. When the culture reached an OD600 of approximately 1.5, 50 mL volumes were poured into two 50-mL conical vials, then centrifuged at 4300 RPM for 2 minutes at room temperature. The supernatant was removed from all 50 ml conical tubes, while avoiding disturbing the cell pellet. 50 mL of a Lithium Acetate/D dithiothreitol solution was added to each conical tube and the pellet was gently resuspended. Both suspensions were transferred to a 250 mL flask and placed in the shaker; then shaken at 30° C. and 200 RPM for 30 minutes.

After incubation was complete, the suspension was transferred to two 50-mL conical vials. The suspensions then were centrifuge at 4300 RPM for 3 minutes, then the supernatant was discarded. Following the lithium acetate/Dithiothreitol treatment step, cold liquids were used and the cells were kept on ice until electroporation. 50 mL of 1 M sorbitol was added and the pellet was resuspended, then centrifuged at 4300 RPM, 3 minutes, 4° C., after which the supernatant was discarded. The 1M sorbitol wash was repeated twice for a total of three washes. 50 uL of 1 M sorbitol was added to one pellet, cells were resuspended, then transferred to the other tube to suspend the second pellet. The volume of the cell suspension was measured and brought to 1 mL with cold 1 M sorbitol.

500 ng linear vector backbone and 50 ng of the editing cassette library were added to an electroporation cuvette and placed on ice. 100 µL of the electrocompetent cells were added to the cuvette and electroporated under the following conditions: poring pulse: 1800 V, 5.0 msec pulse length, 50.0 msec pulse interval, 1 pulse; transfer pulse: 100 V, 50.0 msec pulse length, 50.0 msec pulse interval, and 3 pulses. Following electroporation, the cells were transferred to a 15 mL tube and shaken at 30° C. and 250 rpm for 3 hours. 9 mL of YPAD and 10 µL G418 1000× stock was added to the tube. 10 µL of each transformation dilution was spread on 2XYPD+Kan plates and incubated at 30° C. for 3 days.

FIG. 14 shows the results for using the methods disclosed above to edit various loci in the genome of *S. cerevisiae*. In the data generated for FIG. 14, a library of 500 different editing cassettes were combined with a single linear vector backbone, and 9 random colonies were picked for analysis. Eight samples comprised two different edits, and one sample comprised three different edits. Note that the fraction of cells comprising more than one edit ranged from 7 to 80%.

FIG. 15 shows the unique plasmids observed via NextGen sequencing of a 500-member editing library across different editing cassette library DNA concentrations. Note that at 1× (e.g., 50 ng of editing cassette library) there was a mean of 0.9375 unique plasmids identified per well, but at 50×, a mean of 1.6875 unique plasmids were identified per well.

Figure 16:
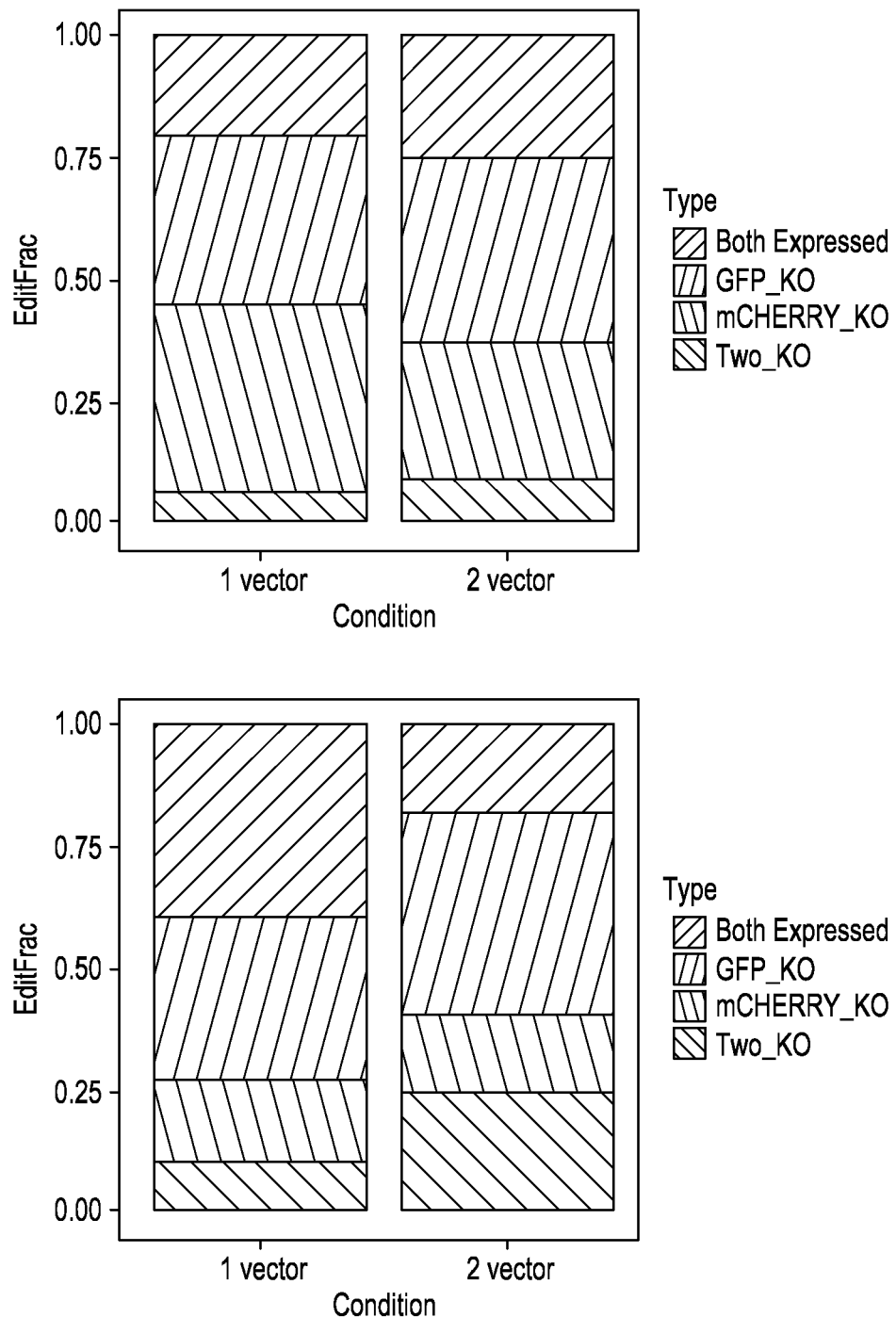
FIG. 16 comprises two bar graphs showing the increased editing rate obtained utilizing a double antibiotic selection scheme versus a single antibiotic selection scheme.

FIG. 16 shows two bar graphs demonstrating that forced MVT and dual antibiotic selection approximately doubles the dual edit rate compared to single antibiotic selection. In the two bar graphs on the left, in the left-most bar graph, 6% dual edits were observed, 33.2% GFP knock out edits were observed, 39.1% mCherry knock out edits were observed, and 21.3% were unedited; in the right bar graph in this duo, 10.2% dual edits were observed, 37.2% GFP knock out edits were observed, 27.1% mCherry knock out edits were observed, and 25.6% were unedited. In the two bar graphs on the right, in the left bar graph, 10.7% dual edits were observed, 33.2% GFP knock out edits were observed, 16.7% mCherry knock out edits were observed, and 39.3% were unedited; and in the right-most bar graph 24.7% dual edits were observed, 41.0% GFP knock out edits were observed, 16.1% mCherry knock out edits were observed, and 18.2% were unedited;

Example 8: Fully-Automated Singleplex RGN-Directed Editing Run

Singleplex automated genomic editing using MAD7 nuclease was successfully performed with an automated multi-module instrument of the disclosure. See U.S. Pat. No. 9,982,279.

An ampR plasmid backbone and a lacZ_F172* editing cassette were assembled via Gibson Assembly® into an "editing vector" in an isothermal nucleic acid assembly module included in the automated instrument. lacZ F172 functionally knocks out the lacZ gene. "lacZ_F172*" indicates that the edit happens at the 172nd residue in the lacZ amino acid sequence. Following assembly, the product was de-salted in the isothermal nucleic acid assembly module using AMPure beads, washed with 80% ethanol, and eluted in buffer. The assembled editing vector and recombineering-ready, electrocompetent *E. Coli* cells were transferred into a transformation module for electroporation. The transformation module comprised an ADP-EPC cuvette. See, e.g., U.S. Pat No. 62/551,069. The cells and nucleic acids were combined and allowed to mix for 1 minute, and electroporation was performed for 30 seconds. The parameters for the poring pulse were: voltage, 2400 V; length, 5 ms; interval, 50 ms; number of pulses, 1; polarity, +. The parameters for the transfer pulses were: Voltage, 150 V; length, 50 ms; interval, 50 ms; number of pulses, 20; polarity, +/−. Following electroporation, the cells were transferred to a recovery module (another growth module) and allowed to recover in SOC medium containing chloramphenicol. Carbenicillin was added to the medium after 1 hour, and the cells were allowed to recover for another 2 hours. After recovery, the cells were held at 4° C. until recovered by the user.

After the automated process and recovery, an aliquot of cells was plated on MacConkey agar base supplemented with lactose (as the sugar substrate), chloramphenicol and carbenicillin and grown until colonies appeared. White colonies represented functionally edited cells, purple colonies represented un-edited cells. All liquid transfers were performed by the automated liquid handling device of the automated multi-module cell processing instrument.

The result of the automated processing was that approximately $1.0E^{-03}$ total cells were transformed (comparable to conventional benchtop results), and the editing efficiency was 83.5%. The lacZ_172 edit in the white colonies was confirmed by sequencing of the edited region of the genome of the cells. Further, steps of the automated cell processing were observed remotely by webcam and text messages were sent to update the status of the automated processing procedure.

Example 9: Fully-Automated Recursive Editing Run

Recursive editing was successfully achieved using the automated multi-module cell processing system. An ampR plasmid backbone and a lacZ_V10* editing cassette were assembled via Gibson Assembly® into an "editing vector" in an isothermal nucleic acid assembly module included in the automated system. Similar to the lacZ_F172 edit, the lacZ_V10 edit functionally knocks out the lacZ gene. "lacZ_V10" indicates that the edit happens at amino acid position 10 in the lacZ amino acid sequence. Following assembly, the product was de-salted in the isothermal nucleic acid assembly module using AMPure beads, washed with 80% ethanol, and eluted in buffer. The first assembled editing vector and the recombineering-ready electrocompetent E. Coli cells were transferred into a transformation module for electroporation. The transformation module comprised an ADP-EPC cuvette. The cells and nucleic acids were combined and allowed to mix for 1 minute, and electroporation was performed for 30 seconds. The parameters for the poring pulse were: voltage, 2400 V; length, 5 ms; interval, 50 ms; number of pulses, 1; polarity, +. The parameters for the transfer pulses were: Voltage, 150 V; length, 50 ms; interval, 50 ms; number of pulses, 20; polarity, +/−. Following electroporation, the cells were transferred to a recovery module (another growth module) allowed to recover in SOC medium containing chloramphenicol. Carbenicillin was added to the medium after 1 hour, and the cells were grown for another 2 hours. The cells were then transferred to a centrifuge module and a media exchange was then performed. Cells were resuspended in TB containing chloramphenicol and carbenicillin where the cells were grown to OD600 of 2.7, then concentrated and rendered electrocompetent.

During cell growth, a second editing vector was prepared in the isothermal nucleic acid assembly module. The second editing vector comprised a kanamycin resistance gene, and the editing cassette comprised a galK Y145* edit. If successful, the galK Y145* edit confers on the cells the ability to uptake and metabolize galactose. The edit generated by the galK Y154* cassette introduces a stop codon at the 154th amino acid reside, changing the tyrosine amino acid to a stop codon. This edit makes the galK gene product nonfunctional and inhibits the cells from being able to metabolize galactose. Following assembly, the second editing vector product was de-salted in the isothermal nucleic acid assembly module using AMPure beads, washed with 80% ethanol, and eluted in buffer. The assembled second editing vector and the electrocompetent E. Coli cells (that were transformed with and selected for the first editing vector) were transferred into a transformation module for electroporation, using the same parameters as detailed above. Following electroporation, the cells were transferred to a recovery module (another growth module), allowed to recover in SOC medium containing carbenicillin. After recovery, the cells were held at 4° C. until retrieved, after which an aliquot of cells were plated on LB agar supplemented with chloramphenicol, and kanamycin. To quantify both lacZ and galK edits, replica patch plates were generated on two media types: 1) MacConkey agar base supplemented with lactose (as the sugar substrate), chloramphenicol, and kanamycin, and 2) MacConkey agar base supplemented with galactose (as the sugar substrate), chloramphenicol, and kanamycin. All liquid transfers were performed by the automated liquid handling device of the automated multi-module cell processing system.

In this recursive editing experiment, 41% of the colonies screened had both the lacZ and galK edits, the results of which were comparable to the double editing efficiencies obtained using a "benchtop" or manual approach.

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are snot to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, ¶6.

We claim:

1. A composition of matter comprising libraries of linear vector backbones and libraries of editing cassettes to be transformed into yeast cells comprising:
    a first linear vector backbone library, wherein each first linear vector backbone in the first linear vector backbone library comprises a coding sequence for a nuclease, a coding sequence for a first antibiotic resistance gene, first homology regions for inserting a first library of editing cassettes, and a 2µ origin of replication;

a second linear vector backbone library, wherein each second linear vector backbone in the second linear vector backbone library comprises a coding sequence for a nuclease, a coding sequence for a second antibiotic resistance gene, second homology regions for inserting a second library of editing cassettes, and a 2μ origin of replication;

the first library of editing cassettes, wherein each editing cassette in the first library of editing cassettes comprises a gRNA and a donor DNA, wherein the gRNAs and donor DNAs of different editing cassettes in the first library of editing cassettes target different target regions in a yeast genome, wherein each donor DNA comprises an edit configured to render inactive a protospacer motif (PAM) in the target sequence, and wherein homology exists between the editing cassettes in the first library of editing cassettes and the first linear vector backbone library; and the second library of editing cassettes, wherein each editing cassette in the second library of editing cassettes comprises a gRNA and a donor DNA, wherein the gRNAs and donor DNAs of different editing cassettes in the second library of editing cassettes target different target regions in a yeast genome, wherein each donor DNA comprises an edit configured to render inactive a protospacer motif (PAM) in the target sequence, and wherein homology exists between the editing cassettes in the second library of editing cassettes and the second linear vector backbone library.

2. The composition of matter of claim 1 further comprising a third linear vector backbone library wherein each third linear vector backbone in the third linear vector backbone library comprises a coding sequence for a nuclease, third homology regions for inserting a third library of editing cassettes, a coding sequence for a third antibiotic resistance gene, and a 2μ origin of replication; and the third library of editing cassettes, wherein each editing cassette in the third library of editing cassettes comprises a gRNA and a donor DNA, wherein the gRNAs and donor DNAs of different editing cassettes in the third library of editing cassettes target different target regions in a yeast genome, wherein each donor DNA comprises an edit configured to render inactive a protospacer motif (PAM) in the target sequence, and wherein homology exists between editing cassettes in the third library of editing cassettes and the third linear vector backbone library.

3. The composition of matter of claim 2 further comprising a fourth linear vector backbone library wherein each fourth linear vector backbone in the fourth linear vector backbone library comprises a coding sequence for a nuclease, fourth homology regions for inserting a fourth library of editing cassettes, a coding sequence for a fourth antibiotic resistance gene, and a 2μ origin of replication; and the fourth library of editing cassettes, wherein each editing cassette in the fourth library of editing cassettes comprises a gRNA and a donor DNA, wherein the gRNAs and donor DNAs of different editing cassettes in the fourth library of editing cassettes target different target regions in a yeast genome, wherein each donor DNA comprises an edit configured to render inactive a protospacer motif (PAM) in the target sequence, and wherein homology exists between the editing cassettes in the fourth library of editing cassettes and the fourth linear vector backbone library.

4. The composition of matter of claim 1, wherein the first and second antibiotic resistance genes confer resistance to hygromycin, G418, blasticidin, puromycin or nourseothricin and the first and second antibiotic resistance genes are different.

5. The composition of matter of claim 1, wherein at least one editing cassette of each library of editing cassettes comprises two gRNAs and two donor DNAs.

6. The composition of matter of claim 1, wherein each editing cassette of each library of editing cassettes comprises three gRNAs and three donor DNAs.

7. The composition of matter of claim 1, where at least one linear vector backbone in each linear backbone library further comprises a promoter for driving expression of the editing cassette.

8. The composition of matter of claim 7, wherein the promoter is a pol II promoter.

9. The composition of matter of claim 8, wherein the pol II promoter is a pPGK1, pTDH3, pENO2, pADH1, pTPI1, pTEF1, pTEF2, pYEF3, pRPL3, pRPL15A, pRPL4, pRPL8B, pSSA1, pSSB1, or pPDA1 promoter.

10. The composition of matter of claim 1, wherein each linear vector backbone in each linear backbone library further comprises an origin of replication functional in bacteria.

11. A composition of matter comprising libraries of linear vector backbones and libraries of editing cassettes to be transformed into yeast cells comprising:

a first linear vector backbone library wherein each linear vector backbone in the first linear vector backbone library comprises a coding sequence for a nuclease, a coding sequence for a first portion of a first antibiotic resistance gene fused to an N-terminus of a first intein, first homology regions for inserting a first library of editing cassettes, and a 2μ origin of replication;

a second linear vector backbone library wherein each linear vector backbone in the second linear vector backbone library comprises a coding sequence for a nuclease, a coding sequence for a second portion of a first antibiotic resistance gene fused to an C-terminus of the first intein, second homology regions for inserting a second library of editing cassettes, and a 2μ origin of replication;

the first library of editing cassettes, wherein each editing cassette in the first library of editing cassettes comprises a gRNA and a donor DNA, wherein the gRNAs and donor DNAs of different editing cassettes in the first library of editing cassettes target different target regions in a yeast genome, wherein each donor DNA comprises an edit configured to render inactive a protospacer motif (PAM) in the target sequence, and wherein homology exists between the first library of editing cassettes and the first linear vector backbone library; and the second library of editing cassettes, wherein each editing cassette in the second library of editing cassettes comprises a gRNA and a donor DNA, wherein the gRNAs and donor DNAs of different editing cassettes in the second library of editing cassettes target different target regions in a yeast genome, wherein each donor DNA comprises an edit configured to render inactive a protospacer motif (PAM) in the target sequence, and wherein homology exists between the second library of editing cassettes and the second linear vector backbone library.

12. The composition of matter of claim 11 further comprising a third linear vector backbone library wherein each third linear vector backbone in the third linear vector backbone library comprises a coding sequence for a nuclease, third homology regions for inserting a third library of editing cassettes, a coding sequence for a first portion of a second antibiotic resistance gene fused to the N-terminus of a second intein, and a 2µ origin of replication; a fourth linear vector backbone library wherein each fourth linear vector backbone in the fourth linear vector backbone library comprises a coding sequence for a nuclease, fourth homology regions for inserting a fourth library of editing cassettes, a coding sequence for a second portion of a second antibiotic resistance gene fused to a C-terminus of the second intein, and a 2µ origin of replication; the third library of editing cassettes, wherein each editing cassette in the third library of editing cassettes comprises a gRNA and a donor DNA, wherein the gRNAs and donor DNAs of different editing cassettes in the third library of editing cassettes target different target regions in a yeast genome, wherein each donor DNA comprises an edit configured to render inactive a protospacer motif (PAM) in the target sequence, and wherein homology exists between the third library of editing cassettes and the third linear vector backbone library; and the fourth library of editing cassettes, wherein each editing cassette in the fourth library of editing cassettes comprises a gRNA and a donor DNA, wherein the gRNAs and donor DNAs of different editing cassettes in the fourth library of editing cassettes target different target regions in a yeast genome, wherein each donor DNA comprises an edit configured to render inactive a protospacer motif (PAM) in the target sequence, and wherein homology exists between the fourth library of editing cassettes and the fourth linear vector backbone library.

13. The composition of matter of claim 11, wherein the first intein is obtained from *Nostoc punctiforme* PCC73102 split alpha subunit of the DNA polymerase III intein (NpuDnaE), *Synechocystis* sp. PCC6803 DnaB helicase SspDnaB, or CfaDnaE.

14. The composition of matter of claim 11, wherein the first antibiotic resistance gene confers resistance to hygromycin, G418, blasticidin, puromycin or nourseothricin.

15. The composition of matter of claim 11, wherein each editing cassette of each library of editing cassettes comprises two gRNAs and two donor DNAs.

16. The composition of matter of claim 11, wherein each editing cassette of each library of editing cassettes comprises three gRNAs and three donor DNAs.

17. The composition of matter of claim 11, where each linear vector backbone in each linear backbone library further comprises a promoter for driving expression of the editing cassette.

18. The composition of matter of claim 17, wherein the promoter is a pol II promoter.

19. The composition of matter of claim 18, wherein the pol II promoter is a pPGK1, pTDH3, pENO2, pADH1, pTPI1, pTEF1, pTEF2, pYEF3, pRPL3, pRPL15A, pRPL4, pRPL8B, pSSA1, pSSB1, or pPDA1 promoter.

20. The composition of matter of claim 11, wherein each linear vector backbone in each linear backbone library further comprises an origin of replication functional in bacteria.

* * * * *